United States Patent
Blaszczak et al.

(10) Patent No.: US 8,133,907 B2
(45) Date of Patent: Mar. 13, 2012

(54) PYRIDINE DERIVATIVES AS DIPEPTEDYL PEPTIDASE INHIBITORS

(75) Inventors: Larry Chris Blaszczak, Indianapolis, IN (US); Brian Michael Mathes, Indianapolis, IN (US); Shon Roland Pulley, Noblesville, IN (US); Michael Alan Robertson, Indianapolis, IN (US); Scott Martin Sheehan, Carmel, IN (US); Qing Shi, Carmel, IN (US); Brian Morgan Watson, Carmel, IN (US); Michael Robert Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1058 days.

(21) Appl. No.: 11/996,126

(22) PCT Filed: Jul. 14, 2006

(86) PCT No.: PCT/US2006/027465
§ 371 (c)(1),
(2), (4) Date: Jan. 18, 2008

(87) PCT Pub. No.: WO2007/015767
PCT Pub. Date: Feb. 8, 2007

(65) Prior Publication Data
US 2008/0214616 A1    Sep. 4, 2008

Related U.S. Application Data

(60) Provisional application No. 60/700,873, filed on Jul. 20, 2005.

(51) Int. Cl.
A61K 31/4425   (2006.01)
A61K 31/44     (2006.01)
C07D 213/56    (2006.01)
C07D 401/06    (2006.01)

(52) U.S. Cl. ........ 514/352; 514/318; 514/354; 546/194; 546/304; 546/337

(58) Field of Classification Search .................. 546/194, 546/304, 337; 514/318, 352, 354
See application file for complete search history.

(56) References Cited

U.S. PATENT DOCUMENTS

| 5,714,142 A | 2/1998 | Blaney et al. |
| 2004/0167133 A1 | 8/2004 | Edmondson et al. |
| 2004/0236102 A1 | 11/2004 | Brockunier et al. |

FOREIGN PATENT DOCUMENTS

| WO | WO 91/00858 A1 | 1/1991 |
| WO | WO 96/41795 A1 | 12/1996 |
| WO | WO 03/000181 A2 | 1/2003 |
| WO | WO 03/004498 A1 | 1/2003 |
| WO | WO 03/068757 A1 | 8/2003 |
| WO | WO 03/082817 A2 | 10/2003 |
| WO | WO 2004/037169 A2 | 5/2004 |
| WO | WO 2004/103276 A2 | 12/2004 |
| WO | WO 2005/039485 A2 | 5/2005 |
| WO | WO 2007/015805 | 2/2007 |
| WO | WO 2007/015807 | 2/2007 |

OTHER PUBLICATIONS

Hunziker et al., "Inhibitiors of, etc.," Current Topics in Medicinal Chemistry, 2005, 5, 1623-1637.*
Arulmozhi et al., GLP-1 based, etc., European Journal of Pharmacutical Sciences 28 (2006) 96-108.*
C. Rummey et al, "In silico fragment-based discovery of DPP-IV S1 pocket binders", Bioorganic & Medicinal Chemistry Letters 16 (2006) pp. 1405-1409.
J. Peters et al, "Aminomethylpyrimidines as novel DPP-IV inhibitors: A $10^5$-fold activity increase by optimization of aromatic substituents", Bioorganic & Medicinal Chemistry Letters 14 (2004), pp. 1491-1493.

* cited by examiner

*Primary Examiner* — Patricia Morris
(74) *Attorney, Agent, or Firm* — James B. Myers

(57) ABSTRACT

The present invention is directed to compounds of formula (I) or a pharmaceutically acceptable salt thereof; wherein A is (1); X is selected from CH, CF and N; R5 is selected from H, $C_1$-$C_6$ alkyl, $C_1$-$C_6$ fluoroalkyl, and —OR12; R9 is selected from H —NR13C(O)R14 and —C(O)NR10R11; R12 is selected from H, $C_1$-$C_6$ alkyl and $C_3$-$C_6$ cycloalkyl, for use as inhibitors of the DPP-IV enzyme in the treatment or prevention of conditions including Type II diabetes.

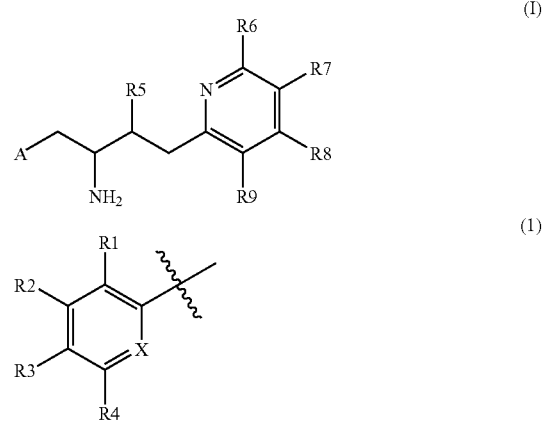

19 Claims, 2 Drawing Sheets

PYRIDINE DERIVATIVES AS DIPEPTEDYL PEPTIDASE INHIBITORS

REFERENCE TO RELATED APPLICATION

This application is submitted as a United States national phase entry, pursuant to 35 U.S.C. §371, of PCT/US2006/027465, filed on 14 Jul. 2006, which claims the benefit of United States provisional patent application Ser. No. 60/700,873, filed 20 Jul. 2005, each of which is incorporated by reference herein.

BACKGROUND OF THE INVENTION

Diabetes is a chronic disease that features abnormal glucose homeostasis, the disease has been differentiated into two forms; Type I or insulin-dependent diabetes mellitus (IDDM) and Type II or non-insulin-dependent diabetes mellitus (NIDDM). Type II diabetes accounts for 90% of all cases of diabetes and in 1994 was estimated by the World Health Organization to affect 2-3% of the world's population with diagnosis rates rising at 4-5% per year.

The initial stage of Type II diabetes is characterized by insulin resistance which is initially compensated, in part, by increased production of insulin by pancreatic β cells, over time these cells become exhausted and insulin production decreases. The combined effects of insulin resistance and decreased insulin production reduce glucose uptake and utilization by skeletal muscle and prevent insulin-mediated suppression of hepatic glucose output. As the disease progresses blood glucose levels increase, postprandial hyperglycaemia is observed which upon further development leads to a state of fasting hyperglycaemia.

Type II diabetes is a component of a disease cluster known as metabolic syndrome, comprising a variety of disorders including glucose intolerance/insulin resistance, arterial hypertension, dyslipidaemia and obesity. For Type II diabetic patients suffering from poor glycaemic control the major cause for concern are chronic complications such as retinopathy, nephropathy, neuropathy and atherosclerosis. The treatments currently available for Type II diabetes range from increased exercise in combination with decreased calorific intake to, when other treatment options fail, the injection of exogenous insulin. Within this range of treatments are a number of oral pharmacological agents which may be administered individually or, for patients where the disease is more advanced, in combination to achieve better glycaemic control.

Current oral pharmacological agents include sulfonylureas (e.g. tolbutamide) and glinides which stimulate the pancreatic β cells, increasing insulin secretion. Also, acarbose which is an α-glucosidase inhibitor that reduces the rate of intestinal carbohdrate digestion and therefore absorption. Biguanidines, such as metformin and glitazones, counter insulin resistance by decreasing hepatic glucose output and increasing muscle insulin sensitivity. The glitazones (thiazolidinediones) exert their action by acting as agonists of the peroxisome proliferator activated receptor (PPAR) and more particularly the PPAR-γ receptor.

As a consequence of side effects associated with the current oral pharmacological agents, namely, sulfonylurea and glinide induced hypoglycaemia, acarbose induced gastrointestinal disturbances, metformin induced lactic acidosis and glitazone induced liver toxicity, there continues to be a demand for the development of alternative oral antidiabetic agents.

There are a wide variety of alternative approaches to glycaemic control currently under investigation. Alternative approaches under investigation include, treatment with PPAR-α or PPAR-δ agonists, rexinoid X receptor (RXR) agonists, protein tyrosine phosphatase 1B (PTP-1B) inhibitors and glycogen synthase kinase (GSK)-3 inhibitors.

Dipeptidyl peptidase IV (DPP-IV) is a widely expressed glycoprotein present in cells in most tissues, including the kidney, gastrointestinal tract and liver and is responsible for the rapid degradation of several regulatory peptides including the incretin hormones, glucagon-like peptide-1 (GLP-1) and glucose-dependent insulinotropic polypeptide (GIP). GLP-1 is released from the intestinal tract wall into the bloodstream in response to nutrient ingestion and is an integral component in the physiological control of insulin release, and therefore the regulation of blood glucose. Inhibiting DPP-IV enhances the body's normal homeostatic mechanisms resulting in increased levels of GLP-1, lead to higher plasma insulin concentrations and thus regulate blood glucose.

Advantageously, DPP-IV inhibitors in utilising the body's normal homeostatic mechanisms, insulin levels will only be increased at appropriate times such as in response to nutrient ingestion. This mode of action significantly reduces the risk of hypoglycaemia, and highlights DPP-IV inhibitors as a target of interest for the development of alternative oral antidiabetic agents.

Compounds that are inhibitors of DPP-IV and which may be useful in the treatment of diabetes have been described in the art. These compounds include thiazolidine derivatives (e.g. *Drugs of the Future*, (2001) 26: 859-864, WO 99/61431, U.S. Pat. No. 6,110,949, WO 03/037327) and pyrrolidine derivatives (e.g. *Diabetes*, (2002) 51: 1461-1469, WO 98/19998, WO 01/40180, WO 03/037327). Other compounds include piperidine, piperizine and morpholine derivatives (e.g. WO 03/000181, WO 03/082817). Still others include pyridine derivatives (e.g. WO 03/068748, WO 03/068757, WO 05/042488)

The present invention relates to pyridine compounds which are inhibitors of the DPP-IV enzyme, pharmaceutical compositions containing them as active ingredient, methods for the treatment or prevention of diseases in which the DPP-IV enzyme is involved, to their use as medicaments and to their use in the manufacture of medicaments for the treatment or prevention of diseases in which the DPP-IV enzyme is involved, such as diabetes and particularly Type II diabetes.

Figure 1:
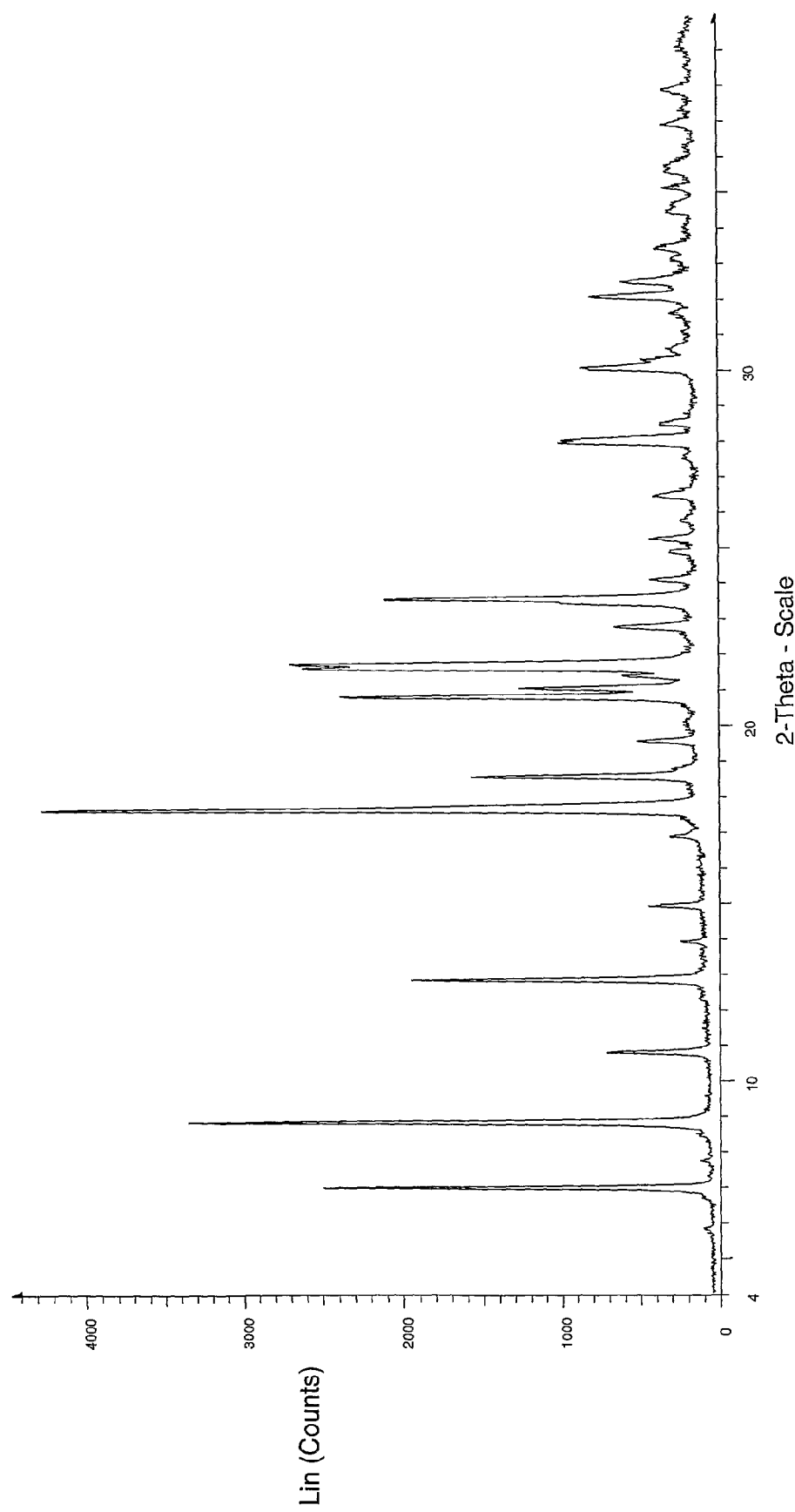
FIG. 1 (FIG. 1) illustrates an XRPD trace of 2-[(2S,3R)-3-Amino-4-(2,5-difluoro-phenyl)-2-hydroxy-butyl]-N-tert-butyl-6-trifluoromethyl-nicotinamide (Form I).

The compounds of the present invention are described by structural formula I:

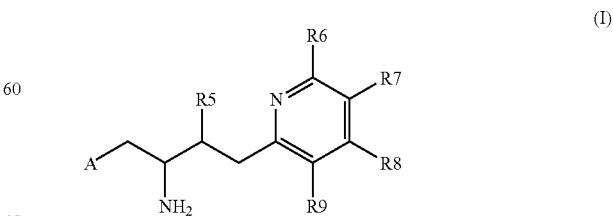

or a pharmaceutically acceptable salt thereof;

wherein
A is

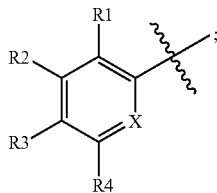

R1 is selected from H, halo, $C_1$-$C_4$ alkyl, $C_1$-$C_4$ alkoxy, $C_1$-$C_4$ haloalkyl, $C_1$-$C_4$ haloalkoxy, CN and hydroxy;

R2, R3, and R4 are independently selected from H, halo, methyl, ethyl, methoxy, $C_1$-$C_2$ haloalkyl, $C_1$ haloalkoxy, CN and hydroxy;

X is selected from CH, CF and N;

R5 is selected from H, $C_1$-$C_6$ alkyl, $C_1$-$C_6$ fluoroalkyl, and —OR12;

R6 is selected from H, halo, $C_1$-$C_6$ alkyl, $C_1$-$C_6$ alkoxy, $C_1$-$C_4$ alkyl-O— $C_1$-$C_4$ alkyl, $C_1$-$C_6$ haloalkyl, hydroxy $C_1$-$C_6$ alkyl, CN and hydroxy, or R6 and R7 combine to form a 5-8 membered carbocyclic ring or a 5-6 membered heteroaryl ring optionally substituted with 1-3 substituents selected from methoxy, Cl, F, $CH_3$ and $CF_3$;

R7 and R8 are independently selected from H, halo, $C_1$-$C_6$ alkyl, aryl, heteroaryl, $C_1$-$C_6$ alkylaryl, $C_1$-$C_6$ alkylheteroaryl, $C_1$-$C_6$ alkoxy, $C_1$-$C_6$ alkyl-O—$C_1$-$C_6$ alkyl, $C_1$-$C_6$ haloalkyl, hydroxy $C_1$-$C_6$ alkyl, CN and hydroxy or R7 and R8 combine to form a 5-8 membered carbocyclic ring or a 5-6 membered heteroaryl ring optionally substituted with 1-3 substituents selected from methoxy, Cl, F, $CH_3$ and $CF_3$;

R9 is selected from H, —NR13C(O)R14 and —C(O)NR10R11;

R10 and R11 are independently selected from H, $C_1$-$C_6$ alkyl, $C_1$-$C_6$ haloalkyl, aryl, heteroaryl, $C_3$-$C_6$ cycloalkyl, $C_1$-$C_6$ alkylaryl, $C_1$-$C_6$ alkylheteroaryl, $C_1$-$C_6$ alkyl-$C_3$-$C_6$ cycloalkyl or R10 and R11 combine with the N of R9 to form a 4 to 8 membered heterocycle;

where R7, R8, R10 or R11 are aryl, heteroaryl, $C_1$-$C_6$ alkylaryl or $C_1$-$C_6$ alkylheteroaryl the aryl or heteroaryl substituents are optionally substituted with 1-3 substituents selected from methoxy, Cl, F, $CH_3$ and $CF_3$;

R12 is selected from H, $C_1$-$C_6$ alkyl and $C_3$-$C_6$ cycloalkyl;

R13 is selected from H and $C_1$-$C_4$ alkyl;

R14 is selected from $C_1$-$C_6$ alkyl, $C_1$-$C_6$ haloalkyl, aryl, heteroaryl, $C_3$-$C_6$ cycloalkyl, $C_1$-$C_6$ alkylaryl, $C_1$-$C_6$ alkylheteroaryl and $C_1$-$C_6$ alkyl-$C_3$-$C_6$ cycloalkyl; with the proviso that where R1, R2, R3 and R4 are H at least one of R6, R7, R8 or R9 is not H; and with the proviso that where R1, R2, R3 and R4 are H and X is CH at least one of R6, R7, R8 or R9 is not H; and with the proviso that where R6, R7, R8 and R9 are H at least one of R1, R2, R3 or R4 is not H or X is not CH; and with the further proviso that when R1, R2, R3, R4, R6, R7, R8 and R9 are H and X is CH that R5 is not H.

Preferred compounds of the invention are of formula I wherein
A is

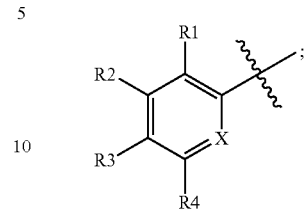

R1 is selected from H, halo, $C_1$-$C_4$ alkyl, $C_1$-$C_4$ alkoxy, $C_1$-$C_4$ haloalklyl, $C_1$-$C_4$ haloalkoxy, CN and hydroxy;

R2, R3, and R4 are independently selected from H, halo, methyl, ethyl, methoxy, $C_1$-$C_2$ haloalkyl, $C_1$ haloalkoxy, CN and hydroxy;

X is selected from CH, CF and N;

R5 is selected from H, $C_1$-$C_6$ alkyl, $C_1$-$C_6$ fluoroalkyl, and —OR12;

R6 is selected from H, halo, $C_1$-$C_6$ alkyl, $C_1$-$C_6$ alkoxy, $C_1$-$C_4$ alklyl-O— $C_1$-$C_4$ alkyl, $C_1$-$C_6$ haloalkyl, hydroxy $C_1$-$C_6$ alkyl, CN and hydroxy, or R6 and R7 combine to form a 5-8 membered carbocyclic ring or a 5-6 membered heteroaryl ring optionally substituted with 1-3 substituents selected from methoxy, Cl, F, $CH_3$ and $CF_3$;

R7 and R8 are independently selected from H, halo, $C_1$-$C_6$ alkyl, aryl, heteroaryl, $C_1$-$C_6$ alkylaryl, $C_1$-$C_6$ alkylheteroaryl, $C_1$-$C_6$ alkoxy, $C_1$-$C_6$ alkyl-O—$C_1$-$C_6$ alkyl, $C_1$-$C_6$ haloalkyl, hydroxy $C_1$-$C_6$ alkyl, CN and hydroxy or R7 and R8 combine to form a 5-8 membered carbocyclic ring or a 5-6 membered heteroaryl ring optionally substituted with 1-3 substituents selected from methoxy, Cl, F, $CH_3$ and $CF_3$;

R9 is selected from H and —C(O)NR10R11;

R10 and R11 are independently selected from H, $C_1$-$C_6$ alkyl, $C_1$-$C_6$ haloalkyl, aryl, heteroaryl, $C_1$-$C_6$ alkylaryl, $C_1$-$C_6$ alkylheteroaryl or R10 and R11 combine with the N of R9 to form a 4 to 8 membered heterocycle;

where R7, R8, R10 or R11 are aryl, heteroaryl, $C_1$-$C_6$ alkylaryl or $C_1$-$C_6$ alkylheteroaryl the aryl or heteroaryl substituents are optionally substituted with 1-3 substituents selected from methoxy, Cl, F, $CH_3$ and $CF_3$;

R12 is selected from H, $C_1$-$C_6$ alkyl and $C_3$-$C_6$ cycloalkyl; with the proviso that where R1, R2, R3 and R4 are H at least one of R6, R7, R8 or R9 is not H; and with the proviso that where R1, R2, R3 and R4 are H and X is CH at least one of R6, R7, R8 or R9 is not H; and with the proviso that where R6, R7, R8 and R9 are H at least one of R1, R2, R3 or R4 is not H or X is not CH; and with the further proviso that when R1, R2, R3, R4, R6, R7, R8 and R9 are H and X is CH that R5 is not H; or a pharmaceutically acceptable salt thereof.

A preferred species of the compounds of formula I are compounds of formula II:

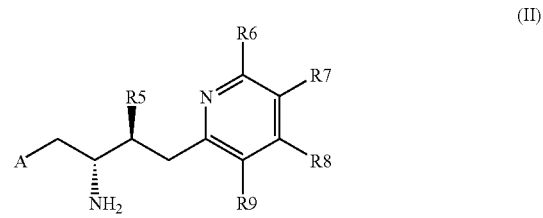

(II)

or a pharmaceutically acceptable salt thereof wherein A, R5, R6, R7, R8 and R9 are as defined herein.

A preferred species of the compounds of formula I are compounds of formula Ia:

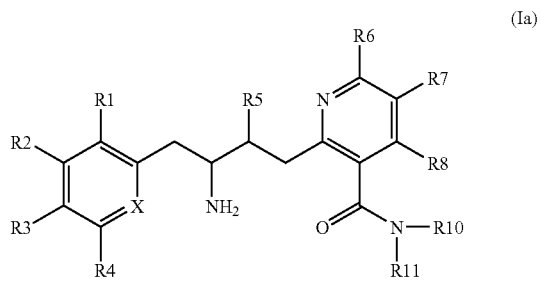

(Ia)

or a pharmaceutically acceptable salt thereof wherein R1, R2, R3, R4, R5, R6, R7, R8, R10 and R11 are as defined herein.

A preferred species of the compounds of formula I are compounds of formula IIa:

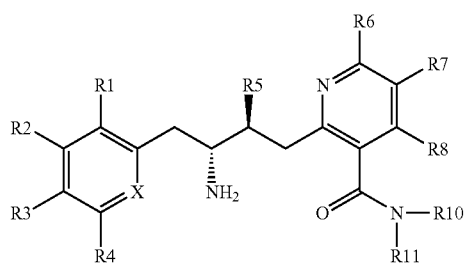

(IIa)

or a pharmaceutically acceptable salt thereof wherein R1, R2, R3, R4, R5, R6, R7, R8, R10 and R11 are as defined herein.

A preferred species of the compounds of formula I are compounds of formula Ib:

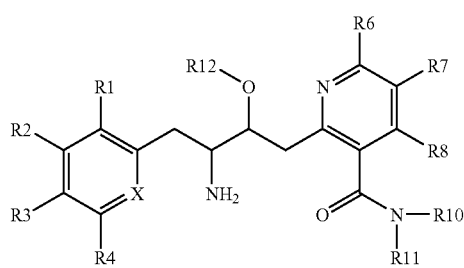

(Ib)

or a pharmaceutically acceptable salt thereof wherein R1, R2, R3, R4, R6, R7, R8, R10, R11 and R12 are as defined herein.

A preferred species of the compounds of formula I are compounds of formula IIb:

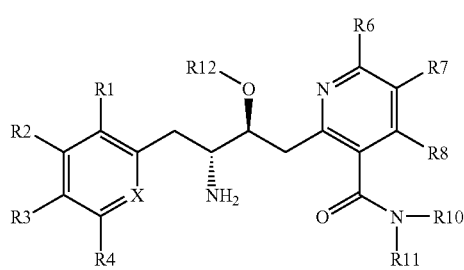

(IIb)

or a pharmaceutically acceptable salt thereof wherein R1, R2, R3, R4, R6, R7, R8, R10, R11 and R12 are as defined herein.

A preferred species of the compounds of formula I are compounds of formula Ic:

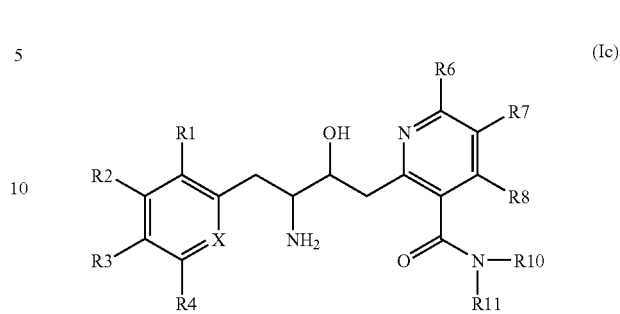

(Ic)

or a pharmaceutically acceptable salt thereof wherein R1, R2, R3, R4, R6, R7, R8, R10, and R11 are as defined herein.

A preferred species of the compounds of formula I are compounds of formula IIc:

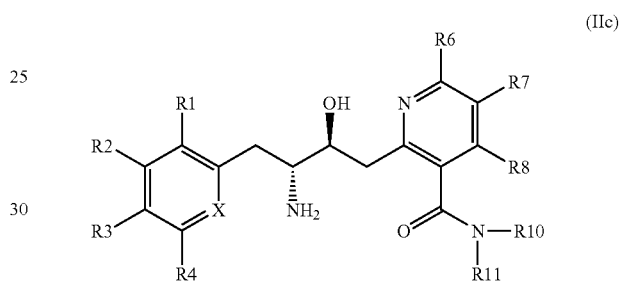

(IIc)

or a pharmaceutically acceptable salt thereof wherein R1, R2, R3, R4, R6, R7, R8, R10, and R11 are as defined herein.

In the present invention it is preferred that R1 and R4 are independently selected from H, F, Cl, $CH_3$ and $CF_3$, it is more preferred that R1 and R4 are independently selected from F, Cl and $CH_3$, more preferably R1 and R4 are independently selected from F and Cl, most preferably R1 is F and R4 is either Cl or F.

In the present invention it is preferred that R5 is —OR12 wherein R12 is as defined herein.

In the present invention it is preferred that where X is N, R1 is selected from H, F and $CH_3$.

In the present invention it is preferred that where X is CH, at least one of R1, R2, R3 or R4 is not H.

In the present invention it is preferred that where R9 is H, R5 is not H.

In the present invention it is preferred that R2 and R3 are independently selected from H, F, Cl, $CH_3$ and $CF_3$, it is more preferred that R2 and R3 are independently selected from H, F and Cl, more preferably R2 and R3 are independently selected from H and F, most preferably R2 is H and R3 is F.

In the present invention it is preferred that R6, R7 and R8 are independently selected from H, F, Cl, $CH_3$, $CF_3$ and $OCH_3$, more preferably H, F, Cl, $CH_3$ and $OCH_3$, most preferably R6, R7 and R8 are H.

In the present invention it is preferred that R7 combines with R6 or R8 to form a 5-6 membered heteroaryl ring selected from pyridyl, pyrimidyl, pyrrolyl, pyrazolyl, isoxazolyl, isothiazolyl, imidazolyl, oxazolyl or thiazolyl, optionally substituted with 1-3 substituents selected from methoxy, Cl, F, $CH_3$ and $CF_3$; preferably R7 combines with R6 or R8 to form a pyrrolyl, pyrazolyl, isoxazolyl, isothiazolyl, imidazolyl, oxazolyl or thiazolyl substituent optionally substituted with 1-2 substituents selected from methoxy, Cl, F, $CH_3$ and $CF_3$; more preferably R7 combines with R6 or R8 to form a pyrazolyl, isoxazolyl, imidazolyl or oxazolyl substituent optionally substituted with 1 substituent selected from methoxy, Cl, F, $CH_3$ and $CF_3$; preferably R7 combines with R6 or R8 to form a isoxazolyl or oxazolyl substituent optionally substituted with 1 substituent selected from methoxy, Cl, F, $CH_3$ and $CF_3$.

In the present invention it is preferred that R9 is C(O)NR10R11 where R10 and R11 are as defined herein.

In the present invention it is preferred that R10 and R11 are independently selected from H, $C_1$-$C_4$ alkyl, aryl and $C_1$-$C_4$ alkylaryl wherein the aryl substituent of $C_1$-$C_6$ alkylaryl is optionally substituted with 1-3 substituents selected from methoxy, Cl, F, $CH_3$ and $CF_3$, more preferably R10 and R11 are independently selected from H, methyl, isopropyl, t-butyl, phenyl, benzyl, 1-methyl benzyl and 1,1-dimethyl benzyl wherein phenyl and benzyl substituents are optionally substituted with 1-3 substituents selected from methoxy, Cl, F, $CH_3$ and $CF_3$, most preferably R10 is H and R11 is t-butyl.

In the present invention it is preferred that X is selected from CH and CF, most preferably X is CH.

In the present invention it is preferred that R12 is selected from $CH_3$ and H, most preferably R12 is H.

The compounds of formula I have been found to act as inhibitors of the DPP-IV enzyme in vitro. More particularly the compounds of formula I show selectivity for inhibition of the DPP-IV enzyme over the DPP 8 and/or DPP 9 enzyme.

The present invention provides pharmaceutical compositions comprising a compound of formula I, or a pharmaceutically acceptable salt thereof together with a pharmaceutically acceptable diluent or carrier.

The present invention provides a method for the treatment or prevention of a disorder associated with DPP-IV dysfunction in mammals, which comprises administering a compound of formula I, or a pharmaceutically acceptable salt thereof, to a human being or animal in need thereof.

The present invention also provides a method for the treatment or prevention of a condition selected from type II diabetes, obesity, hyperglycemia and a lipid disorder, which comprises administering a compound of formula I, or a pharmaceutically acceptable salt thereof, to a human being or animal in need thereof.

The present invention further provides a method for the treatment or prevention of a lipid disorder, which comprises administering a compound of formula I, or a pharmaceutically acceptable salt thereof, to a human being or animal in need thereof wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use as a pharmaceutical; and a compound of formula I, or a pharmaceutically acceptable salt thereof for use in the treatment or prevention of type II diabetes, obesity, hyperglycemia or a lipid disorder.

The present invention also provides a compound of formula I, or a pharmaceutically acceptable salt thereof for use in the treatment or prevention of a lipid disorder, wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use in the manufacture of a medicament for the treatment or prevention of type II diabetes, obesity, hyperglycemia or a lipid disorder.

The present invention provides a compound of formula I, or a pharmaceutically acceptable salt thereof for use in the manufacture of a medicament for the treatment or prevention of a lipid disorder, wherein said lipid disorder is selected from dyslipidemia, hyperlipidemia, hypertriglyceridemia, hypercholesterolemia, low HDL and high LDL.

As used throughout this specification, it is to be understood that where a group is qualified by "defined herein" or "herein defined" that said group encompasses the first occurring and broadest definition as well as each and all of the particular definitions for that group.

As used herein, the term "halo", unless otherwise stated, designate all four halogens, i.e. F, Cl, Br and I. Preferred halogens are F or Cl, most preferred is F.

As used herein the term "alkyl" includes both straight and branched chain alkyl groups and refers to $C_1$-$C_6$ alkyl chains, preferably $C_1$-$C_4$ alkyl chains.

As used herein, the term "$C_1$-$C_4$ alkyl" includes both straight chain and branched chain alkyl groups, such as methyl, ethyl, propyl, isopropyl, butyl, iso-butyl and t-butyl. Preferred $C_1$-$C_4$ alkyl groups include methyl, ethyl, propyl and isopropyl.

As used herein the term "$C_1$-$C_6$ alkyl" includes both straight chain and branched chain alkyl groups, such as methyl, ethyl, propyl, isopropyl, butyl, iso-butyl, t-butyl, pentyl, iso-pentyl, 1,2-dimethylpropyl and hexyl. Preferred $C_1$-$C_6$ alkyl groups include methyl, ethyl, propyl, isopropyl, butyl, iso-butyl and t-butyl As used herein the term "alkoxy" refers to an alkyl group as defined herein linked to an oxygen atom.

As used herein the term "$C_1$-$C_4$ alkoxy" includes methoxy, ethoxy, propoxy, isopropoxy, butoxy, iso-butoxy, t-butoxy. Preferred $C_1$-$C_4$ alkoxy groups include methoxy, ethoxy and isopropoxy.

As used herein the term "$C_1$-$C_6$ alkoxy" includes methoxy, ethoxy, propoxy, isopropoxy, tert-butoxy, pentoxy, iso-pentoxy and 1,2-dimethylpropoxy. Preferred $C_1$-$C_6$ alkoxy groups include methoxy, ethoxy, isopropoxy and tert-butoxy.

As used herein, the term "haloalkyl" refers to an alkyl group as defined herein wherein one or more of the hydrogens is replaced by a halo substituent as defined herein, which replacement can be at any site on the alkyl chain.

As used herein, the term "$C_1$-$C_2$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoromethyl and 1,1,1-trifluoroethyl.

As used herein, the term "$C_1$-$C_4$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoroethyl, 1,1,1-trifluoropropyl and 1,1,1,3,3,3-hexafluoroisopropyl. Preferred $C_1$-$C_4$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "$C_1$-$C_6$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1,1-trifluoroethyl, 1,1,1-trifluoropropyl and 1,1,1,3,3,3-hexafluoroisopropyl. Preferred $C_1$-$C_6$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "fluoroalkyl" refers to a haloalkyl group as defined herein where the halo substituent is fluorine.

As used herein, the term "$C_1$-$C_6$ fluoroalkyl" includes fluoromethyl, difluoromethyl, trifluoromethyl, fluoroethyl, 1,2-difluoroethyl, 1,1-difluoroethyl, trifluoromethyl, 1,1,1-trifluoroethyl, 1,1,1-trifluoropropyl and 1,1,1,3,3,3-hexafluoroisopropyl. Preferred $C_1$-$C_6$ fluoroalkyl groups include fluoromethyl, difluoromethyl, trifluoromethyl, 1,2-difluoroethyl, 1,1-difluoroethyl and 1,1,1-trifluoroethyl, most preferred are fluoromethyl, difluoromethyl and trifluoromethyl.

As used herein, the term "haloalkoxy" refers to an alkoxy group as defined herein wherein one or more of the hydrogens is replaced by a halo substituent as defined herein, which replacement can be at any site on the alkyl chain.

As used herein, the term "$C_1$ haloalkoxy" includes fluoromethoxy, chloromethoxyl, difluoromethoxy, dichloromethoxy, trifluoromethoxy. Preferred $C_1$ haloalkoxy groups include fluoromethoxy, difluoromethoxy and trifluoromethoxy.

As used herein, the term "$C_1$-$C_4$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_4$ haloalkoxy groups include fluoromethoxy, difluoromethoxy, trifluoromethoxy, 1,2-difluoroethyoxy, 1,1-difluoroethoxy and 1,1,1-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein, the term "$C_1$-$C_6$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_6$ haloalkoxy groups include fluoromethoxy, difluoromethoxy, trifluoromethoxy, 1,2-difluoroethoxy, 1,1-difluoroethoxy and 1,1,1-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein the term "hydroxy $C_1$-$C_6$ alkyl" refers to a $C_1$-$C_6$ alkyl group as defined herein wherein one of the hydrogens is replaced by an OH substituent, which replacement can be at any site on the alkyl chain, and includes hydroxy methyl, 1-hydroxy ethyl, 2-hydroxy ethyl, 2-hydroxy propyl, 3-hydroxy propyl, 2-hydroxy isopropyl, 3-hydroxy butyl and 4-hydroxy butyl. Preferred hydroxy($C_1$-$C_6$)alkyl groups include methanol, ethanol, isopropanol, and n-propanol.

As used herein the term "$C_1$-$C_4$ alkyl-O— $C_1$-$C_4$ alkyl" refers to a $C_1$-$C_4$ alkyl group as defined herein wherein one of the hydrogens is replaced by an oxygen substituent which replacement can be at any site on the alkyl chain, wherein the oxygen substituent is attached to a further $C_1$-$C_4$ alkyl group as defined herein, and includes methoxymethyl, ethoxymethyl, propoxymethyl, isopropoxymethyl, tert-butoxymethyl, methoxyethyl, ethoxyethyl, propoxyethyl, isopropoxyethyl, and tert-butoxyethyl. Preferred $C_1$-$C_4$ alkyl-O— $C_1$-$C_4$ alkyl groups include methoxymethyl, ethoxymethyl, methoxyethyl and ethoxyethyl.

As used herein the term "$C_1$-$C_6$ alkyl-O— $C_1$-$C_6$ alkyl" refers to a $C_1$-$C_6$ alkyl group as defined herein wherein one of the hydrogens is replaced by an oxygen substituent which replacement can be at any site on the alkyl chain, wherein the oxygen substituent is attached to a further $C_1$-$C_6$ alkyl group as defined herein, and includes methoxymethyl, ethoxymethyl, propoxymethyl, isopropoxymethyl, tert-butoxymethyl, pentoxymethyl, methoxyethyl, ethoxyethyl, propoxyethyl, isopropoxyethyl, tert-butoxyethyl and pentoxyethyl. Preferred $C_1$-$C_6$ alkyl-O— $C_1$-$C_6$ alkyl groups include methoxymethyl, ethoxymethyl, methoxyethyl and ethoxyethyl.

As used herein, the term "$C_3$-$C_6$ cycloalkyl" means a monovalent unsubstituted saturated cyclic hydrocarbon radical having from 3 to 6 carbon atoms and includes cyclopropyl, cyclobutyl, cyclohexyl and cyclopentyl. Preferred $C_3$-$C_6$ cycloalkyl are cyclopropyl and cyclohexyl.

As used herein the term "$C_1$-$C_6$ alkyl-$C_3$-$C_6$ cycloalkyl" refers to a $C_1$-$C_6$ alkyl group as defined herein wherein one of the hydrogens is replaced by a $C_3$-$C_6$ cycloalkyl substituent as defined herein, which replacement can be at any site on the alkyl chain. The term $C_1$-$C_6$ alkyl-$C_3$-$C_6$ cycloalkyl includes cyclopropylmethyl, cyclopropylethyl, cylopropylpropyl, 1-cyclopropylethyl, 1-cyclopropyl-1-methyl-ethyl, cyclopentylmethyl, cyclopentylethyl, cylopentylpropyl, 1-cyclopentylethyl, 1-cyclopentyl-1-methyl-ethyl, cyclohexylmethyl, cyclohexylethyl, cylohexylpropyl, 1-cyclohexylethyl and 1-cyclohexyl-1-methyl-ethyl. Preferred $C_1$-$C_6$ alkyl-$C_3$-$C_6$ cycloalkyl groups include cyclopropylmethyl, cyclopropylethyl and 1-cyclopropyl-1-methyl-ethyl.

As used herein, the term "aryl" refers to a mono- or polycyclic aromatic ring system and includes phenyl, 1-naphthyl and 2-naphthyl. Preferred aryl group is phenyl.

As used herein, the term "$C_1$-$C_4$ alkylaryl" refers to a $C_1$-$C_4$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_4$ alkylaryl include benzyl, 1-methyl benzyl and 1,1-dimethyl benzyl.

As used herein, the term "$C_1$-$C_6$ alkylaryl" refers to a $C_1$-$C_6$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_6$ alkylaryl include benzyl, 1-methyl benzyl and 1,1-dimethyl benzyl.

As used herein the term "heteroaryl" includes both monocyclic and bicyclic aromatic groups and includes 5-6-membered heteroaryl and 8-10-membered bicyclic heteroaryl.

As used herein, the term "5-6-membered heteroaryl" means a monocyclic aromatic group with a total of 5 or 6 atoms in the ring wherein from 1 to 4 of those atoms are each independently selected from N, O and S. Preferred groups have 1, 2 or 3 atoms in the ring which are each independently selected from N, O and S. Examples of 5-membered heteroaryl groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered heteroaryl groups include pyridinyl, pyrimidyl, pyrazinyl, pyridazinyl and triazinyl.

"Pyrrolyl" as used herein includes pyrrol-1-yl, pyrrol-2-yl and pyrrol-3-yl.

"Furanyl" (also called "furyl") as used herein includes furan-2-yl and furan-3-yl (also called 2-furyl and 3-furyl). Furan-2-yl is preferred.

"Thienyl" (also called "thiophenyl") as used herein includes thien-2-yl and thien-3-yl (also called 2-thiophenyl and 3-thiophenyl).

"Pyrazolyl" as used herein includes pyrazol-1-yl, pyrazol-3-yl, pyrazol-4-yl and pyrazol-5-yl (also called 1-pyrazole, 3-pyrazole, 4-pyrazole and 5-pyrazole). Pyrazol-1-yl is preferred.

"Imidazolyl" as used herein includes imidazol-1-yl, imidazol-2-yl, imidazol-4-yl and imidazol-5-yl. Imidazol-1-yl and imidazol-2-yl are preferred.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl (also called 2-thiazolyl, 4-thiazolyl and 5-thiazolyl).

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-2-yl, 1,2,3-triazol-4-yl, 1,2,3-triazol-5-yl, 1,2,4-triazol-1-yl, 1,2,4-triazol-3-yl and 1,2,4-triazol-5-yl. 1,2,3-triazol-1-yl, 1,2,3-triazol-2-yl and 1,2,4-triazol-1-yl are preferred.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" (also called "pyridyl") as used herein includes pyridin-2-yl, pyridin-3-yl and pyridin-4-yl (also called 2-pyridyl, 3-pyridyl and 4-pyridyl).

"Pyrimidyl" as used herein includes pyrimid-2-yl, pyrimid-4-yl, pyrimid-5-yl and pyrimid-6-yl.

"Pyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

As used herein, the term "8-10-membered bicyclic heteroaryl" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaryl groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaryl groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaryl groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" (also called "benzothiophenyl") as used herein includes benzothien-2-yl, benzothien-3-yl, benzothien-4-yl, benzothien-5-yl, benzothien-6-yl and benzothien-7-yl (also called 2-benzo[b]thiophenyl, 3-benzo[b]thiophenyl, 4-benzo[b]thiophenyl, 5-benzo[b]thiophenyl, 6-benzo[b]thiophenyl and 7-benzo[b]thiophenyl).

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl. Indazol-1-yl is preferred.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl. Benzimidazol-1-yl is preferred "1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl. Benzotriazol-1-yl is preferred.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo [1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

As used herein, the term "$C_1$-$C_4$ alkylheteroaryl" refers to a $C_1$-$C_4$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_4$ alkylheteroaryl include thiophenylmethyl, thiophenylethyl, furanylmethyl, furanylethyl, imidazolylmethyl, imidazolylethyl, triazolylmethyl and triazolylethyl.

As used herein, the term "$C_1$-$C_6$ alkylheteroaryl" refers to a $C_1$-$C_6$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_6$ alkylheteroaryl include thiophenylmethyl, thiophenylethyl, furanylmethyl, furanylethyl, imidazolylmethyl, imidazolylethyl, triazolylmethyl and triazolylethyl.

As used herein the term "carbocyclic ring" refers to a hydrocarbon ring fused to the pyridine substituent to which R6, R7 and R8 are attached, having from 5 to 8 carbon atoms and preferably 5 or 6 carbon atoms.

As used herein the term "5-8 membered carbocyclic ring" include cyclopentenyl, cyclohexenyl, phenyl, cycloheptenyl and cyclooctenyl. Preferable carbocyclic rings have from 5 to 6 carbon atoms, such as cyclopentene, cyclohexene and phenyl.

As used herein the term "heterocycle" refers to a saturated ring having from 4 to 8 atoms and preferably 5 or 6 atoms which incorporate the N atom of R9, optionally having one or two additional heteroatoms selected from oxygen, sulfur and nitrogen, the remaining atoms being carbon.

As used herein the term "4-8 membered heterocycle" include azetidine, pyrolidine, piperidine, piperizine, morpholine and thiomorpholine.

The compounds of the present invention may be chiral, and it is intended that any enantiomers, as separated, pure or partially purified enantiomers or racemic mixtures thereof are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The compounds of formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee=(\% E1)-(\% E2)$$

wherein E1 is the amount of the first enantiomer and E2 is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee o greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "Enantiomers. Racemates, and Resolutions," John Wiley and Sons, Inc., 1981, and E. L. Eliel and S. H. Wilen, "Stereochemistry of Organic Compounds," (Wiley-Interscience 1994). Examples of resolutions include recrystallization techniques or chiral chromatography.

Formula I, Ia, Ib and Ic show the structure of the compounds of the present invention without preferred stereochemistry. Preferred stereochemistry of the compounds of the present invention are indicated by the compounds of formula II, Ia, IIb and IIc.

Preferred compounds of the present invention include
2-[(2S,3R)-3-Amino-2-hydroxy-4-(2-methoxy-phenyl)-butyl]-N-tert-butyl-nicotinamide;
2-[(2R,3R)-3-Amino-4-(2,5-difluoro-phenyl)-2-hydroxy-butyl]-N-tert-but yl-6-trifluoromethyl-nicotinamide;
2-[(2S,3R)-3-Amino-2-hydroxy-4-(3-trifluoromethyl-phenyl)-butyl]-N-tert-butyl-nicotinamide;
2-[(2S,3R)-3-Amino-4-(3,5-difluoro-phenyl)-2-hydroxy-butyl]-N-tert-butyl-nicotinamide;
2-[(2S,3R)-3-Amino-4-(4-fluoro-phenyl)-2-hydroxy-butyl]-N-tert-butyl-nicotinamide;
2-(3-Amino-2-hydroxy-4-pyridin-2-yl-butyl)-N-tert-butyl-nicotinamide;
2-[(2S,3R)-3-Amino-4-(4-chloro-2,5-difluoro-phenyl)-2-hydroxy-butyl]-N-tert-butyl nicotinamide;
2-[(2S,3R)-3-Amino-4-(4-chloro-2,5-difluoro-phenyl)-2-hydroxy-butyl]-N-tert-butyl-nicotinamide;
N-{2-[(2S,3R)-3-Amino-4-(2,5-difluoro-phenyl)-2-hydroxy-butyl]-pyridin-3-yl}-acetamide;
2-[(2S,3R)-3-Amino-4-(2-fluoro-phenyl)-2-hydroxy-butyl]-N-tert-butyl-6-trifluoromethyl-nicotinamide;
2-[3-Amino-2-hydroxy-4-(4-methyl-pyridin-2-yl)-butyl]-N-tert-butyl-nicotinamide;
2-[(2S,3R)-3-Amino-4-(2-ethyl-phenyl)-2-hydroxy-butyl]-N-tert-butyl-nicotinamide;
2-[(2R,3S)-3-Amino-4-(2-chloro-5-methyl-phenyl)-2-hydroxy-butyl]-N-tert-butyl-nicotinamide;
2-[(2S,3R)-3-Amino-4-(2,6-difluoro-phenyl)-2-hydroxy-butyl]-N-tert-butyl-nicotinamide;
2-[(2S,3R)-3-Amino-2-hydroxy-4-(2-trifluoromethyl-phenyl)-butyl]-N-tert-butyl-nicotinamide;
2-[(2S,3R)-3-Amino-4-(2-fluoro-phenyl)-2-hydroxy-butyl]-N—((S)-1-phenyl-ethyl)-nicotinamide;
2-[(2S,3R)-3-Amino-4-(2-fluoro-phenyl)-2-hydroxy-butyl]-N-(4-methoxy-benzyl)-nicotinamide;
2-[(2S,3R)-3-Amino-4-(2-fluoro-phenyl)-2-hydroxy-butyl]-N-(3-methoxy-benzyl)-nicotinamide;
2-[(2S,3R)-3-Amino-4-(2,4-dichloro-5-fluoro-phenyl)-2-hydroxy-butyl]-N-tert-butyl-nicotinamide;
2-[(2S,3R)-3-Amino-4-(2-chloro-5-fluoro-phenyl)-2-hydroxy-butyl]-N-tert-butyl-nicotinamide;
2-[(2S,3R)-3-Amino-4-(2-fluoro-phenyl)-2-hydroxy-butyl]-N-benzyl-nicotinamide;
2-[(2S,3R)-3-Amino-4-(3-fluoro-phenyl)-2-hydroxy-butyl]-N-tert-butyl-nicotinamide;
2-[(2S,3R)-3-Amino-4-(3-fluoro-phenyl)-2-hydroxy-butyl]-N-tert-butyl-nicotinamide;
2-[(2S,3R)-3-Amino-4-(5-fluoro-2-trifluoromethyl-phenyl)-2-hydroxy-butyl]-N-tert-butyl-nicotinamide;
2-[(2S,3R)-3-Amino-4-(3,4-difluoro-phenyl)-2-hydroxy-butyl]-N-tert-butyl-nicotinamide;
(2S,3R)-3-Amino-4-(2-fluoro-phenyl)-1-pyridin-2-yl-butan-2-ol;
(2S,3R)-3-Amino-4-(2,5-difluoro-phenyl)-1-pyridin-2-yl-butan-2-ol;
2-[(2S,3R)-3-Amino-2-hydroxy-4-(4-methyl-pyridin-2-yl)-butyl]-N-tert-butyl-nicotinamide;
2-[(2S,3R)-3-Amino-4-(2-fluoro-phenyl)-2-hydroxy-butyl]-N-cyclopropylmethyl-nicotinamide;
2-[(2S,3R)-3-Amino-4-(2-fluoro-phenyl)-2-hydroxy-butyl]-N-cyclopropyl-nicotinamide;
2-[(2S,3R)-3-Amino-4-(2-chloro-5-methyl-phenyl)-2-hydroxy-butyl]-N-tert-butyl-nicotinamide;
2-[(2S,3R)-3-Amino-4-(2-fluoro-phenyl)-2-hydroxy-butyl]-N-(2,2,2-trifluoro-1,1-dimethyl-ethyl)-nicotinamide;
2-[(2S,3R)-3-Amino-4-(2-fluoro-phenyl)-2-hydroxy-butyl]-N-(1-cyclopropyl-1-methyl-ethyl)-nicotinamide;
2-[(2S,3R)-3-Amino-4-(2-fluoro-phenyl)-2-hydroxy-butyl]-N—((S)-2,2,2-trifluoro-1-methyl-ethyl)-nicotinamide;
2-[(2S,3R)-3-Amino-2-hydroxy-4-(2,4,5-trifluoro-phenyl)-butyl]-N-tert-butyl-6-trifluoromethyl-nicotinamide;
2-[(2S,3R)-3-Amino-4-(2-chloro-4,5-difluoro-phenyl)-2-methoxy-butyl]-N-tert-butyl-nicotinamide;
2-[(2S,3R)-3-Amino-4-(2-cyano-phenyl)-2-hydroxy-butyl]-N-tert-butyl-nicotinamide;
2-[(2S,3R)-3-Amino-4-(4,5-difluoro-2-methyl-phenyl)-2-hydroxy-butyl]-N-tert-butyl-nicotinamide;
2-[(2S,3R)-3-Amino-4-(2-chloro-4,5-difluoro-phenyl)-2-hydroxy-butyl]-N-tert-butyl-nicotinamide;
2-[(2S,3R)-3-Amino-4-(2-chloro-5-methyl-phenyl)-2-hydroxy-butyl]-N-tert-butyl-nicotinamide;

2-[(S)-3-Amino-4-(2,5-difluoro-phenyl)-butyl]-N-tert-butyl-nicotinamide;
2-[(2S,3R)-3-Amino-4-(4-fluoro-2-methyl-phenyl)-2-hydroxy-butyl]-N-tert-butyl-nicotinamide;
2-[(2S,3R)-3-Amino-4-(2,4-difluoro-phenyl)-2-hydroxy-butyl]-N-tert-butyl-nicotinamide;
2-[(2S,3R)-3-Amino-4-(5-fluoro-2-methyl-phenyl)-2-hydroxy-butyl]-N-tert-butyl-nicotinamide;
2-[(2S,3R)-3-Amino-4-(2,4-difluoro-phenyl)-2-hydroxy-butyl]-N-tert-butyl-nicotinamide;
2-[(E)-(2S,3R)-3-Amino-6-fluoro-2-hydroxy-5-((Z)-propenyl)-octa-5,7-dienyl]-N—((R)-1-phenyl-ethyl)-nicotinamide;
2-[(2S,3R)-3-Amino-4-(2,5-dichloro-phenyl)-2-hydroxy-butyl]-N-tert-butyl-nicotinamide;
2-[(2S,3R)-3-Amino-4-(5-chloro-2-fluoro-phenyl)-2-hydroxy-butyl]-N-tert-butyl-6-trifluoromethyl-nicotinamide;
2-[(2S,3R)-3-Amino-4-(5-chloro-2,4-difluoro-phenyl)-2-hydroxy-butyl]-N-tert-butyl-nicotinamide;
2-[(2S,3R)-3-Amino-4-(2-fluoro-5-methyl-phenyl)-2-hydroxy-butyl]-N-tert-butyl-nicotinamide;
2-[(2S,3R)-3-Amino-2-hydroxy-4-(2,4,5-trifluoro-phenyl)-butyl]-N-tert-butyl-nicotinamide;
2-[(2S,3R)-3-Amino-4-(2,5-difluoro-phenyl)-2-hydroxy-butyl]-N-tert-butyl-nicotinamide;
2-[(2S,3R)-3-Amino-4-(5-chloro-2,4-difluoro-phenyl)-2-methoxy-butyl]-N-tert-butyl-nicotinamide;
2-[(2S,3R)-3-Amino-4-(2-fluoro-5-methyl-phenyl)-2-hydroxy-butyl]-N-tert-butyl-nicotinamide;
2-[(2S,3R)-3-Amino-4-(2-chloro-5-fluoro-phenyl)-2-hydroxy-butyl]-N-tert-butyl-nicotinamide;
2-[(2S,3R)-3-Amino-4-(2,5-difluoro-phenyl)-2-hydroxy-butyl]-N-tert-butyl-nicotinamide;
2-[(2S,3R)-3-Amino-2-hydroxy-4-(2,4,5-trifluoro-phenyl)-butyl]-N-tert-butyl-nicotinamide;
or a pharmaceutically acceptable salt thereof.

Preferred compounds of the present invention include
2-[(2S,3R)-3-Amino-4-(5-chloro-2-fluoro-phenyl)-2-hydroxy-butyl]-N-tert-butyl-nicotinamide;
2-[(2S,3R)-3-Amino-4-(5-fluoro-2-chloro-phenyl)-2-hydroxy-butyl]-N-tert-butyl-nicotinamide;
2-[(2S,3R)-3-Amino-4-(2,5-dichloro-phenyl)-2-hydroxy-butyl]-N-tert-butyl-nicotinamide;
2-[(2S,3R)-3-Amino-4-(2-fluoro-5-trifluoromethyl-phenyl)-2-hydroxy-butyl]-N-tert-butyl-nicotinamide;
2-[(2S,3R)-3-Amino-4-(2,5-difluoro)-2-hydroxy-butyl]-N-tert-butyl-nicotinamide;
2-[(2S,3R)-3-Amino-4-(3,4-difluoro)-2-hydroxy-butyl]-N-tert-butyl-nicotinamide;
2-[(2S,3R)-3-Amino-4-(2,4,5-trifluoro)-2-hydroxy-butyl]-N-tert-butyl-nicotinamide;
2-[(2S,3R)-3-Amino-4-(2,5-dimethyl-phenyl)-2-hydroxy-butyl]-N-tert-butyl-nicotinamide;
2-[(2S,3R)-3-Amino-4-(4-chloro-2-fluoro-phenyl)-2-hydroxy-butyl]-N-tert-butyl-nicotinamide;
2-[(2S,3R)-3-Amino-4-(5-fluoro-2-trifluoromethylphenyl)-2-hydroxybutyl]-N-tert-butylnicotinamide;
2-[(2S,3R)-3-Amino-4-(2-fluoro-5-methylphenyl)-2-hydroxybutyl]-N-tert-butylnicotinamide;
2-((2S,3R)-3-Amino-2-hydroxy-4-m-tolyl-butyl)-N-tert-butyl-nicotinamide;
2-((2S,3R)-3-Amino-2-hydroxy-4-o-tolyl-butyl)-N-tert-butyl-nicotinamide;
2-[(2S,3R)-3-Amino-4-(4-chloro-phenyl)-2-hydroxy-butyl]-N-tert-butyl-nicotinamide;
2-((2S,3R)-3-Amino-2-hydroxy-4-pyridin-2-yl-butyl)-N-tert-butyl-nicotinamide;
2-[(2S,3R)-3-Amino-4-(2-fluoro-phenyl)-2-hydroxy-butyl]-N-methyl-nicotinamide;
2-[(2S,3R)-3-Amino-4-(2-fluoro-phenyl)-2-hydroxy-butyl]-N-(2,2,2-trifluoro-ethyl)-nicotinamide;
2-[(2S,3R)-3-Amino-4-(2-fluoro-phenyl)-2-hydroxy-butyl]-N-phenyl-nicotinamide;
2-[(2S,3R)-3-Amino-4-(2-fluoro-phenyl)-2-hydroxy-butyl]-N-phenethyl-nicotinamide;
2-[(2S,3R)-3-Amino-4-(2-fluoro-phenyl)-2-hydroxy-butyl]-N,N-dimethyl-nicotinamide;
{2-[(2S,3R)-3-Amino-4-(2-fluoro-phenyl)-2-hydroxy-butyl]-pyridin-3-yl}-piperidin-1-yl-methanone;
2-[(2S,3R)-3-Amino-4-(2-fluoro-phenyl)-2-hydroxy-butyl]-N-(2-methoxy-benzyl)-nicotinamide;
2-[(2S,3R)-3-Amino-4-(2-fluoro-phenyl)-2-hydroxy-butyl]-N-(1-methyl-1-phenyl-ethyl)-nicotinamide;
2-[(2S,3R)-3-Amino-4-(2-fluoro-phenyl)-2-hydroxy-butyl]-N-ethyl-nicotinamide;
2-[(S)-3-Amino-4-(2-fluoro-phenyl)-butyl]-N-tert-butyl-nicotinamide;
2-[(2S,3R)-3-Amino-4-(2,5-difluoro-phenyl)-2-hydroxy-butyl]-N-tert-butyl-6-trifluoromethyl-nicotinamide;
(2S,3R)-3-Amino-4-(2-fluoro-phenyl)-1-pyridin-2-yl-butan-2-ol;
2-[(2S,3R)-3-Amino-4-(2-fluoro-phenyl)-2-hydroxy-butyl]-N-tert-butyl-nicotinamide;
2-[(2S,3R)-3-Amino-4-(2-fluoro-phenyl)-2-methoxy-butyl]-N-tert-butyl-nicotinamide;
2-[(2S,3R)-3-Amino-4-(2-fluoro-phenyl)-2-hydroxy-butyl]-N-isopropyl-nicotinamide;
2-[(2S,3R)-3-Amino-4-(5-methyl-2-chloro-phenyl)-2-hydroxy-butyl]-N-tert-butyl-nicotinamide;
2-[(2S,3R)-3-Amino-4-(2,4-difluoro)-2-hydroxy-butyl]-N-tert-butyl-nicotinamide;
2-[(2S,3R)-3-Amino-4-(2-chloro-4-fluoro-phenyl)-2-hydroxy-butyl]-N-tert-butyl-nicotinamide;
2-[(2S,3R)-3-Amino-4-(2-methyl-5-fluoro-phenyl)-2-hydroxy-butyl]-N-tert-butyl-nicotinamide;
2-[(2S,3R)-3-Amino-4-(3-chloro-2-fluoro-phenyl)-2-hydroxy-butyl]-N-tert-butyl-nicotinamide;
{2-[(2S,3R)-3-Amino-4-(2-fluoro-phenyl)-2-hydroxy-butyl]-pyridin-3-yl}-pyrrolidin-1-yl-methanone;
2-[(2S,3R)-3-Amino-4-(3-trifluoromethyl-phenyl)-2-hydroxy-butyl]-N-tert-butyl-nicotinamide;
2-[(2S,3R)-3-Amino-4-(2-chloro-phenyl)-2-hydroxy-butyl]-N-tert-butyl-nicotinamide;
2-[(2S,3R)-3-Amino-4-(3-chloro-phenyl)-2-hydroxy-butyl]-N-tert-butyl-nicotinamide;
or a pharmaceutically acceptable salt thereof.

Further preferred compounds of the present invention include 2-[(2S,3R)-3-Amino-4-(5-chloro-2,4-difluoro-phenyl)-2-methoxy-butyl]-N-tert-butyl-nicotinamide Dihydrochloride;
2-[(2S,3R)-3-Amino-4-(2,5-difluoro-phenyl)-2-hydroxy-butyl]-N-tert-butyl-6-trifluoromethyl-nicotinamide Dihydrochloride;
2-[(2S,3R)-3-Amino-4-(5-chloro-2-fluoro-phenyl)-2-hydroxy-butyl]-N-tert-butyl-6-trifluoromethyl-nicotinamide Dihydrochloride;
2-[(2S,3R)-3-Amino-4-(5-chloro-2,4-difluoro-phenyl)-2-hydroxy-butyl]-N-tert-butyl-nicotinamide Dihydrochloride;
2-[(2S,3R)-3-Amino-4-(2-fluoro-5-methyl-phenyl)-2-hydroxy-butyl]-N-tert-butyl-nicotinamide Dihydrochloride;

2-[(2S,3R)-3-Amino-4-(2,5-difluoro-phenyl)-2-hydroxy-butyl]-N-tert-butyl-6-trifluoromethyl-nicotinamide Mesylate;

2-[(2S,3R)-3-Amino-2-hydroxy-4-(2,4,5-trifluoro-phenyl)-butyl]-N-tert-butyl-nicotinamide Dihydrochloride;

2-[(2S,3R)-3-Amino-4-(5-chloro-2-fluoro-phenyl)-2-hydroxy-butyl]-N-tert-butyl-nicotinamide Dihydrochloride;

2-[(2S,3R)-3-Amino-4-(2,5-difluoro-phenyl)-2-hydroxy-butyl]-N-tert-butyl-6-trifluoromethyl-nicotinamide Fumarate; and 2-[(2S,3R)-3-Amino-4-(2,5-difluoro-phenyl)-2-hydroxy-butyl]-N-tert-butyl-nicotinamide Dihydrochloride.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts," *J. Pharm. Sci.*, 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts. Typical pharmaceutical salts include those salts prepared by reaction of the compounds of formula I with an inorganic or organic acid. Such salts are known as acid addition salts. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts.

Preferred pharmaceutical acid addition salts are hydrochloric acid and the like.

The compounds of the present invention may form solvates with standard low molecular weight solvents using methods well known to the person skilled in the art. Such solvates are also contemplated as being within the scope of the present invention.

Figure 2:
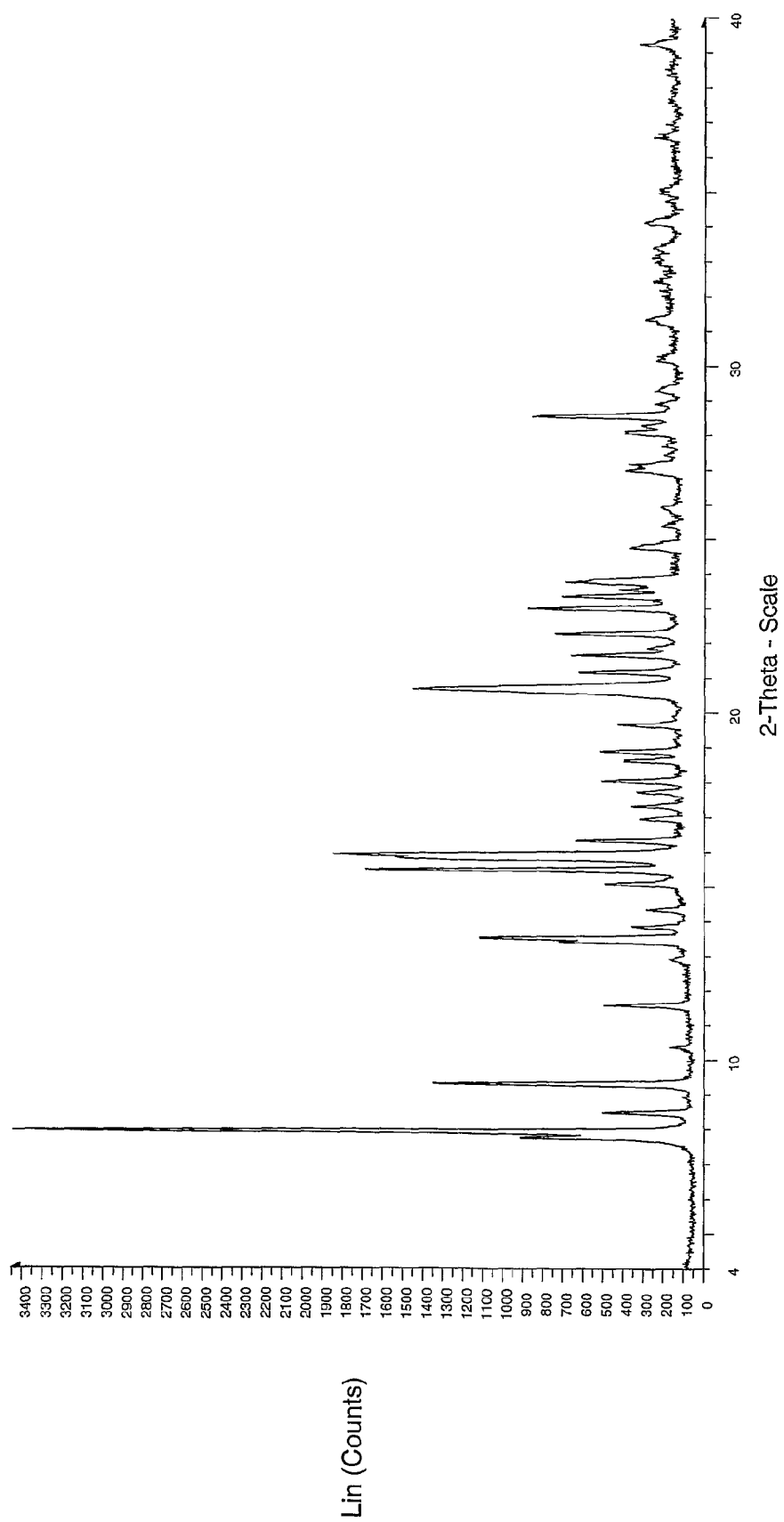
FIG. 2 (FIG. 2) illustrates an XRPD trace of 2-[(2S,3R)-3-Amino-4-(2,5-difluoro-phenyl)-2-hydroxy-butyl]-N-tert-butyl-6-trifluoromethyl-nicotinamide (Form II).

X-ray powder diffraction (XRPD) is a technique that detects long-range order in a crystalline material and was used to characterize Form I (see FIG. 1) and Form II (see FIG. 2). The angular peak positions in 2θ and corresponding intensity data (I) for Forms I and II are tabulated in Tables 1 and 2 respectively. All data in Tables 1 and 2 are expressed with an accuracy of ±0.2%

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that, for any given crystal form, the angular peak positions may vary slightly. For example, peak positions can shift due to a variation in the temperature at which a sample is analyzed, sample displacement, or the presence or absence of an internal standard. In the present case, a peak position variability of ±0.2 in 2θ will take into account these potential variations without hindering the unequivocal identification of Forms I and II.

A well known and accepted method for searching crystal forms in the literature is the "Fink' method. The Fink method uses the four most intense lines for the initial search followed by the next four most intense lines. In accord with the Fink method, based on peak intensities as well as peak position, Form I may be identified by the presence of peaks at 6.9±0.2, 8.8±0.2, 17.6±0.2, and 21.7±0.2 in 2θ; and further verified by peaks at 12.8±0.2, 20.8±0.2, and 23.5±0.20 in 2θ; when the pattern is obtained from a copper radiation source. Form II may be identified by the presence of peaks at 7.9±0.2, 15.5±0.2, 15.9±0.2, and 20.7±0.2 in 2θ; and further verified by peaks at 9.3±0.2, 13.5±0.2, and 28.5±0.20 in 2θ; when the pattern is obtained from a copper radiation source.

TABLE 1

(Form I)

| 2θ | I |
|---|---|
| 6.9 | 2506 |
| 8.8 | 3355 |
| 12.8 | 1954 |
| 17.6 | 4325 |
| 20.8 | 2364 |
| 21.7 | 2706 |
| 23.5 | 2096 |

TABLE 2

(Form II)

| 2θ | I |
|---|---|
| 7.9 | 3433 |
| 9.3 | 1315 |
| 13.5 | 1125 |
| 15.5 | 1679 |
| 15.9 | 1845 |
| 20.7 | 1431 |
| 28.5 | 827 |

The compounds of the present invention are useful in the treatment or prevention of the following conditions or diseases: hyperglycaemia, low glucose tolerance, insulin resistance, obesity, lipid disorders, dyslipidemia, hyperlipidemia, hypertriglyceridema, hypercholesterolemia, low HDL levels, high LDL levels, atherosclerosis and its sequelae, vascular restenosis, irritable bowel syndrome, inflammatory bowel disease, Crohn's disease, ulcerative colitis, other inflammatory conditions, pancreatitis, abdominal obesity, neurodegenerative disease, retinopathy, nephropathy, neuropathy, Syndrome X, polycystic ovarian syndrome, Type II diabetes, growth hormone deficiency, neutropenia, neuronal disorders, tumor metastasis, benign prostatic hypertrophy, hypertension, osteoporosis and other conditions that may be treated or prevented by inhibition of DPP-IV.

In a further aspect of the invention the present compounds are administered in combination with one or more further active substances. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations.

Thus, in a further aspect of the invention the present compounds may be administered in combination with one or more antidiabetics. Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1, GLP-1 mimetics and GLP-1 receptor agonists such as those disclosed in WO00/42026 and WO0059887, other DPP-IV inhibitors such as isoleucine thiazolidide (P32/98), NVP-DPP-728, LAF 237, P93/01, MK-0431 (Sitagliptin), and BMS 477118, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069

In another aspect of the invention, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix preparation comprising one or more of these.

In a further aspect of the invention the present compounds are administered in combination with a sulphonylurea such as glibenclamide, glipizide, tolbautamide, chloropamidem, tolazamide, glimepride, glicazide and glyburide.

In another aspect of the invention the present compounds are administered in combination with a biguanidine for example metformin.

In yet another aspect of the invention the present compounds are administered in combination with a meglitinide for example repaglinide or nateglinide.

In still another aspect of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another aspect of the invention the present compounds may be administered in combination with an insulin sensitizer for example such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further aspect of the invention the present compounds are administered in combination with an α-glucosidase inhibitor for example voglibose, emiglitate, miglitol or acarbose.

In another aspect of the invention the present compounds are administered in combination with an agent acting on the ATP-dependent potassium channel of the β-cells for example tolbutamide, glibenclamide, glipizide, glicazide, BTS-67582 or repaglinide.

In yet another aspect of the invention the present compounds may be administered in combination with nateglinide.

In still another aspect of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate oratorvastin.

In still another aspect of the invention the present compounds are administered in combination with compounds lowering food intake.

In another aspect of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further aspect of the invention the present compounds may be administered in combination with one or more antiobesity agents or appetite regulating agents. Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant).

In another aspect of the invention the antiobesity agent is dexamphetamine or amphetamine.

In another aspect of the invention the antiobesity agent is leptin.

In another aspect of the invention the antiobesity agent is fenfluramine or exfenfluramine.

In still another aspect of the invention the antiobesity agent is sibutramine.

In a further aspect of the invention the antiobesity agent is orlistat.

In another aspect of the invention the antiobesity agent is mazindol or phentermine.

In still another aspect of the invention the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolot, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of formula I can be prepared by one of ordinary skill in the art following a variety of procedures, some of which are illustrated in the procedures and schemes set forth below. The particular order of steps required to produce the compounds of formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "deprotection" of suitable protecting groups to be used by the skilled artisan.

The compounds of the present invention may be prepared as is shown in the following reaction schemes.

Scheme I

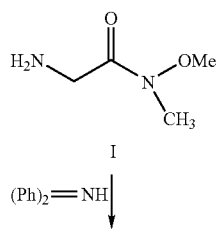

I (Ph)$_2$=NH

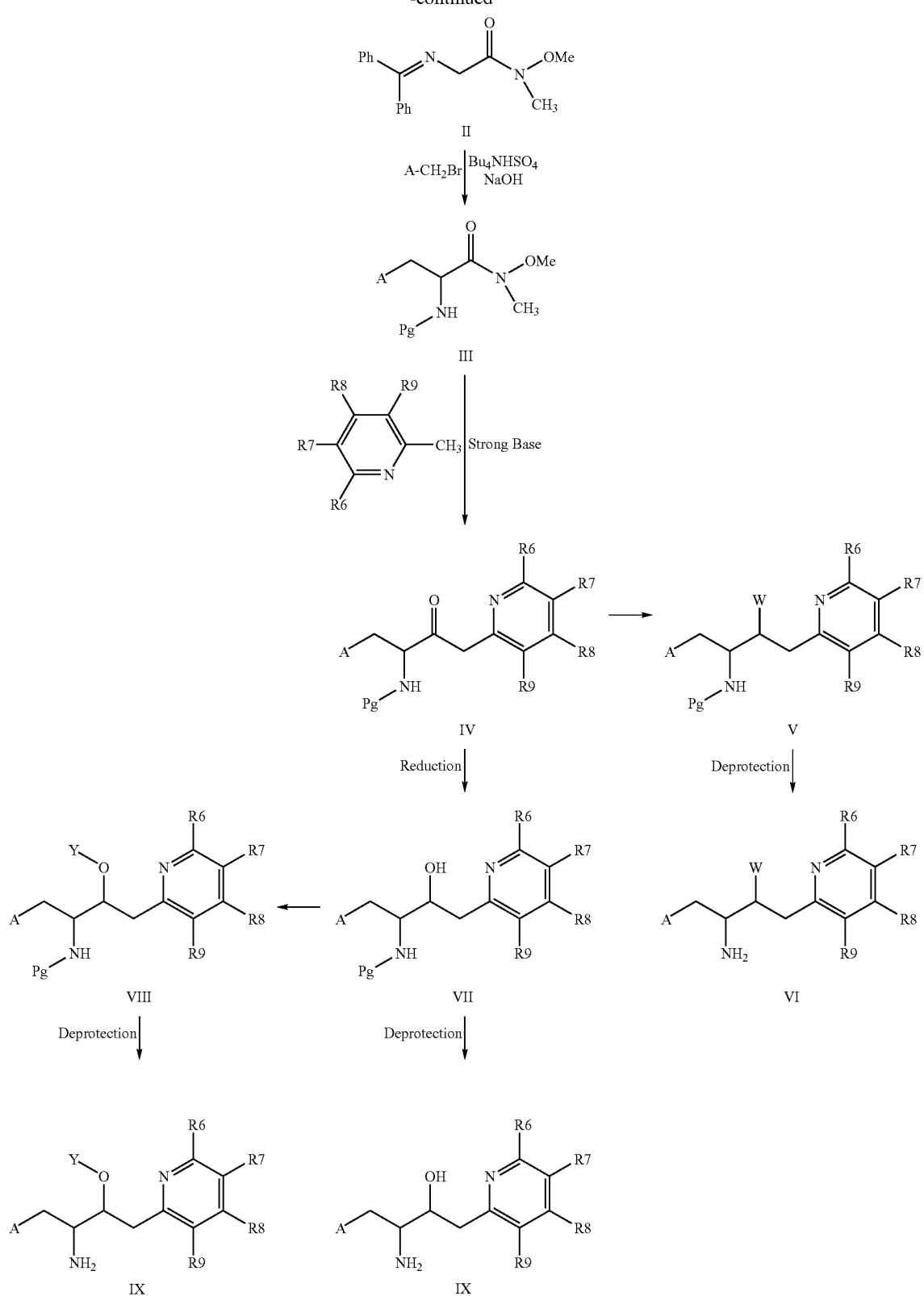
W = $C_1$-$C_6$ alkyl or $C_1$-$C_6$ fluoroalkyl
Y = $C_1$-$C_6$ alkyl or $C_3$-$C_6$ cycloalkyl
Pg = Protecting group The intermediate III of Scheme I is prepared according to the method described in Acc. Chem. Res. 2004, 37, 506-517.

The Weinreb amides as intermediate I of Scheme I and III* of Scheme II are prepared according to the method described in Tetrahedron Letters, 1981, vol 22, 3815.

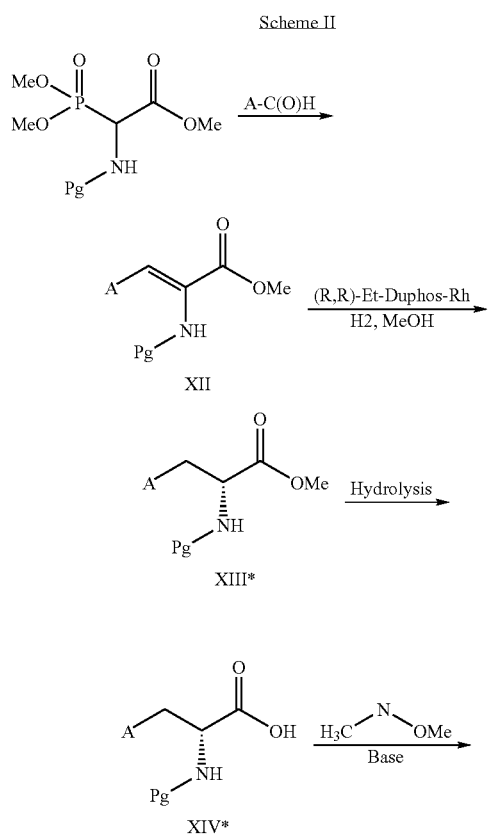

*-indicates chiral

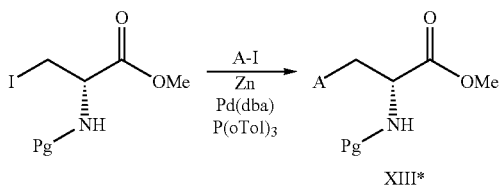

The intermediate XIII* of Scheme III is prepared according to the method described in Organic Syntheses, 2004, vol 81, 77-87.

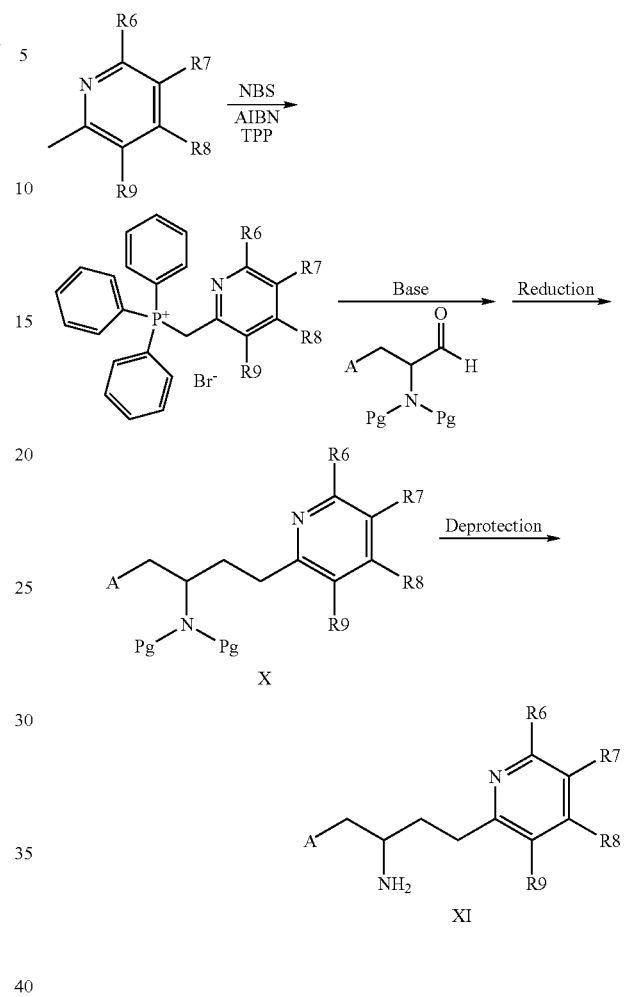

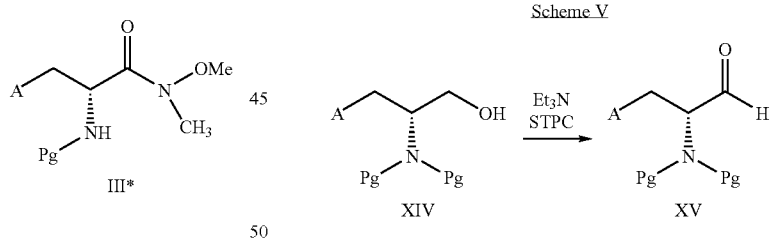

The intermediate XIV of Scheme V is prepared according to the method described in WO-95/14653

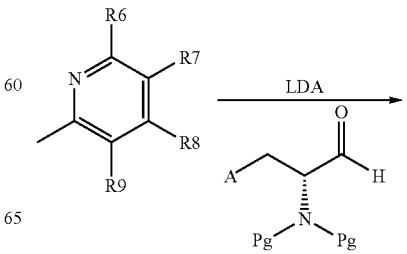

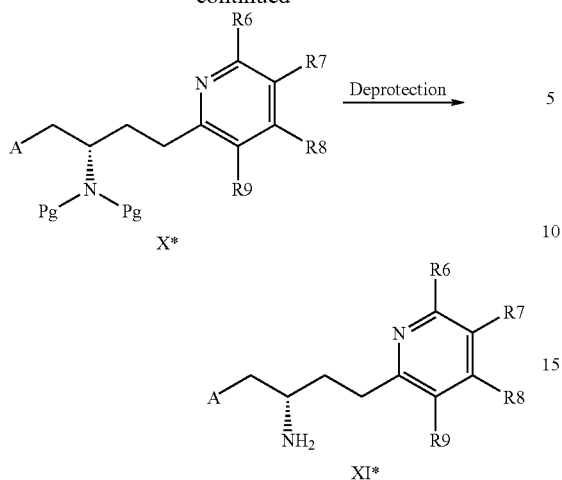

X*

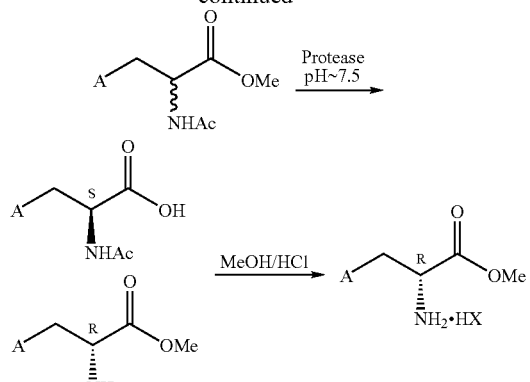

Scheme VII

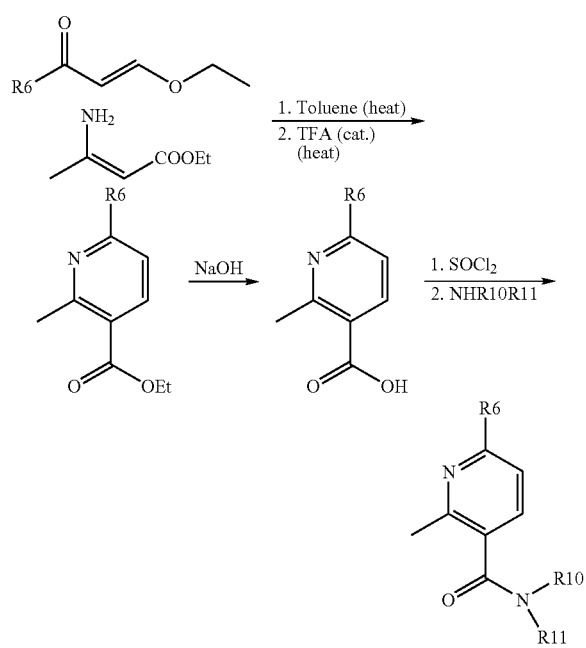

Scheme VIII

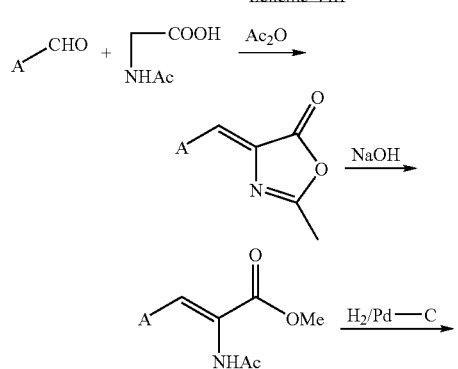

Experimental Section

Abbreviations used follow IUPAC-IUB nomenclature. Additional abbreviations are aq., aqueous; equiv, (molar) equivalent; HPLC, high-performance liquid chromatography; THF, tetrahydrofuran; HOAc, acetic acid; DMSO, dimethyl sulfoxide (perdeuterated if for NMR); EtOAc, ethyl acetate; EtOH, ethanol; MeOH, methanol; DMF, dimethylformamide; DBU, 1,8-diazabicyclo[5.4.0]undec-7-ene; HOBT, 1-hydroxy benzotriazole; EDCI, 1-(3-dimethylaminopropyl)-3-ethylcarbodiimide hydrochloride; LDA, lithium diisopropylamide; TMEDA, N,N,N',N'-tetramethylethylenediamine; AIBN, 2,2'-azobisisobutyronitrile; Boc, tertiary-butyloxy-carbonyl; Cbz, benzyloxy-carbonyl; MS, electrospray mass spectrum; TFA, trifluoroacetic acid; (R,R)-Et-DUPHOS-Rh, bis-((2R,5R)-2,5-diethylphospholano)-benzene-(cyclooctadiene)-rhodium(I) tetrafluoroborate or trifluoromethanesulfonate salt; MTBE, methyl tert-butyl ether; STPC, Sulfur Trioxide Pyridine Complex; DPP, Diphenylphosphine; NBS, N-Bromosuccinamide. All solution concentrations are expressed as % volume/% volume unless otherwise stated. Reagents were obtained from a variety of commercial sources. $^1$HNMR means a proton magnetic resonance spectrum was obtained.

General Reaction Procedures

General Procedure 1—Formation of Weinreb Amide:

To a solution of protected aminoacid (1 equiv), 1-hydroxy-benzotriazole (1.5 equiv), N,O-dimethylhydroxylamine hydrochloride (1.1 equiv) and N,N-diisopropylethylamine (3 equiv) in DMF (0.1-0.5M) is added 1-(3-dimethylaminopropyl)-3-ethylcarbodiimide hydrochloride (1.5 equiv) and the reaction is allowed to stir overnight. The reaction is quenched with saturated NaHCO$_3$ and the product is extracted into a suitable organic solvent. The combined organic layers are washed with brine, dried over magnesium sulfate or sodium sulfate, filtered and are concentrated under reduced pressure to afford a crude residue. Purification by silica gel flash column chromatography provides the product.

General Procedure 2—Addition of 2-methyl-pyridine Derivative to Weinreb Amides:

An oven-dried three-neck flask fitted with a thermometer, mechanical stirrer, and nitrogen inlet is charged with a 2-methyl-pyridine derivative (3 equiv) in THF (0.1-0.5M) and the flask is cooled to −78° C. To the solution is added sec-BuLi dropwise such that the internal temperature remains below −60° C. The reaction is then allowed to stir at −78° C. for an additional 1-3 hours. A solution of Weinreb amide (1 equiv) in THF (0.1-1M) is added dropwise to the reaction and the reaction is allowed to continue stirring at −78° C. for an additional 0.5-2 hours. The reaction is then quenched at −78°

C. by addition of either acetic acid or 2M NaHSO4 such that the resultant mixture is pH <7. The quenched reaction mixture is allowed to warm to room temperature and the product is extracted into a suitable organic solvent. The combined organic layers are washed with brine, dried over magnesium sulfate or sodium sulfate, filtered and are concentrated under reduced pressure to afford a crude residue. Purification by silica gel flash column chromatography provides the product.

General Procedure 3—Ketone Reduction:

To a solution of ketone (1 equiv) in absolute ethanol (0.1-0.5M) at 0° C. is added sodium borohydride (1-5 equiv) portion wise under a stream of nitrogen. The reaction is then allowed to warm to room temperature and is stirred for an additional 1-16 hours. The combined organic layers are washed with brine, dried over magnesium sulfate or sodium sulfate, filtered and are concentrated under reduced pressure to afford a crude residue. Purification by silica gel flash column chromatography provides the product.

General Procedure 4—Preparation of Alanine Derived Weinreb Amides from 2-(benzhydrylidene-amino)-N-methoxy-N-methyl-acetamide:

A round bottom flask equipped with stir bar is charged with a 0.24M solution of 2-(benzhydrylidene-amino)-N-methoxy-N-methyl-acetamide (1 equiv) in dichloromethane. The solution is concentrated under reduced pressure to approximately ½ volume then treated with 2.5 M aq. NaOH (6 equiv), Bu$_4$NHSO$_4$ (1.1 equiv) and Ar—CH$_2$Br (1.1 equiv). The reaction is stirred vigorously for 1-2 hours after which time the phases are separated and the aqueous phase is back extracted with methylene chloride. The organic phases are then combined and concentrated under reduced pressure. The resultant crude residue is diluted with diethyl ether (1-1.5M) and 1 N aq. HCl (0.3-1 M). The biphasic reaction is stirred vigorously for 2 hours after which time the ether layer is discarded and the aqueous phase is adjusted by dropwise addition of 5 N NaOH to pH 9. A 1M solution of Boc-anhydride in THF (1.5 equiv) is added by syringe and the reaction is stirred overnight. The reaction is then extracted with a suitable organic solvent. The combined organic layers are washed with brine, dried over magnesium sulfate or sodium sulfate, filtered and are concentrated under reduced pressure to afford a crude residue. Purification by silica gel flash column chromatography provides the product.

General Procedure 5—Amide Coupling:

To a solution of carboxylic acid (1 equiv) in DMF (0.1-0.3M) is added an amine (5 equiv), benzotriazole-1-yl-oxy-tris-pyrrolidino-phosphonium hexafluorophosphate (1.2 equiv), and diisopropylethylamine (8-10 equiv). The reaction is allowed to stir at room temperature after which time it is poured into water and is extracted with ether. The combined organic layers are washed with brine, dried over magnesium sulfate or sodium sulfate, filtered and are concentrated under reduced pressure to afford a crude residue. Purification by silica gel flash column chromatography provides the product.

General Procedure 6—Preparation of Enantiomerically Enriched Alanine Derivatives.

To a slurry of (R)-benzyloxycarbonylamino-(dimethoxyphosphoryl)-acetic acid methyl ester (1.06 equiv) in dichloromethane (1-3M) at 0° C. is slowly added DBU (1.1 equiv). The resultant solution is then allowed to stir at room temperature for 30 minutes after which time it is recooled to 0° C. A solution of the appropriately substituted aldehyde (1 equiv) in dichloromethane (2-5M) is then slowly added to the solution after which time the reaction is allowed to warm and stir at room temperature for 4 hours. The reaction is then poured into an ice-chilled solution of 1N aqueous H$_2$SO$_4$ and then diluted with EtOAc. The organic layer is washed with water and brine, dried over magnesium sulfate or sodium sulfate, filtered and is concentrated under reduced pressure to afford a crude residue. Purification by silica gel flash column chromatography provides the Horner Emmons product. This product (1 equiv) is then dissolved in methanol (0.2-0.5 M) and bis-((2R,5R)-2,5-diethylphospholano)-benzene-(cyclooctadiene)-rhodium(I) tetrafluoroborate or trifluoromethanesulfonate salt (0.002-0.1 equiv) is added. The mixture is then stirred at room temperature under hydrogen at 50-100 psi for 4-24 hours after which time the flask is vented and the reaction is filtered through a pad of Celite®. Concentration of the filtrate gives the product.

General Procedure 7—Ester Hydrolysis.

To a solution of ester (1 equiv) in a solution of 2:1 dioxane:water (0.1-0.5 M) is added lithium hydroxide (1-10 equiv). After stirring for 1-24 hours, water is added and the solution is adjusted to pH 5-6 by addition of an aqueous protic acid. The product is then extracted into a suitable organic solvent which is then dried over sodium or magnesium sulfate, is filtered, and is concentrated under reduced pressure to give the product.

General Procedure 8—Aldehyde Synthesis.

To a solution of Intermediate XIV in DMSO and Triethylamine (3-6 equiv) at −9° C. is added a solution of Sulfur Trioxide Pyridine Complex (2 equiv) in DMSO over a period of 20-90 min. The reaction is allowed to stir an additional 5-30 min at ~0° C., after which the reaction is quenched by addition of water over a period of 30-90 min, the reaction temperature is maintained below 10° C. The product is then extracted into a suitable organic solvent which is then dried over sodium or magnesium sulfate, filtered, and concentrated under reduced pressure to give the product.

General Procedure 9—Addition of 2-methyl-pyridine Derivative to Aldehydes:

To a solution of Diisopropylamine (2-3 equiv) in THF (22.0 mL) at −78° C. is added Butyl Lithium (2-3 equiv) dropwise over 10-40 minutes. The resulting solution is stirred at −78° C. for 30 minutes after which a solution of 2-methyl-pyridine derivative and Tetramethylenediamine (2-3 equiv) in THF is added dropwise over 30-90 min, the resulting solution is stirred for 30-90 min. To the reaction is added a solution of Intermediate XV (0.9-1.5 equiv) in anhydrous THF over 1-3 hours. The reaction is allowed to warm after which the reaction is quenched by addition of water. The pH is adjusted to ~9 and the product is extracted into a suitable organic solvent which is dried over sodium or magnesium sulfate, filtered, and concentrated under reduced pressure to give the product.

General Procedure 10—Synthesis of 2-Methyl-nicotinic acid ethyl ester Derivatives To a solution of ethyl-3-aminocrotonate (1 equiv) in toluene is added an acetyl-vinyl ethyl ether derivative (1 equiv). The reaction is heated to ~50° C. for 10-30 min then refluxed for 1-3 hr using Dean Stark apparatus. The reaction is allowed to cool to RT, and the product extracted into a suitable organic solvent which is dried over sodium or magnesium sulfate, filtered, and concentrated under reduced pressure to give the product.

General Procedure 11—Protease Resolution

To an amino acid ester derivative in pH 7.2 phosphate buffer (0.2M) is added the protease (for example Sigma protease *Bucillus* sp). The reaction is stirred at room temperature for 17-120 hrs. Hydrochloric acid (6N) is added and extracted with ethyl acetate. The combined organic phases were washed with 5% Na$_2$CO$_3$ and water. The organic phase is dried over sodium or magnesium sulfate, filtered, and concentrated under reduced pressure to give the product(R-enantiomer).

The combined aqueous is washed using MTBE and acidified using 6N HCl to pH<2.0, and extracted with ethyl acetate. The organic phase is dried over sodium or magnesium sulfate, filtered, and concentrated under reduced pressure to give the product(S-enantiomer).

General Deprotection Procedure 1:

Into a solution of Boc-protected amine in a suitable non-protic organic solvent (0.01-0.5M) at 0° C.-room temperature is bubbled HCl gas for 5-15 minutes. Removal of the solvent under reduced pressure provides the product.

General Deprotection Procedure 2:

To a solution of cbz-protected amine in EtOH (0.1-0.5M) is added Pd/C (0.1-1 equiv) and the mixture is shaken under hydrogen at 60 psi for 2-24 hours.

General Deprotection Procedure 3:

To a solution of Boc-protected amine in dichloromethane (0.1-1M) is added trifluoroacetic acid. The reactions are stirred for 1-20 hrs after which time the reactions are concentrated under reduced pressure. Saturated NaHCO3 is added and the product is extracted into dichloromethane. The combined organic phases are concentrated under reduced pressure and excess of a 1N solution of HCL in ether or ethyl acetate is added and the product is isolated by centrifugation.

General Deprotection Procedure 4:

To the starting Boc-protected amine is added an excess amount of a 5% solution of trifluoroacetic acid in dichloromethane. The reaction is stirred for 10-20 hr after which time the reaction mixture is either concentrated under reduced pressure or is added to saturated NaHCO3 and is extracted into dichloromethane which is then concentrated to provide a crude residue.

General Deprotection Procedure 5:

To the starting Boc-protected amine is added an excess amount of a 1N solution of HCl in dioxane. The reaction is stirred for 1-5 hr after which time the reaction mixture is concentrated under reduced pressure to provide a crude residue.

General Deprotection Procedure 6:

To water wet 10% Pd/C (0.05-1 equiv) is added a solution of cbz-protected amine in MeOH (0.1-0.5M). To the reaction is added a solution of Formic Acid Ammonium Salt (2-6 equiv) in water and heated to 40° C. for 1-5 hr after which time the reaction mixture is concentrated under reduced pressure to provide a crude residue.

General Purification Methods

Purification Method 1:

The crude product is purified by preparative HPLC on an Xterra® RP18 (30×300 mm) column at 30° C. and a flow of 10 ml/min. The elution system is or consists of an isocratic gradient of 10:90 (acetonitrile: (0.1% HCl in H$_2$O)) for 1-5 min followed by a linear gradient from 10:90 (acetonitrile: (0.1% HCl in H$_2$O)) to 30:70 (acetonitrile: (0.1% HCl in H$_2$O)) over 20 min. The fractions are concentrated to give the purified compound.

Purification Method 2:

The crude product is purified by preparative HPLC on an Xterra® RP18 (30×300 mm) column at 30° C. and a flow of 10 ml/min. The elution system is or consists of an isocratic gradient of 0:100 (acetonitrile: (0.1% HCl in H$_2$O)) for 1-5 min followed by a linear gradient from 0:100 (acetonitrile: (0.1% HCl in H$_2$O)) to 70:30 (acetonitrile: (0.1% HCl in H$_2$O)) over 25 min. The fractions are concentrated to give the purified compound.

Purification Method 3:

The product is purified by HPLC chiral separation (Column: 46×15 cm chiralpak AD-H; Eluent: 10:90:0.2 (isopropyl alcohol:heptanes:dimethylethylamine); Flow: 0.6 mL/min at UV 279 nm) affords enantiomerically enriched compound. The fractions are concentrated under reduced pressure and the resultant residue is treated with excess of a 0.1-2N solution of HCl in an appropriate solvent. Filtration or concentration gives the compound as the HCl salt.

Preparation of Common Intermediates

Intermediate 1

2-Amino-N-methoxy-N-methyl-acetamide hydrochloride

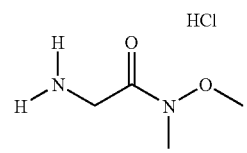

A 500 mL round bottom flask equipped with a magnetic stirrer, serum cap and a needle gas bleed is charged with [(methoxy-methyl-carbamoyl)-methyl]-carbamic acid tert-butyl ester (9.6 g, 44 mmol) and 100 mL ethyl acetate. HCl (4M in p-dioxane, 100 mL) is added via cannula and the reaction mixture is stirred at ambient temperature for 3 hr. Removal of the solvent under reduced pressure provides the title compound which can be used without further purification.

Intermediate 2

2-(Benzhydrylidene-amino)-N-methoxy-N-methyl-acetamide

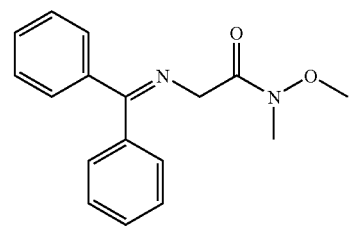

2-Amino-N-methoxy-N-methyl-acetamide; hydrochloride is dissolved in 80 mL methylene chloride and a solution of benzhydrylideneamine (8.2 g, 44 mmol) in 40 mL methylene chloride is added dropwise with vigorous stirring. The reaction mixture is stirred overnight, filtered through Hyflo SuperCel and allowed to stand overnight. Additional precipitated ammonium chloride is removed by filtration through Hyflo SuperCel. The filtrate is then dissolved in methylene chloride to make a 0.22M solution and the solution containing the title compound is used without further purification.

$^1$HNMR (400 MHz, CDCl$_3$) δ 3.19 (s, 3H), 3.62 (s, 3H), 4.37 (s, 2H), 7.22-7.68 (m, 10H)

Intermediate 3

N-tert-Butyl-2-methyl-nicotinamide

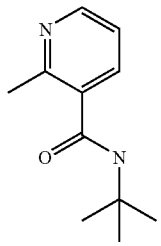

A 12-L, three-neck, round-bottom flask equipped with a mechanical stirrer, a thermocouple, and a nitrogen inlet gas adapter is charged with 2-methyl nicotinic acid (302 g, 2.2 mol), EDCI (464 g, 2.4 mol), HOBt (327.3 g, 2.4 mol, 1.1 equiv) and 4.5 L of anhydrous acetonitrile. The mixture is stirred for 45 minutes at room temperature to dissolve most of the solids and is then cooled to 5° C. using an ice-water bath. A mixture of t-butylamine (242 mL, 2.5 mol) and Hunig's base (402 mL, 2.5 mol) in 500 mL of anhydrous acetonitrile and 500 mL of anhydrous dichloromethane is added slowly over 45 minutes, maintaining the temperature below 10° C. The mixture is stirred for 15 hours at room temperature under nitrogen. The solvent is removed under reduced pressure and the residue is dissolved in ethyl acetate (3.0 L) then washed with saturated ammonium chloride solution (2.0 L). The organic-phase is dried over magnesium sulfate, filtered, and concentrated under reduced pressure. Purification of the resultant crude residue by silica gel flash column chromatography followed by trituration with 5% ethyl acetate/heptane gives the title compound.

$^1$H NMR

MS (m/e): 193 (M+1)

Intermediate 4

N-tert-Butyl-2-methyl-6-trifluoromethyl-nicotinamide

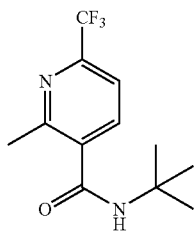

N-tert-Butyl-2-methyl-6-trifluoromethyl-nicotinic acid (5.0 g, 24 mmol) is refluxed in 10 mL of thionyl chloride for 3 h and is then concentrated under reduced pressure. The residue is dissolved in toluene and the solvent is removed under reduced pressure. The residue is again dissolved in toluene and the solvent is removed under reduced pressure. The resultant residue is dissolved in 50 mL of dichloromethane and to the solution is added tert-butyl amine (3.8 mL, 49 mmol) and triethylamine (6.8 mL, 49 mmol) and the reaction is allowed to stir overnight. The reaction is then poured into sat. ammonium chloride and extracted three times with dichloromethane. The combined organic phases are then washed with sat. NaHCO$_3$, and brine. The organic layer is then dried over sodium sulfate, filtered, and concentrated under reduced pressure to afford the title compound. Further purification is achieved by trituration from diethyl ether.

$^1$HNMR

MS (m/e): 261 (M+1)

Intermediate 5

2-Fluoro-5-methylbenzyl alcohol

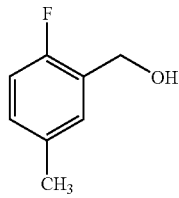

To a 1M solution of lithium aluminum hydride in THF (57 mL) at 0° C. is added a solution of 2-fluoro-5-methylbenzoic acid (8.0 g, 52 mmol) in 160 mL of ether drop-wise. The reaction is then heated at reflux for 1.5 hr. The reaction is then cooled to 0° C. and is quenched with H$_2$O (4 mL), aqueous 40% NaOH (4 mL) and H$_2$O (4 mL). The resultant slurry is then filtered through celite and MgSO$_4$. The filtrate is then concentrated and purified by silica gel flash column chromatography to provide the title compound.

$^1$HNMR (400 MHz, CDCl$_3$) δ 2.36 (s, 3H), 4.78 (s, 2H), 6.90-6.96 (m, 1H), 7.02-7.08 (m, 1H), 7.18-7.22 (m, 1H).

Intermediate 6

2-Fluoro-5-methylbenzyl bromide

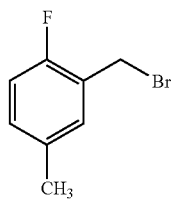

An oven dried round bottom flask is charged with boron tribromide (13 mL, 140 mmol) and is cooled to −30-45° C. 2-Fluoro-5-methyl-benzyl alcohol (6.5 g, 46 mmol) is then added slowly after which time the reaction is allowed to warm to room temperature.

The reaction is then poured slowly onto ice and the product is extracted into ether. The combined organic layers are concentrated under reduced pressure and the resulting residue is purified by silica gel flash column chromatography to give the title compound.

$^1$HNMR (400 MHz, CDCl$_3$) δ 2.36 (s, 3H), 4.74 (s, 2H), 6.90-6.96 (m, 1H), 7.02-7.08 (m, 1H), 7.09-7.12 (m, 1H).

Intermediate 7

[2-(5-Chloro-2-fluoro-phenyl)-1-(methoxy-methyl-carbamoyl)-ethyl]-carbamic acid tert-butyl ester

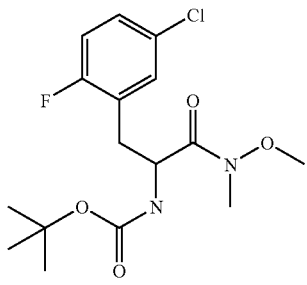

Using general procedure 4 with 2-bromomethyl-4-chloro-1-fluoro-benzene (4.9 g, 22 mmol) gives the title compound.
$^1$HNMR
MS (m/e): 305 (M-C$_4$H$_9$+1)

Intermediate 8

[2-(2-Chloro-5-fluoro-phenyl)-1-(methoxy-methyl-carbamoyl)-ethyl]-carbamic acid tert-butyl ester

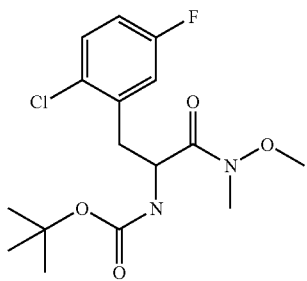

Using general procedure 4 with 2-bromomethyl-1-chloro-4-fluoro-benzene (4.1 g, 18 mmol) gives the title compound.
$^1$HNMR
MS (m/e): 305 (M-C$_4$H$_9$+1)

Intermediate 9

[2-(2,5-Dichloro-phenyl)-1-(methoxy-methyl-carbamoyl)-ethyl]-carbamic acid tert-butyl ester

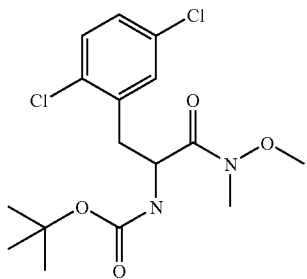

Using general procedure 4 with 2-bromomethyl-1,4-dichloro-benzene (4.6 g, 19 mmol) gives the title compound.
$^1$HNMR
MS (m/e): 399 (M+Na)

Intermediate 10

[2-(2-Fluoro-5-trifluoromethyl-phenyl)-1-(methoxy-methyl-carbamoyl)-ethyl]-carbamic acid tert-butyl ester

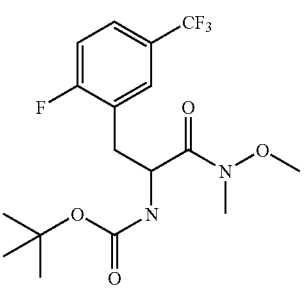

Using general procedure 4 with 2-bromomethyl-1-fluoro-4-trifluoromethyl-benzene (4.6 g, 18 mmol) gives the title compound.
$^1$HNMR
MS (m/e): 339 (M-C$_4$H$_9$+1)

Intermediate 11

[2-(2,5-Difluoro-phenyl)-1-(methoxy-methyl-carbamoyl)-ethyl]-carbamic acid tert-butyl ester

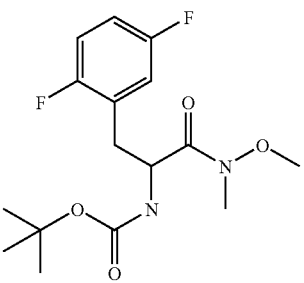

Using general procedure 4 with 2-bromomethyl-1,4-difluoro-benzene (4.1 g, 20 mmol) gives the title compound.
$^1$HNMR
MS (m/e): 367 (M+Na)

Intermediate 12

[2-(3,4-Difluoro-phenyl)-1-(methoxy-methyl-carbamoyl)-ethyl]-carbamic acid tert-butyl ester

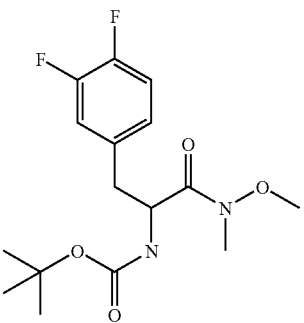

Using general procedure 4 with 4-bromomethyl-1,2-difluoro-benzene (2.2 g, 11 mmol) gives the title compound.
$^1$HNMR
MS (m/e): 367 (M+Na)

Intermediate 13

(R)-[1-(Methoxy-methyl-carbamoyl)-2-(2,4,5-trifluoro-phenyl)-ethyl]-carbamic acid benzyl ester

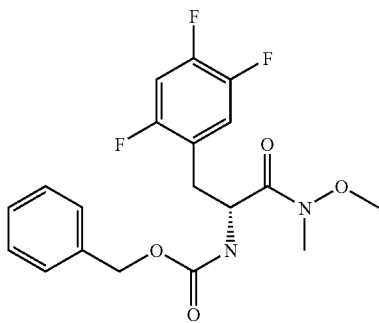

Step A:

(R)-2-Benzyloxycarbonylamino-3-(2,4,5-trifluoro-phenyl)-propionic acid methyl ester Using general procedure 6 with 2,4,5-trifluorobenzaldehyde (12.7 g, 79 mmol) gives the title compound.
¹HNMR
MS (m/e): 368 (M+1)

Step B:

(R)-2-Benzyloxycarbonylamino-3-(2,4,5-trifluoro-phenyl)-propionic acid

Using general procedure 7 with (R)-2-benzyloxycarbonylamino-3-(2,4,5-trifluoro-phenyl)-propionic acid methyl ester (5.0 g, 14 mmol) gives the title compound.
¹HNMR
MS (m/e): 352 (M+1)

Step C:

(R)-[1-(Methoxy-methyl-carbamoyl)-2-(2,4,5-trifluoro-phenyl)-ethyl]-carbamic acid benzyl ester Using general procedure 1 with (R)-3-benzyloxycarbonylamino-2-oxo-4-(2,4,5-trifluoro-phenyl)-butyric acid (3.8 g, 11 mmol) gives the title compound.
¹HNMR
MS (m/e): 397 (M+1)

Intermediate 14

[(R)-2-(2,5-Difluoro-phenyl)-1-(methoxy-methyl-carbamoyl)-ethyl]-carbamic acid benzyl ester

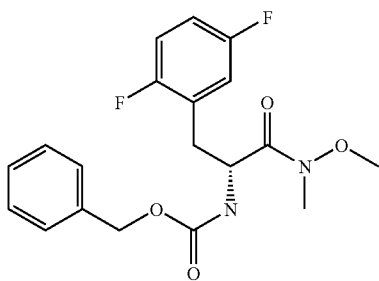

Step A:

(R)-2-Benzyloxycarbonylamino-3-(2,5-difluoro-phenyl)-propionic acid methyl ester Using general procedure 5 with 2,5-difluorobenzaldehyde (200 g, 1.4 mol) gives the title compound.
¹HNMR
MS (m/e): 350 (M+1)

Step B:

(R)-2-Benzyloxycarbonylamino-3-(2,5-difluoro-phenyl)-propionic acid

Using general procedure 6 with (R)-2-benzyloxycarbonylamino-3-(2,5-difluoro-phenyl)-propionic acid methyl ester (60 g, 170 mmol) gives the title compound.
¹HNMR
MS (m/e): 334 (M−1)

Step C:

[(R)-2-(2,5-Difluoro-phenyl)-1-(methoxy-methyl-carbamoyl)-ethyl]-carbamic acid benzyl ester Using general procedure 1 with (R)-3-benzyloxycarbonylamino-2-oxo-4-(2,5-difluoro-phenyl)-butyric acid (20 g, 61 mmol) gives the title compound.
¹HNMR
mass spectrum (m/e): 379 (M+1)

Intermediate 15

[2-(2,5-Dimethylphenyl)-1-(methoxymethylcarbamoyl)-ethyl]-carbamic acid tert-butyl ester

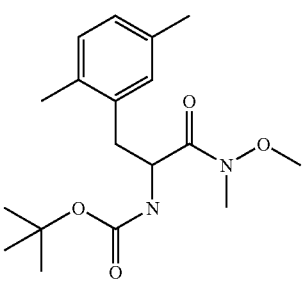

Using general procedure 4 with 2,5-dimethyl chloride (3.4 g, 22 mmol) provides the title compound.
¹HNMR, (400 MHz, CDCl₃) δ 1.38 (s, 9H), 2.26 (s, 3H), 2.32 (s, 3H), 2.76-2.86 (m, 1H), 2.98-3.04 (m, 1H), 3.17 (s, 3H), 3.60 (s, 3H), 4.92-5.01 (m, 1H), 5.12-5.20 (m, 1H), 6.88-6.98 (m, 2H), 6.99-7.03 (m, 1H).

Intermediate 16

[2-(4-Chloro-2-fluorophenyl)-1-(methoxymethylcarbamoyl)-ethyl]-carbamic acid tert-butyl ester

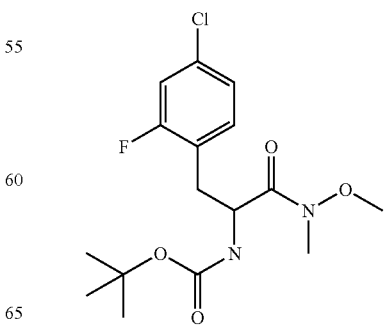

Using general procedure 4 with 4-chloro-2-fluoro-benzyl bromide (4.9 g, 22 mmol) gives the title compound.

¹HNMR (400 MHz, CDCl₃) δ 1.38 (s, 9H), 2.86-2.96 (m, 1H), 3.00-3.10 (m, 1H), 3.18 (s, 3H), 3.77 (s, 3H), 4.88-4.98 (m, 1H), 5.18-5.27 (m, 1H), 7.00-7.10 (m, 3H).

Intermediate 17

[2-(5-Fluoro-2-trifluoromethylphenyl)-1-(methoxymethylcarbamoyl)-ethyl]-carbamic acid tert-butyl ester

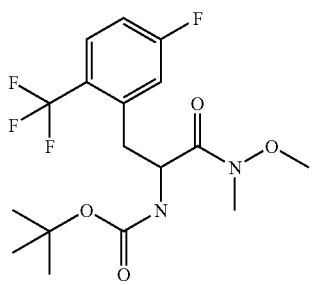

Using general procedure 4 with 5-fluoro-2-trifluoromethyl-benzyl bromide (7.1 g, 28 mmol) gives the title compound.

¹HNMR (400 MHz, CDCl₃) δ 1.38 (s, 9H), 2.88-2.96 (m, 1H), 3.02-3.08 (m, 1H), 3.18 (s, 3H), 3.78 (s, 3H), 4.90-4.98 (m, 1H), 5.18-5.22 (m, 1H), 7.00-7.10 (m, 3H).

Intermediate 18

2-tert-Butoxycarbonylamino-3-(2-fluoro-5-methylphenyl)-propionic acid ethyl ester

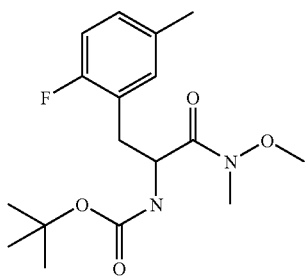

Step A:

2-tert-Butoxycarbonylamino-3-(2-fluoro-5-methylphenyl)-propionic acid ethyl ester Using general procedure 4 with 2-fluoro-5-methyl-benzyl bromide (7.2 g, 36 mmol) and substituting (benzhydrylideneamino)-acetic acid ethyl ester for 2-(benzhydrylideneamino)-N-methoxy-N-methyl acetamide gives the title compound.

¹HNMR (400 MHz, CDCl₃) δ 1.20-1.29 (m, 3H), 1.40 (s, 9H), 2.30 (s, 3H), 3.00-3.18 (m, 2H), 4.12-4.20 (m, 2H), 4.50-4.58 (m, 1H), 5.04-5.10 (m, 1H), 6.84-6.96 (m, 2H), 6.97-7.02 (m, 1H).

Step B:

2-tert-Butoxycarbonylamino-3-(2-fluoro-5-methylphenyl)-propionic acid

To a solution of 2-tert-butoxycarbonylamino-3-(2-fluoro-5-methylphenyl)-propionic acid ethyl ester (7.7 g, 24 mmol) in 60 mL of THF and 60 mL of MeOH is added lithium hydroxide (1.5 g, 35.6 mmol) in H₂O (15 mL). The reaction is stirred at room temperature for 1.5 hr after which time 1M HCl is added until the mixture reaches pH 4. The product is extracted into dichloromethane and the combine the organic layers are dried over MgSO4, filtered, and concentrated to give the title compound.

¹HNMR (400 MHz, CDCl₃) δ 1.35 (s, 3H), 1.38 (s, 6H), 2.28 (s, 3H), 3.00-3.10 (m, 1H), 3.20-3.26 (m, 1H), 4.56-4.60 (m, 1H), 4.98-5.04 (m, 1H), 6.90-6.97 (m, 1H), 6.98-7.02 (m, 2H).

Step C:

[2-(2-Fluoro-5-methylphenyl)-1-(methoxymethylcarbamoyl)-ethyl]-carbamic acid tert-butyl ester Using general procedure 1 with 2-tert-butoxycarbonylamino-3-(2-fluoro-5-methylphenyl)-propionic acid (3.5 g, 12 mmol) gives the title compound.

¹HNMR (400 MHz, CDCl₃) δ 1.38 (s, 9H), 2.24 (3H), 2.87-2.96 (m, 1H), 2.99-3.08 (m, 1H), 3.19 (s, 3H), 3.76 (s, 3H), 4.90-5.00 (m, 1H), 5.18-5.24 (m, 1H), 6.84-6.96 (m, 2H), 6.97-7.00 (m, 1H).

Intermediate 19

[(R)-1-(Methoxy-methyl-carbamoyl)-2-m-tolyl-ethyl]-carbamic acid tert-butyl ester

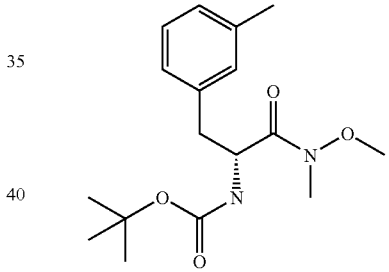

Using general procedure 1 with (R)-2-tert-butoxycarbonylamino-3-m-tolyl-propionic acid (5.0 g, 18 mmol) gives the title compound.

¹HNMR (400 MHz, CDCl₃) δ 1.38 (s, 9H), 2.34 (s, 3H), 2.78-2.86 (m, 1H), 2.98-3.04 (m, 1H), 3.17 (s, 3H), 3.64 (s, 3H), 4.90-4.98 (m, 1H), 5.10-5.20 (m, 1H), 6.94-6.99 (m, 2H), 7.00-7.04 (m, 1H), 7.16-7.20 (m, 1H).

Intermediate 20

[(R)-1-(Methoxy-methyl-carbamoyl)-2-o-tolyl-ethyl]-carbamic acid tert-butyl ester

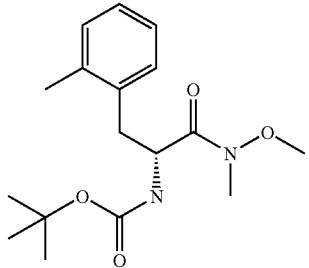

Using general procedure 1 with (R)-2-tert-butoxycarbonylamino-3-o-tolyl-propionic acid (5.0 g, 18 mmol) gives the title compound.

¹HNMR (400 MHz, CDCl₃) δ 1.38 (s, 9H), 2.38 (s, 3H), 2.80-2.90 (m, 1H), 3.00-3.10 (m, 1H), 3.15 (s, 3H), 3.62 (s, 3H), 4.93-5.02 (m, 1H), 5.14-5.20 (m, 1H), 7.07-7.17 (m, 4H).

Intermediate 21

[(R)-2-(4-Chloro-phenyl)-1-(methoxy-methyl-carbamoyl)-ethyl]-carbamic acid tert-butyl ester

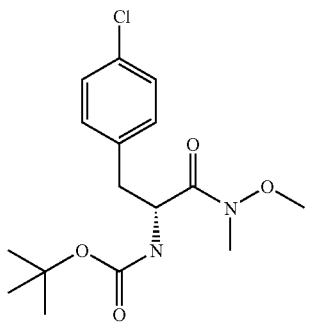

Using general procedure 1 with (R)-2-tert-butoxycarbonylamino-3-p-chloro-propionic acid (5.0 g, 17 mmol) gives the title compound.

¹HNMR (400 MHz, CDCl₃) δ 1.38 (s, 9H), 2.80-2.90 (m, 1H), 2.98-3.10 (m, 1H), 3.18 (s, 3H), 3.70 (s, 3H), 4.88-4.98 (m, 1H), 5.12-5.20 (m, 1H), 7.02-7.18 (m, 2H), 7.20-7.30 (m, 2H).

Intermediate 22

[(R)-1-(Methoxy-methyl-carbamoyl)-2-pyridin-2-yl-ethyl]-carbamic acid tert-butyl ester

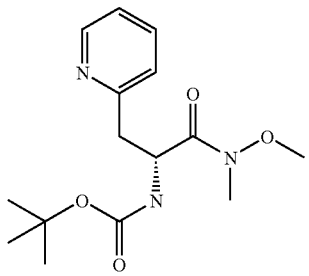

Using general procedure 1 with (R)-2-tert-butoxycarbonylamino-3-pyridin-2-yl-propionic acid (5.0 g, 19 mmol) gives the title compound.

¹HNMR (400 MHz, CDCl₃) δ 1.38 (s, 9H), 3.02-3.12 (m, 1H), 3.20 (s, 3H), 3.20-3.22 (m, 1H), 3.78 (s, 3H), 4.98-5.04 (m, 1H), 5.50-5.58 (m, 1H), 7.05-7.18 (m, 2H), 7.58-7.62 (m, 1H), 8.56-8.58 (m, 1H).

Intermediate 23

2-[(4R,5S)-3-tert-Butoxycarbonyl-4-(2-fluoro-benzyl)-2,2-dimethyl-oxazolidin-5-ylmethyl]-nicotinic acid

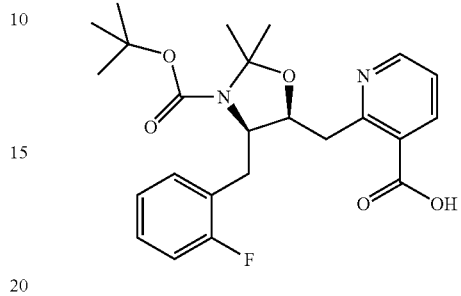

Step A:

2-[3-tert-Butoxycarbonylamino-4-(2-fluoro-phenyl)-2-oxo-butyl]-nicotinic acid

To a solution of 2-methyl nicotinic acid (25 g, 180 mmol) and TMEDA (55 mL, 360 mmol) in 400 mL THF at −68° C. is added a 2M solution of LDA in heptane/THF/ethyl benzene (180 mL, 360 mmol) over 10 min without stirring. Stirring is then initiated and the internal temperature is allowed to rise to −40° C. and is maintained at this temp for 30 min. The solution is then re-cooled to −68° C. and a solution of [2-(2-fluoro-phenyl)-1-methoxymethyl-carbamoyl)-ethyl]-carbamic acid tert-butyl ester (20 g, 61 mmol) in 100 ml of dry THF is added over 10 min. The reaction is allowed to stir at −68° C. for 1 hr. The reaction is then poured into a NaHSO₄ buffer solution (300 ml) containing 100 g of NaHSO₄, which is chilled with crushed ice prior to addition. The pH of the solution is monitored with a pH meter and maintained below pH 7. The solution is then adjusted to pH 3-4 with 1N HCl and the product is extracted into dichloromethane. The combined organic phases are dried over sodium sulfate, filtered, and concentrated under reduced pressure to give the title compound. The product can be further purified by trituration with ether.

¹HNMR

MS (m/e): 403 (M+1)

Step B:

2-[3-tert-Butoxycarbonylamino-4-(2-fluoro-phenyl)-2-hydroxy-butyl]-nicotinic acid To a solution of 2-[3-tert-butoxycarbonylamino-4-(2-fluoro-phenyl)-2-oxo-butyl]-nicotinic acid (14 g, 35 mmol) in 100 mL of EtOH at 0° C. is added NaBH₄ (5.3 g, 140 mmol). After 20 min, 30 mL of water is added to the reaction and the reaction poured into 300 ml of water. The pH is adjusted to ~pH3 with 2M NaHSO₄ at which point a white solid precipitates and isolation by filtration gives the title compound.

¹HNMR

MS (m/e): 405 (M+1)

Step C:

2-[(R)-3-tert-Butoxycarbonyl-4-(2-fluoro-benzyl)-2,2-dimethyl-oxazolidin-5-ylmethyl]-nicotinic acid To a solution of 2-[3-tert-Butoxycarbonylamino-4-(2-fluoro-phenyl)-2-hydroxy-butyl]-nicotinic acid (13 g, 32 mmol) in 500 mL of 2,2-dimethoxypropane and 500 mL of acetone at 0° C. is added boron trifluoride diethyl etherate (3.2 mL, 25 mmol). The reaction is heated at 40° C. overnight after which time the solvent is removed under reduced pressure. The resultant residue is then partitioned between dichloromethane and water and extracted with dichloromethane. The combined organic phases are dried over sodium sulfate, filtered, and concentrated under reduced pressure. Purification by silica gel flash column chromatography gives the title compound.
¹HNMR
MS (m/e): 445 (M+1)

Step D:

2-[(4R,5S)-3-tert-Butoxycarbonyl-4-(2-fluoro-benzyl)-2,2-dimethyl-oxazolidin-5-ylmethyl]-nicotinic acid methyl ester To a solution of 2-[(R)-3-tert-butoxycarbonyl-4-(2-fluoro-benzyl)-2,2-dimethyl-oxazolidin-5-ylmethyl]-nicotinic acid (11 g, 25 mmol) in 200 mL of benzene and 30 mL of methanol is added a 2M solution of trimethylsilyl-diazomethane in hexane (16 mL, 32 mmol). The reaction is allowed to stir for 1 hour at RT after which time the solvent is removed under reduced pressure. Purification of the resultant residue by silica gel flash column chromatography gives the title compound.
¹HNMR
MS (m/e): 459 (M+1)

Step E:

2-[(4R,5S)-3-tert-Butoxycarbonyl-4-(2-fluoro-benzyl)-2,2-dimethyl-oxazolidin-5-ylmethyl]-nicotinic acid To a solution of 2-[(4R,5S)-3-tert-butoxycarbonyl-4-(2-fluoro-benzyl)-2,2-dimethyl-oxazolidin-5-ylmethyl]-nicotinic acid methyl ester (5.5 g, 12 mmol) in 100 mL of dioxane/water (2:1) is added lithium hydroxide (0.57 g, 24 mmol). The reaction is stirred at room temperature for 2 hr after which time the reaction is diluted and the pH adjusted to pH 4-5 with a 2M solution of sodium bisulfate. The product is extracted into dichloromethane and the combined organic phases are dried over sodium sulfate, filtered, and concentrated under reduced pressure. Purification of the resultant residue by silica gel flash column chromatography gives the title compound.
¹HNMR
MS (m/e): 445 (M+1)

Intermediate 24

(R)-2-Dibenzylamino-3-(2-fluoro-phenyl)-propionaldehyde

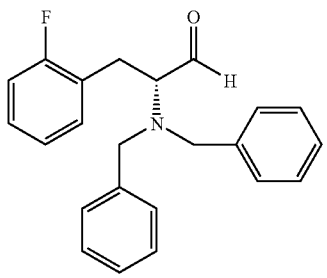

Step A:

(R)-2-Amino-3-(2-fluoro-phenyl)-propionic acid methyl ester

Acetyl chloride (20 mL, 300 mmol) is added dropwise to 100 mL of methanol at 0° C. After 10 minutes, (D)-2-fluoro-phenylalanine (9.5 g, 53 mmol) is added and the reaction is heated at reflux for 3 hr. The reaction is then cooled to room temperature and the solvent is removed under reduced pressure to give the title compound.
¹HNMR
MS (m/e): 198 (M+1)

Step B:

(R)-2-Dibenzylamino-3-(2-fluoro-phenyl)-propionic acid methyl ester

To a solution of (R)-2-Amino-3-(2-fluoro-phenyl)-propionic acid methyl ester (4 g, 17 mmol) and benzyl bromide (4.5 mL, 38 mmol) in 200 mL of acetonitrile is added potassium carbonate. After 5 hours the reaction is heated at 50° C. for 16 hours. The reaction mixture is then cooled to room temperature and is poured into 500 mL of saturated ammonium chloride. The product is extracted into dichloromethane and the combined organic phases are dried over sodium sulfate, filtered and concentrated. Purification of the crude residue by silica gel flash column chromatography gives the title compound.
¹HNMR
MS (m/e): 378 (M+1)

Step C:

(R)-2-Dibenzylamino-3-(2-fluoro-phenyl)-propan-1-ol

To a solution of (R)-2-Dibenzylamino-3-(2-fluoro-phenyl)-propionic acid methyl ester (4.6 g, 12 mmol) in 100 mL of THF at −10° C. is slowly added a 1M solution of lithium aluminum hydride in THF (19 mL, 18 mmol). After 10 minutes the reaction is quenched by slow addition of 1.2 mL of water and 1.2 mL of 1N sodium hydroxide. The mixture is then filtered through a pad of celite and the filtrate is concentrated to give the title compound.
¹HNMR
MS (m/e): 350 (M+1)

Step D:

(R)-2-Dibenzylamino-3-(2-fluoro-phenyl)-propionaldehyde

To a solution of (R)-2-dibenzylamino-3-(2-fluoro-phenyl)-propan-1-ol (1 g, 2.9 mmol) in 2 mL of diisopropyl-ethyl-amine at 10° C. is slowly added a solution of sulfur trioxide pyridine complex (1.4 g, 8.6 mmol) in 5 mL of DMSO. The reaction is allowed to stir at room temperature for 45 minutes after which time the reaction is quenched by addition of ice water. The product is extracted into ether and the combined organic phases are washed with water, 5% citric acid, and brine. The organic layer is dried over sodium sulfate, filtered, and concentrated under reduce pressure to give the title compound.
¹HNMR
MS (m/e): 348 (M+1)

Intermediate 25

(3-Ethoxycarbonyl-pyridin-2-ylmethyl)-trimethyl-phosphonium Bromide

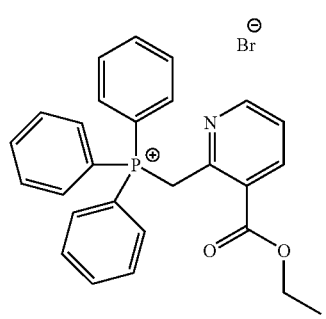

A stirred mixture of N-bromosuccinimide (5.6 g, 31 mmol), 2-Methyl-nicotinic acid ethyl ester (4.1 g, 24 mmol), AIBN (0.05 g, 0.3 mmol) in 50 mL of carbon tetrachloride at 50° C. is irradiated with a 250 Watt heat lamp for 45 minutes. The reaction was cooled to room temperature and is poured into saturated sodium bicarbonate. The products are extracted into dichloromethane and the combined organic layers are dried over sodium sulfate, filtered, and concentrated under reduced pressure to afford a residue which is immediately dissolved in 100 mL of toluene. To the solution is added triphenyl phosphine (8.1 g, 31 mmol) and the reaction is heated at reflux for 2 hours. The heat source is removed and filtration gives the title compound.

$^1$HNMR

MS (m/e): 426 (M+1)

Intermediate 26

[(R)-2-(2-Fluoro-phenyl)-1-(methoxy-methyl-carbamoyl)-ethyl]-carbamic acid tert-butyl ester

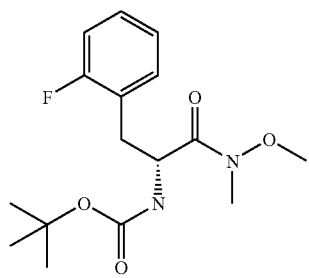

Using general procedure 1 with (R)-2-tert-Butoxycarbonylamino-3-(2-fluoro-phenyl)-propionic acid (15 g, 53 mmol) gives the title compound.

$^1$HNMR

MS (m/e): 349 (M+Na)

Intermediate 27

N-Isopropyl-2-methyl-nicotinamide

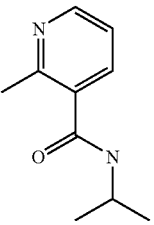

To a solution of 2-methyl nicotinic acid (2.5 g, 18 mmol), HOBT (3.7 g, 27 mmol), isopropylamine (3.1 mL, 36 mmol), and triethylamine (7.5 mL, 54 mmol) in 150 mL of DMF is added EDC (5.2 g, 27 mmol). The reaction is allowed to stir at room temperature for 24 hours and is then concentrated under reduced pressure. Ethyl acetate and brine is added and the layers are separated. The organic layer is dried over sodium sulfate, filtered, and concentrated under reduced pressure. Purification of the crude residue by silica gel flash column chromatography gives the title compound.

$^1$HNMR

MS (m/e): 179 (M+1)

Intermediate 28

[(R)-2-(2,5-Difluoro-phenyl)-1-(methoxy-methyl-carbamoyl)-ethyl]-carbamic acid tert-butyl ester

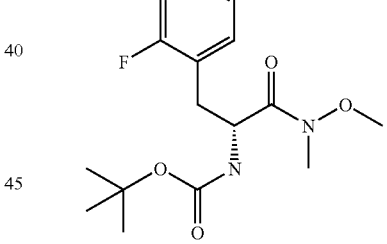

Step A:

(R)-2-tert-Butoxycarbonylamino-3-(2,5-difluoro-phenyl)-propionic acid methyl ester Using general procedure 6 with 2,5-difluorobenzaldehyde (5.5 g, 39 mmol) gives the title compound.

$^1$HNMR

MS (m/e): 216 (M+1-C$_4$H$_9$)

Step B:

(R)-2-tert-Butoxycarbonylamino-3-(2,5-difluoro-phenyl)-propionic acid

Using general procedure 7 with (R)-2-tert-butoxycarbonylamino-3-(2,5-difluoro-phenyl)-propionic acid methyl ester (23 g, 72 mmol) gives the title compound.

$^1$HNMR

MS (m/e): 300 (M−1)

Step C:

[(R)-2-(2,5-Difluoro-phenyl)-1-(methoxy-methyl-carbamoyl)-ethyl]-carbamic acid tert-butyl ester Using general procedure 1 with (R)-2-tert-Butoxycarbonylamino-3-(2,5-difluoro-phenyl)-propionic acid (20 g, 65 mmol) gives the title compound.
¹HNMR (400 MHz, CDCl₃) δ 1.37 (s, 9H), 2.89 (dd, J=7.6, 13.6 Hz, 1H), 3.06 (dd, J=4.8, 13.6, 1H), 3.19 (s, 3H), 3.76 (s, 3H), 4.90-5.02 (m, 1H), 5.24 (d, J=8.4 Hz, 1H), 6.83-6.92 (m, 2H), 6.92-6.95 (m, 1H).

Intermediate 29

N-(2-Methylpyridin-3-yl)acetamide

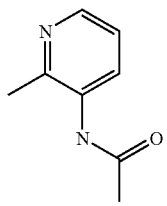

Acetic Acid Anhydride (17.9 mmol; 1.7 mL) was added to 3-Amino-2-picoline (17.0 mmol; 1.8 g) in dichloromethane (10 mL) and diisopropylethylamine (17.9 mmol; 3.1 mL) at 25° C. under argon. The reaction aged 30 min at 25° C. then was diluted with dichloromethane and extracted with water and brine. The aqueous layer was extracted with dichloromethane and ether then the combined organics were dried over sodium sulfate, filtered and concentrated in vacuo. The resulting yellow oil was purified by chromatography (0% to 66% ethyl acetate in hexane) to afford the title compound.
¹HNMR
MS (m/e): 151.3 (M+1)
Preparation of DPIV Inhibitors:

EXAMPLE 1

2-[(2S,3R)-3-Amino-4-(5-chloro-2-fluoro-phenyl)-2-hydroxy-butyl]-N-tert-butyl-nicotinamide Dihydrochloride

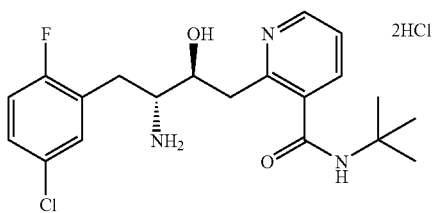

Step A:

[3-(3-tert-Butylcarbamoyl-pyridin-2-yl)-1-(5-chloro-2-fluoro-benzyl)-2-oxo-propyl]-carbamic acid tert-butyl ester Using general procedure 2 with [2-(5-chloro-2-fluoro-phenyl)-1-(methoxy-methyl-carbamoyl)-ethyl]-carbamic acid tert-butyl ester (2.9 g, 8.1 mmol) gives the title compound.
¹HNMR
MS (m/e): 492 (M+1)

Step B:

[(1RS,2SR)-3-(3-tert-Butylcarbamoyl-pyridin-2-yl)-1-(5-chloro-2-fluoro-benzyl)-2-hydroxy-propyl]-carbamic acid tert-butyl ester Using general procedure 3, [3-(3-tert-butylcarbamoyl-pyridin-2-yl)-1-(5-chloro-2-fluoro-benzyl)-2-oxo-propyl]-carbamic acid tert-butyl ester (2.3 g, 4.7 mmol) gives the title compound.
¹HNMR
MS (m/e): 494 (M+1)

Step C:

2-[(2S,3R)-3-Amino-4-(5-chloro-2-fluoro-phenyl)-2-hydroxy-butyl]-N-tert-butyl-nicotinamide Dihydrochloride Using purification method 3 and general deprotection procedure 3 with [(1RS,2SR)-3-(3-tert-butylcarbamoyl-pyridin-2-yl)-1-(5-chloro-2-fluoro-benzyl)-2-hydroxy-propyl]-carbamic acid tert-butyl ester (1.5 g, 3.0 mmol) gives the title compound.
¹HNMR (400 MHz, DMSO-d₆) δ 1.36 (s, 9H), 2.87-2.97 (m, 1H), 3.09-3.26 (m, 3H), 3.50 (br s, 1H), 4.30-4.35 (m, 1H), 7.23 (t, J=9.2 Hz, 1H), 7.34-7.39 (m, 1H), 7.59 (dd, J=6.6, 2.7 Hz, 1H), 7.69-7.75 (m, 1H), 8.17-8.27 (m, 3H), 8.44 (s, 1H), 8.75-8.78 (m, 1H).
MS (m/e): 394 (M+1)

EXAMPLE 2

2-[(2S,3R)-3-Amino-4-(5-fluoro-2-chloro-phenyl)-2-hydroxy-butyl]-N-tert-butyl-nicotinamide Dihydrochloride

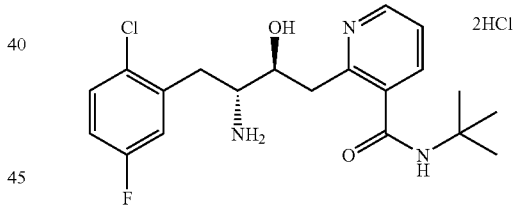

Step A:

[3-(3-tert-Butylcarbamoyl-pyridin-2-yl)-1-(2-chloro-5-fluoro-benzyl)-2-oxo-propyl]-carbamic acid tert-butyl ester Using general procedure 2 with [2-(2-chloro-5-fluoro-phenyl)-1-(methoxy-methyl-carbamoyl)-ethyl]-carbamic acid tert-butyl ester (0.81 g, 2.2 mmol) gives the title compound.
¹HNMR
MS (m/e): 492 (M+1)

Step B:

[(1RS,2SR)-3-(3-tert-Butylcarbamoyl-pyridin-2-yl)-1-(2-chloro-5-fluoro-benzyl)-2-hydroxy-propyl]-carbamic acid tert-butyl ester Using general procedure 3, [3-(3-tert-butylcarbamoyl-pyridin-2-yl)-1-(2-chloro-5-fluoro-benzyl)-2-oxo-propyl]-carbamic acid tert-butyl ester (0.63 g, 1.3 mmol) gives the title compound.
¹HNMR
MS (m/e): 494 (M+1)

Step C:

2-[(2S,3R)-3-Amino-4-(5-fluoro-2-chloro-phenyl)-2-hydroxy-butyl]-N-tert-butyl-nicotinamide hydrochloride salt Using purification method 3 and general deprotection procedure 3 with [(1RS,2SR)-3-(3-tert-butylcarbamoyl-pyridin-2-yl)-1-(2-chloro-5-fluoro-benzyl)-2-hydroxy-propyl]-carbamic acid tert-butyl ester (0.32 g, 0.65 mmol) gives the title compound.
¹HNMR (400 MHz, DMSO-d₆) δ 1.36 (s, 9H), 2.94-3.03 (m, 1H), 3.14-3.24 (m, 3H), 3.54 (br s, 1H), 4.36-4.41 (m, 1H), 7.18 (td, J=8.5, 3.2 Hz, 1H), 7.42 (dd, J=9.6, 3.2 Hz, 1H), 7.50 (dd, J=8.6, 5.2 Hz, 1H), 7.60-7.64 (m, 1H), 8.03-8.22 (m, 3H), 8.34 (s, 1H), 8.70-8.73 (m, 1H).
MS (m/e): 394 (M+1)

EXAMPLE 3

2-[(2S,3R)-3-Amino-4-(2,5-dichloro-phenyl)-2-hydroxy-butyl]-N-tert-butyl-nicotinamide Dihydrochloride

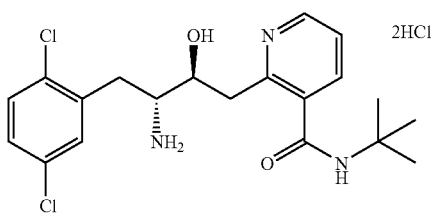

Step A:

[3-(3-tert-Butylcarbamoyl-pyridin-2-yl)-1-(2,5-dichloro-benzyl)-2-oxo-propyl]-carbamic acid tert-butyl ester Using general procedure 2 with [2-(2,5-dichloro-phenyl)-1-(methoxy-methyl-carbamoyl)-ethyl]-carbamic acid tert-butyl ester (1.9 g, 5.1 mmol) gives the title compound.
¹HNMR
MS (m/e): 508 (M+1)
Step B:

[(1RS,2SR)-3-(3-tert-Butylcarbamoyl-pyridin-2-yl)-1-(2,5-dichloro-benzyl)-2hydroxy-propyl]-carbamic acid tert-butyl ester Using general procedure 3, [3-(3-tert-butylcarbamoyl-pyridin-2-yl)-1-(2,5-dichloro-benzyl)-2-oxo-propyl]-carbamic acid tert-butyl ester (1.5 g, 3.0 mmol) gives the title compound.
¹HNMR
MS (m/e): 510 (M+1)
Step C:

2-[(2S,3R)-3-Amino-4-(2,5-dichloro-phenyl)-2-hydroxy-butyl]-N-tert-butyl-nicotinamide Dihydrochloride Using purification method 3 and general deprotection procedure 3 with [(1RS,2SR)-3-(3-tert-butylcarbamoyl-pyridin-2-yl)-1-(2,5-dichloro-benzyl)-2-hydroxy-propyl]-carbamic acid tert-butyl ester (0.64 g, 3.0 mmol) gives the title compound.
¹HNMR (400 MHz, DMSO-d₆) δ 1.36 (s, 9H), 2.92-3.00 (m, 1H), 3.13-3.21 (m, 3H), 3.52 (br s, 1H), 4.36-4.41 (m, 1H), 7.38 (dd, J=8.7, 2.5 Hz, 1H), 7.48 (d, J=8.8 Hz, 1H), 7.50-7.56 (m, 1H), 7.61 (d, J=2.5 Hz, 1H), 7.95-8.11 (m, 3H), 8.28 (s, 1H), 8.65-8.69 (m, 1H).
MS (m/e): 410 (M+1)

EXAMPLE 4

2-[(2SR,3RS)-3-Amino-4-(2-fluoro-5-trifluoromethyl-phenyl)-2-hydroxy-butyl]-N-tert-butyl-nicotinamide Dihydrochloride

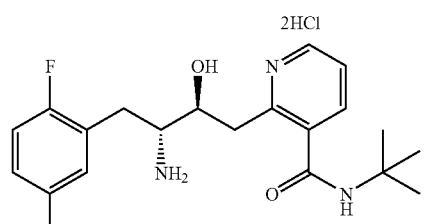

Step A:

[3-(3-tert-Butylcarbamoyl-pyridin-2-yl)-1-(2-fluoro-5-trifluoromethyl-benzyl)-2-oxo-propyl]-carbamic acid tert-butyl ester Using general procedure 2 with [2-(2-fluoro-5-trifluoromethyl-phenyl)-1-(methoxy-methyl-carbamoyl)-ethyl]-carbamic acid tert-butyl ester (2.0 g, 5.0 mmol) gives the title compound.
¹HNMR
MS (m/e): 526 (M+1)
Step B:

[(1RS,2SR)-3-(3-tert-Butylcarbamoyl-pyridin-2-yl)-1-(2-fluoro-5-trifluoromethyl-benzyl)-2-hydroxy-propyl]-carbamic acid tert-butyl ester Using general procedure 3 with [3-(3-tert-butylcarbamoyl-pyridin-2-yl)-1-(2-fluoro-5-trifluoromethyl-benzyl)-2-oxo-propyl]-carbamic acid tert-butyl ester (1.1g, 2.2 mmol) gives the title compound.
¹HNMR
MS (m/e): 528 (M+1)
Step C:

2-[(2SR,3RS)-3-Amino-4-(2-fluoro-5-trifluoromethyl-phenyl)-2-hydroxy-butyl]-N-tert-butyl-nicotinamide Dihydrochloride Using general deprotection procedure 3 with [(1RS,2SR)-3-(3-tert-butylcarbamoyl-pyridin-2-yl)-1-(2-fluoro-5-trifluoromethyl-benzyl)-2-hydroxy-propyl]-carbamic acid tert-butyl ester (0.13 g, 0.25 mmol) gives the title compound.
¹HNMR (400 MHz, DMSO-d₆) δ 1.36 (s, 9H), 2.94-3.03 (m, 1H), 3.14-3.24 (m, 3H), 3.51 (br s, 1H), 4.31-4.37 (m, 1H), 7.42 (t, J=9.0 Hz, 1H), 7.54-7.60 (m, 1H), 7.68-7.74 (m, 1H), 7.91 (d J=7.2 Hz, 1H), 8.00-8.18 (m, 3H), 8.32 (s, 1H), 8.68 (d, J=4.6 Hz, 1H).

MS (m/e): 428 (M+1)

EXAMPLE 5

2-[(2S,3R)-3-Amino-4-(2,5-difluoro)-2-hydroxy-butyl]-N-tert-butyl-nicotinamide Dihydrochloride

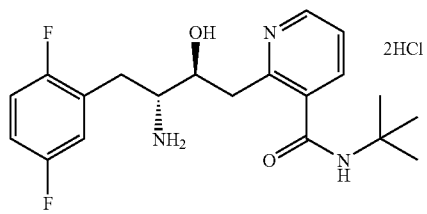

Step A:

[3-(3-tert-Butylcarbamoyl-pyridin-2-yl)-1-(2,5-difluoro-benzyl)-2-oxo-propyl]-carbamic acid tert-butyl ester Using general procedure 2 with [2-(2,5-difluoro-phenyl)-1-(methoxy-methyl-carbamoyl)-ethyl]-carbamic acid tert-butyl ester (2.1 g, 6.1 mmol) gives the title compound.
¹HNMR
MS (m/e): 476 (M+1)

Step B:

[(1RS,2SR)-3-(3-tert-Butylcarbamoyl-pyridin-2-yl)-1-(2,5-difluoro-benzyl)-2-hydroxy-propyl]-carbamic acid tert-butyl ester Using general procedure 3 with [3-(3-tert-butylcarbamoyl-pyridin-2-yl)-1-(2,5-difluoro-benzyl)-2-oxo-propyl]-carbamic acid tert-butyl ester (1.5 g, 3.2 mmol) gives the title compound.
¹HNMR
MS (m/e): 478 (M+1)

Step C:

2-[(2S,3R)-3-Amino-4-(2,5-difluoro)-2-hydroxy-butyl]-N-tert-butyl-nicotinamide Dihydrochloride Using general deprotection procedure 3 and purification method 3 with [(1RS,2SR)-3-(3-tert-butylcarbamoyl-pyridin-2-yl)-1-(2,5-difluoro-benzyl)-2-hydroxy-propyl]-carbamic acid tert-butyl ester (0.7 g, 1.5 mmol) gives the title compound.
¹HNMR (400 MHz, DMSO-$d_6$) δ 1.36 (s, 9H), 2.84-2.93 (m, 1H), 3.08-3.16 (m, 3H), 3.47 (br s, 1H), 4.30-4.36 (m, 1H), 7.11-7.18 (m, 1H), 7.19-7.26 (m, 1H), 7.29-7.36 (m, 1H), 7.52 (m, 1H), 7.92-8.13 (m, 3H), 8.28 (s, 1H), 8.66 (d, J=5.0 Hz, 1H).
MS (m/e): 378 (M+1)

EXAMPLE 6

2-[(2SR,3RS)-3-Amino-4-(3,4-difluoro)-2-hydroxy-butyl]-N-tert-butyl-nicotinamide Dihydrochloride

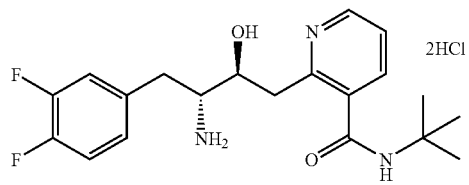

Step A:

[3-(3-tert-Butylcarbamoyl-pyridin-2-yl)-1-(3,4-difluoro-benzyl)-2-oxo-propyl]-carbamic acid tert-butyl ester Using general procedure 2 with [2-(3.4-difluoro-phenyl)-1-(methoxy-methyl-carbamoyl)-ethyl]-carbamic acid tert-butyl ester (1.3 g, 3.7 mmol) gives the title compound.
¹HNMR
MS (m/e): 476 (M+1)

Step B:

[(1RS,2SR)-3-(3-tert-Butylcarbamoyl-pyridin-2-yl)-1-(3,4-difluoro-benzyl)-2-hydroxy-propyl]-carbamic acid tert-butyl ester Using general procedure 3 with [3-(3-tert-butylcarbamoyl-pyridin-2-yl)-1-(3.4-difluoro-benzyl)-2-oxo-propyl]-carbamic acid tert-butyl ester (0.47 g, 0.99 mmol) gives the title compound.
¹HNMR
MS (m/e): 478 (M+1)

Step C:

2-[(2SR,3RS)-3-Amino-4-(3,4-difluoro)-2-hydroxy-butyl]-N-tert-butyl-nicotinamide Dihydrochloride Using general deprotection procedure 3 with [(1RS,2SR)-3-(3-tert-Butylcarbamoyl-pyridin-2-yl)-1-(3,4-difluoro-benzyl)-2-hydroxy-propyl]-carbamic acid tert-butyl ester (0.22 g, 0.46 mmol) gives the title compound.
1HNMR (400 MHz, DMSO-$d_6$) δ 1.36 (s, 9H), 2.82-2.91 (m, 1H), 3.04-3.21 (m, 3H), 3.40 (br s, 1H), 4.28-4.34 (m, 1H), 7.17-7.23 (m, 1H), 7.33-7.42 (m, 1H), 7.44-7.51 (m, 1H), 7.59-7.66 (m, 1H), 8.07 (br s, 3H), 8.37 (s, 1H), 8.72 (d, J=5.0 Hz, 1H).
MS (m/e): 378 (M+1)

EXAMPLE 7

2-[(2S,3R)-3-Amino-4-(2,4,5-trifluoro)-2-hydroxy-butyl]-N-tert-butyl-nicotinamide Dihydrochloride

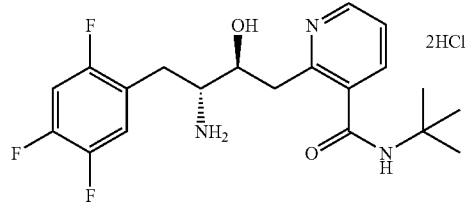

Step A:

[(R)-3-(3-tert-Butylcarbamoyl-pyridin-2-yl)-2-oxo-1-(2,4,5-trifluoro-benzyl)-propyl]-carbamic acid benzyl ester Using general procedure 2 with [(R)-1-(methoxy-methyl-carbamoyl)-2-(2,4,5-trifluoro-phenyl)-ethyl]carbamic acid benzyl ester (4.6 g, 11 mmol) gives the title compound.
1HNMR
MS (m/e): 528 (M+1)

Step B:

[(2S,3R)-3-(3-tert-Butylcarbamoyl-pyridin-2-yl)-2-hydroxy-1-(2,4,5-trifluoro-benzyl)-propyl]-carbamic acid benzyl ester Using general procedure 3 with [(R)-3-(3-tert-butylcarbamoyl-pyridin-2-yl)-2-oxo-1-(2,4,5-trifluoro-benzyl)-propyl]-carbamic acid benzyl ester (7.4 g, 14 mmol) gives the title compound.
1HNMR
MS (m/e): 528 (M+1)

Step C:

2-[(2S,3R)-3-Amino-4-(2,4,5-trifluoro)-2-hydroxy-butyl]-N-tert-butyl-nicotinamide Dihydrochloride Using general deprotection procedure 2 and purification method 3 with [(2S,3R)-3-(3-tert-butylcarbamoyl-pyridin-2-yl)-2-hydroxy-1-(2,4,5-trifluoro-benzyl)-propyl]-carbamic acid benzyl ester (5.3 g, 10 mmol) gives the title compound.
1HNMR (400 MHz, DMSO-$d_6$) δ 1.36 (s, 9H), 2.83-2.92 (m, 1H), 3.05-3.14 (m, 1H), 3.44 (br s, 1H), 4.31-4.36 (m, 1H), 7.48-7.63 (m, 3H), 7.94-8.00 (m, 1H), 8.10 (br s, 1H), 8.29 (s, 1H), 8.65-8.68 (m, 1H)
MS (m/e): 304 (M+1)

EXAMPLE 8

2-[(2S,3R)-3-Amino-4-(2,5-dimethyl-phenyl)-2-hydroxy-butyl]-N-tert-butyl-nicotinamide Dihydrochloride

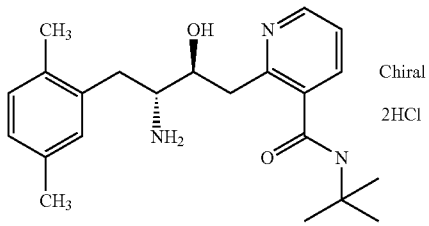

Step A:

[3-(3-tert-Butylcarbamoylpyridn-2-yl)-1-(2,5-dimethylbenzyl)-2-oxopropyl]-carbamic acid tert-butyl ester Using general procedure 2 with [2-(2,5-dimethylphenyl)-1-(methoxymethylcarbamoyl)-ethyl]-carbamic acid tert-butyl ester (1.7 g, 5.0 mmol) provides the title compound.
1HNMR
MS (m/e): 468 (M+1).

Step B:

[(1RS,2SR)-3-(3-tert-Butylcarbamoylpyridin-2-yl)-1-(2,5-dimethylbenzyl)-2-hydroxypropyl]-carbamic acid tert-butyl ester Using general procedure 3 with [3-(3-tert-butylcarbamoylpyridn-2-yl)-1-(2,5-dimethylbenzyl)-2-oxopropyl]-carbamic acid tert-butyl ester (1.1 g, 2.3 mmol) followed by purification method 2 gives the title compound
1HNMR
MS (m/e): 470 (M+1).

Step C:

2-[(2S,3R)-3-Amino-4-(2,5-dimethyl-phenyl)-2-hydroxy-butyl]-N-tert-butyl-nicotinamide Dihydrochloride Using general purification method 3 and deprotection procedure 3 with [(1RS,2SR)-3-(3-tert-Butylcarbamoylpyridin-2-yl)-1-(2,5-dimethylbenzyl)-2-hydroxypropyl]-carbamic acid tert-butyl ester (170 mg, 0.38 mmol) gives the title compound.
1HNMR (400 MHz, DMSO-d6) δ 1.38 (s, 9H), 2.22 (s, 3H), 2.23 (s, 3H), 2.78-2.84 (m, 1H), 2.98-3.06 (m, 1H), 3.08-3.18 (m, 2H), 3.50 (s, br, 1H), 4.30-4.38 (m, 1H), 6.94-6.98 (m, 1H), 7.02-7.08 (m, 1H), 7.12 (s, 1H), 7.50-7.60 (m, 1H), 7.94-8.10 (br, 3H), 8.30 (s, 1H), 8.68-8.74 (m, 1H).
MS (m/e): 370 (M+1).

EXAMPLE 9

2-[(2SR,3RS)-3-Amino-4-(4-chloro-2-fluoro-phenyl)-2-hydroxy-butyl]-N-tert-butyl-nicotinamide Dihydrochloride

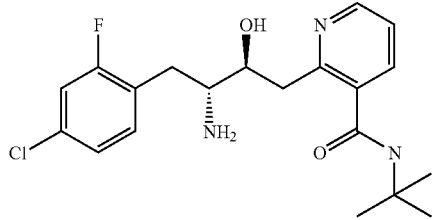

Step A:

[3-(3-tert-Butylcarbamoylpyridn-2-yl)-1-(4-chloro-2-fluorobenzyl)-2-oxopropyl]-carbamic acid tert-butyl ester Using general procedure 2 with [2-(4-chloro-2-fluorophenyl)-1-(methoxymethylcarbamoyl)-ethyl]-carbamic acid tert-butyl ester (2.1 g, 5.8 mmol) gives the title compound.
1HNMR
MS (m/e): 492 (M+1).

Step B:

[(1RS,2SR)-3-(3-tert-Butylcarbamoylpyridin-2-yl)-1-(4-chloro-2-fluorobenzyl)-2-hydroxypropyl]-carbamic acid tert-butyl ester Using general procedure 3 with [3-(3-tert-butylcarbamoylpyridn-2-yl)-1-(4-chloro-2-fluorobenzyl)-2-oxopropyl]-carbamic acid tert-butyl ester (1.4 g, 2.7 mmol) gives the title compound.
1HNMR
MS (m/e): 494 (M+1).

Step C:

2-[(2SR,3RS)-3-Amino-4-(4-chloro-2-fluoro-phenyl)-2-hydroxy-butyl]-N-tert-butyl-nicotinamide Dihydrochloride Using general deprotection procedure 3 with [(1RS,2SR)-3-(3-tert-butylcarbamoylpyridin-2-yl)-1-(4-chloro-2-fluorobenzyl)-2-hydroxypropyl]-carbamic acid tert-butyl ester (0.1 g, 0.20 mmol) provides the title compound.
$^1$H NMR (400 MHz, DMSO-d6) δ 1.36 (s, 9H), 2.82-2.92 (m, 1H), 3.02-3.18 (m, 3H). 3.38-3.44 (m, 1H), 4.28-4.37 (m, 1H), 7.26-7.32 (m, 1H), 7.38-7.52 (m, 3 H), 7.86-7.97 (m, 1H), 8.00 (br, 2H), 8.24 (s, 1H), 8.60-7.66 (m, 1H).
MS (m/e): 394 (M+1).

EXAMPLE 10

2-[(2SR,3RS)-3-Amino-4-(5-fluoro-2-trifluoromethylphenyl)-2-hydroxybutyl]-N-tert-butylnicotinamide Dihydrochloride

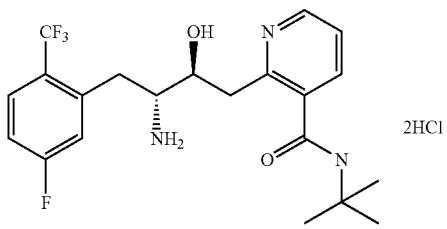

Step A:

[3-(3-tert-Butylcarbamoylpyridn-2-yl)-1-(5-fluoro-2-trifluoromethylbenzyl)-2-oxopropyl]-carbamic acid tert-butyl ester Using general procedure 2 with [2-(5-fluoro-2-trifluoromethylphenyl)-1-(methoxymethylcarbamoyl)-ethyl]-carbamic acid tert-butyl ester (2.2 g, 5.6 mmol) gives the title compound.
$^1$HNMR
MS (m/e): 526 (M+1).
Step B:

[(1RS,2SR)-3-(3-tert-Butylcarbamoylpyridin-2-yl)-1-(5-fluoro-2-trifluoromethylbenzyl)-2-hydroxypropyl]-carbamic acid tert-butyl ester Using general procedure 3 with [3-(3-tert-butylcarbamoylpyridn-2-yl)-1-(5-fluoro-2-trifluoromethylbenzyl)-2-oxopropyl]-carbamic acid tert-butyl ester (0.9 g, 1.7 mmol) gives the title compound.
$^1$HNMR
MS (m/e): 528 (M+1).
Step C:

2-[(2SR,3RS)-3-Amino-4-(5-fluoro-2-trifluoromethylphenyl)-2-hydroxybutyl]-N-tert-butylnicotinamide Dihydrochloride Using general deprotection procedure 3 with [(1RS,2SR)-3-(3-tert-butylcarbamoylpyridin-2-yl)-1-(5-fluoro-2-trifluoromethylbenzyl)-2-hydroxypropyl]-carbamic acid tert-butyl ester (0.07 g, 0.16 mmol) gives the title compound.
$^1$H NMR (400 MHz, DMSO-d6) δ 1.35 (s, 9H), 3.02-3.18 (m, 3H), 3.20-3.28 (m, 1H), 3.50-3.58 (m, 1H), 4.38-4.42 (m, 1H), 7.30-7.38 (m, 1H), 7.50-7.60 (m, 2H), 7.78-7.82 (m, 1H), 7.98-8.03 (m, 1H), 8.15 (br, 2H), 8.30 (s, 1H), 8.64-8.70 (m, 1H).
MS (m/e): 428 (M+1).

EXAMPLE 11

2-[(2SR,3RS)-3-Amino-4-(2-fluoro-5-methylphenyl)-2-hydroxybutyl]-N-tert-butylnicotinamide Dihydrochloride

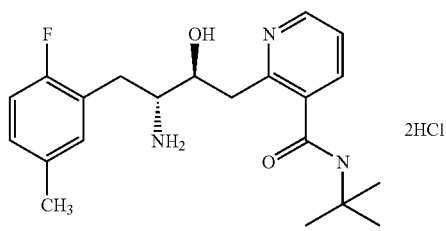

Step A:

[3-(3-tert-Butylcarbamoylpyridn-2-yl)-1-(5-fluoro-2-trifluoromethylbenzyl)-2-oxopropyl]-carbamic acid tert-butyl ester Using general procedure 2 with [2-(2-fluoro-5-methylphenyl)-1-(methoxymethyl-carbamoyl)-ethyl]-carbamic acid tert-butyl ester (2.0 g, 5.9 mmol) gives the title compound.
$^1$HNMR
MS (m/e): 472 (M+1).
Step B:

[(1RS,2SR)-3-(3-tert-Butylcarbamoylpyridin-2-yl)-1-(2-fluoro-5-methylbenzyl)-2-hydroxypropyl]-carbamic acid tert-butyl ester Using general procedure 3 with [3-(3-tert-butylcarbamoylpyridn-2-yl)-1-(2-fluoro-5-methylbenzyl)-2-oxopropyl]-carbamic acid tert-butyl ester (0.9 g, 1.7 mmol) gives the title compound.
$^1$HNMR
MS (m/e): 474 (M+1).
Step C:

2-[(2SR,3RS)-3-Amino-4-(2-fluoro-5-methylphenyl)-2-hydroxybutyl]-N-tert-butylnicotinamide Dihydrochloride Using general deprotection procedure 3 with [3-(3-tert-butylcarbamoylpyridin-2-yl)-1-(2-fluoro-5-methylbenzyl)-2-hydroxypropyl]-carbamic acid tert-butyl ester (0.1 g, 0.21 mmol) gives the title compound.
$^1$H NMR (400 MHz, DMSO-d6) δ 1.38 (s, 9H), 2.26 (s, 3H), 2.80-2.90 (m, 1H), 3.04-3.12 (m, 1H), 3.14-3.22 (m, 2H), 3.48 (br, 1H), 4.26-4.36 (m, 1H), 7.00-7.14 (m, 2H), 7.20-7.24 (m, 1H), 7.66-7.76 (m, 1H), 8.18 (br, 3H), 8.40 (s, 1H), 8.76-7.80 (m, 1H).
MS (m/e): 374 (M+1).

EXAMPLE 12

2-((2S,3R)-3-Amino-2-hydroxy-4-m-tolyl-butyl)-N-tert-butyl-nicotinamide Dihydrochloride

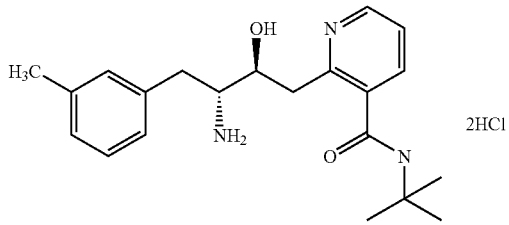

Step A:

[3-(3-tert-Butylcarbamoylpyridn-2-yl)-1-(3-methyl-benzyl)-2-oxopropyl]-carbamic acid tert-butyl ester Using general procedure 2 with [(R)-1-(methoxy-methyl-carbamoyl)-2-m-tolyl-ethyl]-carbamic acid tert-butyl ester (2.0 g, 6.2 mmol) gives the title compound.
<sup>1</sup>HNMR
MS (m/e): 454 (M+1).

Step B:

[(1R,2S)-3-(3-tert-Butylcarbamoylpyridin-2-yl)-1-(3-methylbenzyl)-2-hydroxypropyl]-carbamic acid tert-butyl ester Using general procedure 3 with [3-(3-tert-butylcarbam-oylpyridn-2-yl)-1-(3-methylbenzyl)-2-oxopropyl]-carbamic acid tert-butyl ester (1.7 g, 3.6 mmol) gives the title compound.
<sup>1</sup>HNMR
MS (m/e): 456 (M+1).

Step C:

2-((2S,3R)-3-Amino-2-hydroxy-4-m-tolyl-butyl)-N-tert-butyl-nicotinamide Dihydrochloride Using general deprotection procedure 1 with [(1R,2S)-3-(3-tert-butylcarbamoylpyridin-2-yl)-1-(3-methylbenzyl)-2-hydroxypropyl]-carbamic acid tert-butyl ester (0.65 g, 1.4 mmol) gives the title compound.
<sup>1</sup>H NMR (400 MHz, DMSO-d6) δ 1.38 (s, 9H), 2.26 (s, 3H), 2.80-2.86 (m, 1H), 3.00-3.04 (m, 1H), 3.10-3.16 (m, 2H), 3.38-3.46 (m, 1H), 4.24-4.30 (m, 1H), 7.02-7.08 (m, 1H), 7.10-7.22 (m, 3H), 7.60-7.68 (m, 1H), 8.00-8.18 (m, 3H), 8.38 (s, 1H), 8.72-8.77 (m, 1H).
MS (m/e): 356 (M+1).

EXAMPLE 13

2-((2S,3R)-3-Amino-2-hydroxy-4-o-tolyl-butyl)-N-tert-butyl-nicotinamide Dihydrochloride

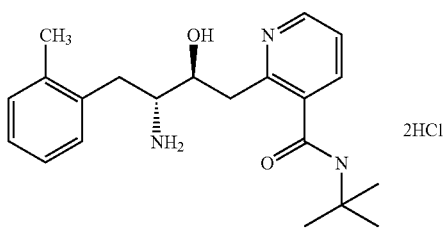

Step A:

[3-(3-tert-Butylcarbamoylpyridn-2-yl)-1-(2-methyl-benzyl)-2-oxopropyl]-carbamic acid tert-butyl ester Using general procedure 2 with [(R)-1-(methoxy-methyl-carbamoyl)-2-o-tolyl-ethyl]-carbamic acid tert-butyl ester (1.0 g, 3.0 mmol) gives the title compound.
<sup>1</sup>HNMR
MS (m/e): 454 (M+1).

Step B:

[(1R,2S)-3-(3-tert-Butylcarbamoylpyridin-2-yl)-1-(3-methylbenzyl)-2-hydroxypropyl]-carbamic acid tert-butyl ester Using general procedure 3 with [3-(3-tert-butylcarbam-oylpyridn-2-yl)-1-(2-methylbenzyl)-2-oxopropyl]-carbamic acid tert-butyl ester (1.4 g, 3.1 mmol) gives the title compound.
<sup>1</sup>HNMR
MS (m/e): 456 (M+1).

Step C:

2-((2S,3R)-3-Amino-2-hydroxy-4-o-tolyl-butyl)-N-tert-butyl-nicotinamide Dihydrochloride Using general deprotection procedure 1 with [(1R,2S)-3-(3-tert-butylcarbamoylpyridin-2-yl)-1-(2-methylbenzyl)-2-hydroxypropyl]-carbamic acid tert-butyl ester (0.58 g, 1.3 mmol) gives the title compound.
1H NMR (400 MHz, DMSO-d6) δ 1.38 (s, 9H), 2.26 (s, 3H), 2.80-2.88 (m, 1H), 3.02-3.16 (m, 3H), 3.40-3.52 (m, 1H), 4.28-4.38 (m, 1H), 7.10-7.20 (m, 3H), 7.24-7.30 (m, 1H), 7.50-7.58 (m, 1H), 8.00 (s, br, 3H), 8.30 (s, 1H), 8.64-8.70 (m, 1H).
MS (m/e): 356 (M+1).

EXAMPLE 14

2-[(2S,3R)-3-Amino-4-(4-chloro-phenyl)-2-hydroxy-butyl]-N-tert-butyl-nicotinamide Dihydrochloride

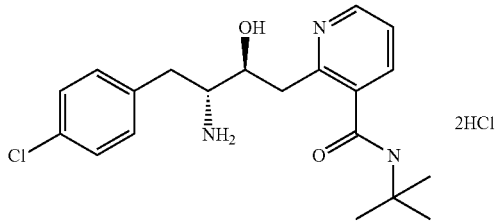

Step A:

[3-(3-tert-Butylcarbamoylpyridn-2-yl)-1-(4-chlorobenzyl)-2-oxopropyl]-carbamic acid tert-butyl ester Using general procedure 2 with [(R)-2-(4-chloro-phenyl)-1-(methoxy-methyl-carbamoyl)-ethyl]-carbamic acid tert-butyl ester (1.5 g, 4.4 mmol) gives the title compound.
<sup>1</sup>HNMR
MS (m/e): 474 (M+1).

Step B:

[(1R,2S)-3-(3-tert-Butylcarbamoylpyridin-2-yl)-1-(4-chlorobenzyl)-2-hydroxypropyl]-carbamic acid tert-butyl ester Using general procedure 3 with [3-(3-tert-butylcarbamoylpyridn-2-yl)-1-(4-chlorobenzyl)-2-oxopropyl]-carbamic acid tert-butyl ester (1.1 g, 2.4 mmol) gives the title compound.
¹HNMR
MS (m/e): 476 (M+1).

Step C:

2-[(2S,3R)-3-Amino-4-(4-chloro-phenyl)-2-hydroxybutyl]-N-tert-butyl-nicotinamide Dihydrochloride Using general deprotection procedure 1 with [(1R,2S)-3-(3-tert-Butylcarbamoylpyridin-2-yl)-1-(4-chlorobenzyl)-2-hydroxypropyl]-carbamic acid tert-butyl ester (0.42 g, 0.88 mmol) gives the title compound.
¹HNMR (400 MHz, DMSO-d6) δ 1.38 (s, 9H), 2.80-2.90 (m, 1H), 3.02-3.12 (m, 3H), 3.37-3.44 (m, 1H), 4.26-4.34 (m, 1H), 7.39 (s, 4H), 7.52-7.60 (m, 1H), 8.00-8.06 (s, br, 3H), 8.37 (s, 1H), 8.70-8.76 (m, 1H).
MS (m/e): 376 (M+1).

EXAMPLE 15

2-((2SR,3RS)-3-Amino-2-hydroxy-4-pyridin-2-yl-butyl)-N-tert-butyl-nicotinamide Trihydrochloride

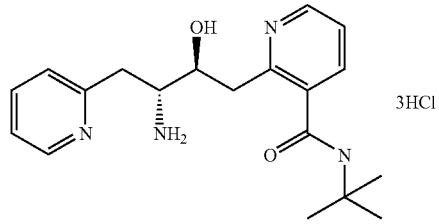

Step A:

[(RS)-3-(3-tert-Butylcarbamoyl-pyridin-2-yl)-2-oxo-1-pyridin-2-ylmethyl-propyl]-carbamic acid tert-butyl ester Using general procedure 2 with [(R)-1-(methoxy-methyl-carbamoyl)-2-pyridin-2-yl-ethyl]-carbamic acid tert-butyl ester (1.0 g, 3.2 mmol) gives the title compound.
¹HNMR
MS (m/e): 441 (M+1).

Step B:

[(1RS,2SR)-3-(3-tert-Butylcarbamoyl-pyridin-2-yl)-2-hydroxy-1-pyridin-2-ylmethyl-propyl]-carbamic acid tert-butyl ester Using general procedure 3 with [(RS)-3-(3-tert-butylcarbamoyl-pyridin-2-yl)-2-oxo-1-pyridin-2-ylmethyl-propyl]-carbamic acid tert-butyl ester (1.05 g, 2.4 mmol) followed by general purification method 3 gives the title compound.
¹HNMR
MS (m/e): 443 (M+1).

Step C:

2-((2SR,3RS)-3-Amino-2-hydroxy-4-pyridin-2-yl-butyl)-N-tert-butyl-nicotinamide Trihydrochloride Using general deprotection procedure 1 with [(1RS,2SR)-3-(2-tert-butylcarbamoylphenyl)-2-hydroxy-1-pyridin-2-yl-methylpropyl]-carbamic acid tert-butyl ester (0.3 g, 0.7 mmol) gives the title compound.
1H NMR (400 MHz, DMSO-d6) δ 1.38 (s, 9H), 3.12-3.20 (m, 1H), 3.22-3.36 (m, 2H), 3.50-3.57 (m, 1H), 3.82-3.90 (m, 1H), 4.36-4.42 (m, 1H), 7.60-7.64 (m, 1H), 7.76-7.80 (m, 1H), 7.88-7.96 (m, 1H), 8.06-8.14 (m, 1H), 8.30-8.38 (m, 1H), 8.37 (br, 3H), 8.70-8.76 (m, 1H), 8.77-8.80 (m, 1H).
MS (m/e): 343 (M+1).

EXAMPLE 16

2-[(2S,3R)-3-Amino-4-(2-fluoro-phenyl)-2-hydroxybutyl]-N-methyl-nicotinamide dihydrochloride

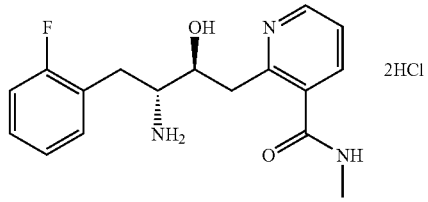

Step A:

(4R,5S)-4-(2-Fluoro-benzyl)-2,2-dimethyl-5-(3-methylcarbamoyl-pyridin-2-ylmethyl)-oxazolidine-3-carboxylic acid tert-butyl ester Using general reaction procedure 5 with 2-[(4R,5S)-3-tert-butoxycarbonyl-4-(2-fluoro-benzyl)-2,2-dimethyl-oxazolidin-5-ylmethyl]-nicotinic acid (0.5 g, 1.1 mmol) and methyl amine hydrochloride (0.38 mL, 5.6 mmol) gives the title compound.
¹HNMR
MS (m/e): 458 (M+1).

Step B:

2-[(2S,3R)-3-Amino-4-(2-fluoro-phenyl)-2-hydroxybutyl]-N-methyl-nicotinamide dihydrochloride Using general deprotection procedure 4 with 4-(2-fluoro-benzyl)-2,2-dimethyl-5-(3-methylcarbamoyl-pyridin-2-ylmethyl)-oxazolidine-3-carboxylic acid tert-butyl ester (0.41 g, 0.9 mmol) followed by general purification method 1 gives the title compound.
¹HNMR (400 MHz, DMSO-d6) δ 2.78 (d, J=4.8 Hz, 3H), 2.89 (dd, J=8.4, 14.8 Hz, 1H), 3.12 (dd, J=4.8, 14.8 Hz, 1H), 3.16 (d, J=7.2 Hz, 2H), 3.40-3.50 (m, 1H), 4.25-4.29 (m, 1H), 7.13-7.20 (m, 2H), 7.29-7.34 (m, 1H), 7.43 (dd, J=7.6, 8.8 Hz, 1H), 7.54-7.60 (m, 1H), 8.03-8.18 (m, 4H), 8.69 (d, J=5.2 Hz, 1H), 8.72 (d, J=4.0 Hz, 1H).
MS (m/e): 318 (M+1).

EXAMPLE 17

2-[(2S,3R)-3-Amino-4-(2-fluoro-phenyl)-2-hydroxy-butyl]-N-(2,2,2-trifluoro-ethyl)-nicotinamide Dihydrochloride

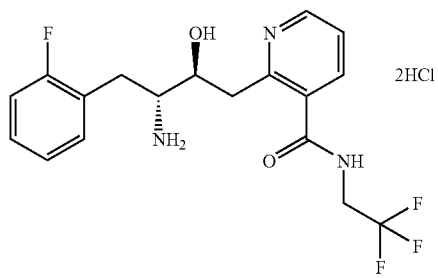

Step A:

(4R,5S)-4-(2-Fluoro-benzyl)-2,2-dimethyl-5-[3-(2,2,2-trifluoro-ethylcarbamoyl)-pyridin-2-ylmethyl]-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.5 g, 1.1 mmol) and 2,2,2-trifluoromethylamine (0.44 mL, 5.6 mmol) gives the title compound.
$^1$HNMR
MS (m/e): 526 (M+1).

Step B:

2-[(2S,3R)-3-Amino-4-(2-fluoro-phenyl)-2-hydroxy-butyl]-N-(2,2,2-trifluoro-ethyl)-nicotinamide Dihydrochloride Using general deprotection procedure 4 with (4R,5S)-4-(2-fluoro-benzyl)-2,2-dimethyl-5-[3-(2,2,2-trifluoro-ethylcarbamoyl)-pyridin-2-ylmethyl]-oxazolidine-3-carboxylic acid tert-butyl ester (0.44 g, 0.84 mmol) followed by general purification method 1 gives the title compound.
$^1$HNMR (400 MHz, DMSO-d6) δ 2.87 (dd, J=8.8, 14.8 Hz, 1H), 3.05-3.17 (m, 3H), 4.03-4.17 (m, 2H), 3.38-3.48 (m, 1H), 7.13-7.20 (m, 2H), 4.34-4.38 (m, 1H), 7.28-7.34 (m, 1H), 7.37 (dd, J=8.0, 11.2 Hz, 1H), 7.46 (dd, J=4.0, 8.0 Hz, 1H), 7.88 (d, 8.0 Hz, 1H), 8.05 (bs, 3H), 8.66 (dd, J=1.6, 5.2 Hz, 1H), 9.31 (t, J=6.4 Hz, 1H).
MS (m/e): 386 (M+1).

EXAMPLE 18

2-[(2S,3R)-3-Amino-4-(2-fluoro-phenyl)-2-hydroxy-butyl]-N-phenyl-nicotinamide Dihydrochloride

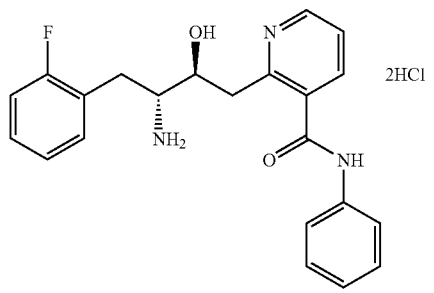

Step A:

(4R,5S)-4-(2-Fluoro-benzyl)-2,2-dimethyl-5-(3-phenylcarbamoyl-pyridin-2-ylmethyl)-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.5 g, 1.1 mmol) and aniline (0.52 mL, 5.6 mmol) gives the title compound.
$^1$HNMR
MS (m/e): 520 (M+1).

Step B:

2-[(2S,3R)-3-Amino-4-(2-fluoro-phenyl)-2-hydroxy-butyl]-N-phenyl-nicotinamide Dihydrochloride Using general deprotection procedure 4 with (4R,5S)-4-(2-fluoro-benzyl)-2,2-dimethyl-5-(3-phenylcarbamoyl-pyridin-2-ylmethyl)-oxazolidine-3-carboxylic acid tert-butyl ester (0.36 g, 0.69 mmol) followed by general purification method 1 gives the title compound.
$^1$HNMR (400 MHz, DMSO-d6) δ 2.88 (dd, J=8.4, 14.4, 1H), 3.10 (dd, J=5.2, 14.4 Hz, 1H), 3.14-3.24 (m, 2H), 3.41-3.50 (m, 1H), 4.35-4.40 (m, 1H), 7.06-7.25 (m, 3H), 7.24-7.30 (m, 1H), 7.32-7.40 (m, 3H), 7.55 (dd, J=5.2, 7.6 Hz, 1H), 7.73 (d, J=8.4 Hz, 2H), 8.05 (bs, 3H), 8.11 (d, J=7.6 Hz, 1H), 8.70 (dd, J=1.2, 5.2 Hz, 1H), 10.65 (s, 1H).
MS (m/e): 380 (M+1).

EXAMPLE 19

2-[(2S,3R)-3-Amino-4-(2-fluoro-phenyl)-2-hydroxy-butyl]-N-phenethyl-nicotinamide Dihydrochloride

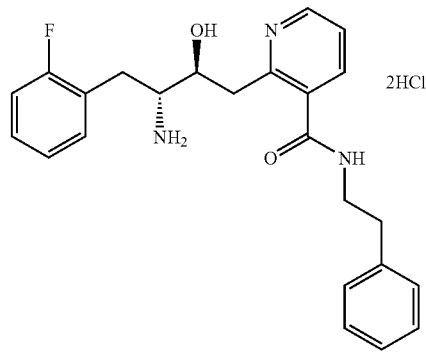

Step A:

(4R,5S)-4-(2-Fluoro-benzyl)-2,2-dimethyl-5-(3-phenethylcarbamoyl-pyridin-2-ylmethyl)-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.5 g, 1.1 mmol) and phenethylamine (0.71 mL, 5.6 mmol) gives the title compound.
$^1$HNMR
MS (m/e): 548 (M+1).

Step B:

2-[(2S,3R)-3-Amino-4-(2-fluoro-phenyl)-2-hydroxy-butyl]-N-phenethyl-nicotinamide Dihydrochloride Using general deprotection procedure 4 with (4R,5S)-4-(2-fluoro-benzyl)-2,2-dimethyl-5-(3-phenethylcarbamoyl-pyridin-2-ylmethyl)-oxazolidine-3-carboxylic acid tert-butyl ester (0.32 g, 0.58 mmol) followed by general purification method 1 gives the title compound.
¹HNMR (400 MHz, DMSO-d6) δ 2.80-2.89 (m, 3H), 3.00-3.10 (m, 3H), 3.38-3.52 (m, 3H), 4.26-4.30 (m, 1H), 7.10-7.22 (m, 3H), 7.23-7.34 (m, 5H), 7.37-7.47 (m, 2H), 7.83 (d, J=7.2 Hz, 1H), 8.01 (bs, 3H), 8.63 (d, J=3.6 Hz, 1H), 8.80 (t, J=6 Hz, 1H).
MS (m/e): 408 (M+1).

EXAMPLE 20

2-[(2S,3R)-3-Amino-4-(2-fluoro-phenyl)-2-hydroxy-butyl]-N,N-dimethyl-nicotinamide Dihydrochloride

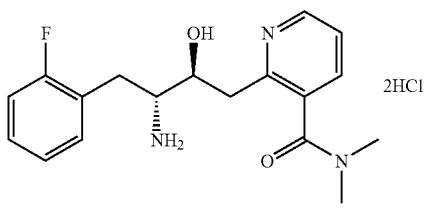

Step A:

(4R,5S)-5-(3-Dimethylcarbamoyl-pyridin-2-ylmethyl)-4-(2-fluoro-benzyl)-2,2-dimethyl-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.15 g, 0.34 mmol) and dimethylamine hydrochloride (0.17 g, 1.7 mmol) and substituting EDC (1.6 equiv) and HOBt (2.2 equiv) for benzotriazole-1-yl-oxy-tris-pyrrolidino-phosphonium hexafluorophosphate gives the title compound.
¹HNMR
MS (m/e): 472 (M+1).

Step B:

2-[(2S,3R)-3-Amino-4-(2-fluoro-phenyl)-2-hydroxy-butyl]-N,N-dimethyl-nicotinamide Dihydrochloride Using general deprotection procedure 4 with (4R,5S)-5-(3-dimethylcarbamoyl-pyridin-2-ylmethyl)-4-(2-fluoro-benzyl)-2,2-dimethyl-oxazolidine-3-carboxylic acid tert-butyl ester (0.03 g, 0.07 mmol) followed by general purification method 1 gives the title compound.
¹HNMR (400 MHz, DMSO-d6) δ 2.79 (s, 3H), 2.85-3.00 (m, 3H), 3.01 (s, 3H), 3.09 (dd, J=6.0, 14.8 Hz, 1H), 3.45-3.48 (m, 1H), 4.30-4.34 (m, 1H), 7.14-7.20 (m, 2H), 7.28-7.35 (m, 1H), 7.42 (dd, J=6.4, 8.0 Hz, 1H), 7.45-7.53 (m, 1H), 7.90 (bd, J=7.2 Hz, 1H), 8.11 (bs, 3H), 8.55 (d, J=5.2 Hz, 1H).
MS (m/e): 332 (M+1).

EXAMPLE 21

{2-[(2S,3R)-3-Amino-4-(2-fluoro-phenyl)-2-hydroxy-butyl]-pyridin-3-yl}-piperidin-1-yl-methanone Dihydrochloride

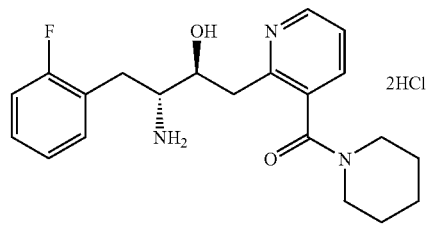

Step A:

(4R,5S)-4-(2-Fluoro-benzyl)-2,2-dimethyl-5-[3-(piperidine-1-carbonyl)-pyridin-2-ylmethyl]-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.15 g, 0.34 mmol) and dimethylamine hydrochloride (0.17 mL, 1.7 mmol) gives the title compound.
¹HNMR
MS (m/e): 512 (M+1).

Step B:

{2-[(2S,3R)-3-Amino-4-(2-fluoro-phenyl)-2-hydroxy-butyl]-pyridin-3-yl}-piperidin-1-yl-methanone Dihydrochloride Using general deprotection procedure 4 with (4R,5S)-4-(2-fluoro-benzyl)-2,2-dimethyl-5-[3-(piperidine-1-carbonyl)-pyridin-2-ylmethyl]-oxazolidine-3-carboxylic acid tert-butyl ester (0.11 g, 0.22 mmol) followed by general purification method 1 gives the title compound.
¹HNMR (400 MHz, DMSO-d6) δ 1.36-1.46 (m, 2H), 1.51-1.63 (m, 4H), 2.83-3.00 (m, 3H), 3.04-3.17 (m, 3H), 3.42-3.76 (m, 3H), 4.23-4.40 (m, 1H), 7.14-7.19 (m, 2H), 7.28-7.35 (m, 1H), 7.39 (dd, J=7.6, 8.0 Hz, 1H), 7.46-7.52 (m, 1H), 7.83 (d, J=6.4 Hz, 1H), 8.07 (bs, 3H), 8.63 (d, J=4.4 Hz, 1H).
MS (m/e): 372 (M+1).

EXAMPLE 22

2-[(2S,3R)-3-Amino-4-(2-fluoro-phenyl)-2-hydroxy-butyl]-N-(2-methoxy-benzyl)-nicotinamide Dihydrochloride

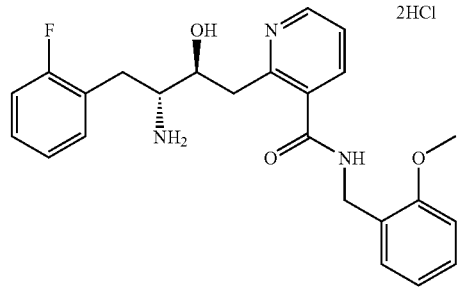

Step A:

(4R,5S)-4-(2-Fluoro-benzyl)-5-[3-(2-methoxy-benzylcarbamoyl)-pyridin-2-ylmethyl]-2,2-dimethyl-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.15 g, 0.34 mmol) and 2-methoxy-benzylamine (0.22 mL, 1.7 mmol) gives the title compound.
¹HNMR
MS (m/e): 564 (M+1).

Step B:

2-[(2S,3R)-3-Amino-4-(2-fluoro-phenyl)-2-hydroxy-butyl]-N-(2-methoxy-benzyl)-nicotinamide Dihydrochloride Using general deprotection procedure 4 with (4R,5S)-4-(2-fluoro-benzyl)-5-[3-(2-methoxy-benzylcarbamoyl)-pyridin-2-ylmethyl]-2,2-dimethyl-oxazolidine-3-carboxylic acid tert-butyl ester (0.14 g, 0.24 mmol) followed by general purification method 1 gives the title compound.
¹HNMR (400 MHz, DMSO-d6) δ 2.83 (dd, J=8.8, 14.4 Hz, 1H), 3.04 (dd, J=4.8, 14.4 Hz, 1H), 3.10-3.21 (m, 2H), 3.38-3.46 (m, 1H), 3.80 (s, 3H), 3.90-4.33 (m, 1H), 4.43 (d, J=5.6 Hz, 2H), 6.89 (dd, J=7.6, 8.0 Hz, 1H), 6.97 (d, J=8.4 Hz, 1H), 7.12-7.40 (m, 6H), 7.50-7.55 (m, 1H), 7.98-8.18 (m, 4H), 8.68 (d, J=4.0 Hz, 1H), 9.07 (t, J=5.6 Hz, 1H).
MS (m/e): 424 (M+1).

EXAMPLE 23

2-[(2S,3R)-3-Amino-4-(2-fluoro-phenyl)-2-hydroxy-butyl]-N-(1-methyl-1-phenyl-ethyl)-nicotinamide Dihydrochloride

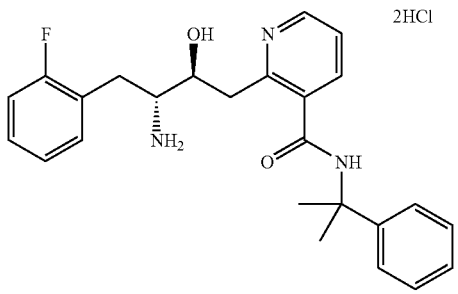

Step A:

(4R,5S)-4-(2-Fluoro-benzyl)-2,2-dimethyl-5-[3-(1-methyl-1-phenyl-ethylcarbamoyl)-pyridin-2-ylmethyl]-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.15 g, 0.34 mmol) and 1-methyl-1-phenyl-ethylamine (0.23 mL, 1.7 mmol) gives the title compound.
¹HNMR
MS (m/e): 562 (M+1).

Step B:

2-[(2S,3R)-3-Amino-4-(2-fluoro-phenyl)-2-hydroxy-butyl]-N-(1-methyl-1-phenyl-ethyl)-nicotinamide Dihydrochloride Using general deprotection procedure 4 with (4R,5S)-4-(2-Fluoro-benzyl)-2,2-dimethyl-5-[3-(1-methyl-1-phenyl-ethylcarbamoyl)-pyridin-2-ylmethyl]-oxazolidine-3-carboxylic acid tert-butyl ester (0.14 g, 0.24 mmol) followed by general purification method 1 gives the title compound.
¹HNMR (400 MHz, DMSO-d6) δ 1.65 (s, 6H), 2.80 (dd, J=9.2, 14.4 Hz, 1H), 2.97-3.14 (m, 3H), 3.35-3.42 (m, 1H), 4.27-4.32 (m, 1H), 7.10-7.20 (m, 3H), 7.23-7.39 (m, 4H), 7.43 (d, J=8.0 Hz, 1H), 7.52-7.60 (m, 1H), 7.98-8.07 (m, 3H), 8.08-8.14 (m, 1H), 8.69 (d, J=5.6 Hz), 8.95 (bs, 1H).
MS (m/e): 422 (M+1).

EXAMPLE 24

2-[(2S,3R)-3-Amino-4-(2-fluoro-phenyl)-2-hydroxy-butyl]-N-ethyl-nicotinamide Dihydrochloride

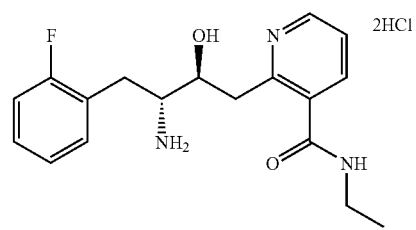

Step A:

(4R,5S)-5-(3-Ethylcarbamoyl-pyridin-2-ylmethyl)-4-(2-fluoro-benzyl)-2,2-dimethyl-oxazolidine-3-carboxylic acid tert-butyl ester Using general reaction procedure 5 with 2-[(2S,3R)-3-tert-butoxycarbonyl-4-(2-fluoro-benzyl)-2,2-dimethyl-oxazolidin-5-ylmethyl]-nicotinic acid (0.15 g, 0.34 mmol) and ethylamine hydrochloride (0.11 g, 1.69 mmol) and substituting EDC (1.6 equiv) and HOBt (2.2 equiv) for benzotriazole-1-yl-oxy-tris-pyrrolidino-phosphonium hexafluorophosphate gives the title compound.
¹HNMR
MS (m/e): 472 (M+1).

Step B:

2-[(2S,3R)-3-Amino-4-(2-fluoro-phenyl)-2-hydroxy-butyl]-N-ethyl-nicotinamide Dihydrochloride Using general deprotection procedure 4 with (4R,5S)-5-(3-ethylcarbamoyl-pyridin-2-ylmethyl)-4-(2-fluoro-benzyl)-2,2-dimethyl-oxazolidine-3-carboxylic acid tert-butyl ester (0.14 g, 0.24 mmol) followed by general purification method 1 gives the title compound.
¹HNMR (400 MHz, DMSO-d6) δ 1.22 (t, J=7.2 Hz, 3H), 2.88 (dd, J=8.0, 14.4 Hz, 1H), 3.09-3.14 (m, 3H), 3.23-3.30 (m, 2H), 3.44-3.50 (m, 1H), 4.26-4.30 (m, 1H), 7.13-7.19 (m, 2H), 7.28-7.34 (m, 1H), 7.38-7.45 (m, 1H), 7.49-7.55 (m, 1H), 7.97-8.10 (m, 4H), 8.67 (m, 1H), 8.73 (t, J=5.6 Hz, 1H).
MS (m/e): 332 (M+1).

EXAMPLE 25

2-[(S)-3-Amino-4-(2-fluoro-phenyl)-butyl]-N-tert-butyl-nicotinamide Dihydrochloride

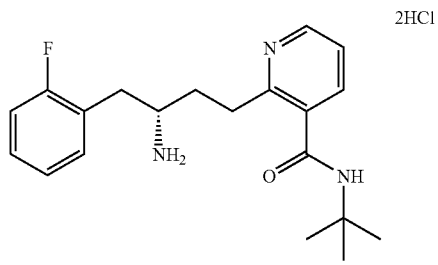

Step A:

2-[(E)-(R)-3-Dibenzylamino-4-(2-fluoro-phenyl)-but-1-enyl]-nicotinic acid methyl ester To a suspension of (3-ethoxycarbonyl-pyridin-2-ylmethyl)-trimethyl-phosphonium bromide (0.9 g, 2.6 mmol) in 50 mL of ether is added potassium tert-butoxide (0.32 g, 2.9 mmol) and the reaction is heated at reflux for 30 minutes. The reaction is then cooled to −78° C., a solution of (R)-2-dibenzylamino-3-(2-fluoro-phenyl)-propionaldehyde (1.8 g, 3.5 mmol) in 10 mL of ether is added, and the reaction is allowed to stir at room temperature for 16 hours. The reaction is then concentrated under reduced pressure and purification of the resultant residue by silica gel flash column chromatography gives the title compound.
¹HNMR
MS (m/e): 495 (M+1).

Step B:

2-[(E)-(R)-3-Dibenzylamino-4-(2-fluoro-phenyl)-but-1-enyl]-nicotinic acid

To a solution of 2-[(E)-(R)-3-dibenzylamino-4-(2-fluoro-phenyl)-but-1-enyl]-nicotinic acid methyl ester (0.7 g, 1.4 mmol) in 5 mL of a 1:1 dioxane:water solution is added lithium hydroxide (0.07 g, 2.8 mmol). After stirring for 24 hours, the reaction is diluted with water and is neutralized by addition of 1N HCl. Filtration gives the title compound.
¹HNMR
MS (m/e): 467 (M+1).

Step C:

N-tert-Butyl-2-[(E)-(R)-3-dibenzylamino-4-(2-fluoro-phenyl)-but-1-enyl]-nicotinamide Using general procedure 5 with 2-[(E)-(R)-3-dibenzylamino-4-(2-fluoro-phenyl)-but-1-enyl]-nicotinic acid (0.64 g, 1.4 mmol) and tert-butylamine (0.73 mL, 1.5 mmol) gives the title compound.
¹HNMR
MS (m/e): 522 (M+1).

Step D:

2-[(S)-3-Amino-4-(2-fluoro-phenyl)-butyl]-N-tert-butyl-nicotinamide Dihydrochloride To a solution of N-tert-Butyl-2-[(E)-(R)-3-dibenzylamino-4-(2-fluoro-phenyl)-but-1-enyl]-nicotinamide (0.6 g, 1.2 mmol) in 10 mL of ethanol is added 600 mg of 20% palladium hydroxide. The reaction vessel is evacuated and filled with hydrogen to a pressure of 50 psi. After stirring for 16 hours, the flask is vented to release the hydrogen. The reaction mixture is filtered through a pad of celite and is concentrated under reduced pressure. Purification by silica gel flash column chromatography followed by general purification method 1 gives the title compound.
¹HNMR (400 MHz, DMSO-d6) δ 1.31 (s, 9H), 1.91-2.02 (m, 2H), 2.88-3.08 (m, 4H), 3.33-3.43 (m, 1H), 7.13-7.19 (m, 2H), 7.28-7.37 (m, 2H), 7.48-7.55 (m, 1H), 7.90-7.95 (m, 1H), 8.23 (bs, 4H), 8.61 (d, J=4.4 Hz, 1H).
MS (m/e): 344 (M+1).

EXAMPLE 26

2-[(2S,3R)-3-Amino-4-(2,5-difluoro-phenyl)-2-hydroxy-butyl]-N-tert-butyl-6-trimethyl-nicotinamide Dihydrochloride

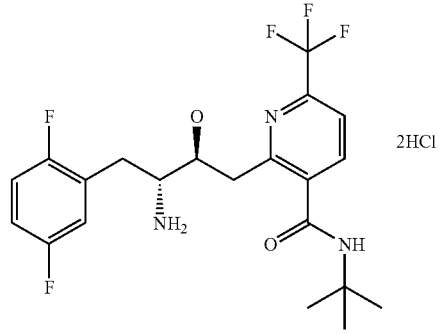

Step A:

[(R)-3-(3-tert-Butylcarbamoyl-6-trifluoromethyl-pyridin-2-yl)-1-(2,5-difluoro-benzyl)-2-oxo-propyl]-carbamic acid tert-butyl ester To a solution of N-tert-butyl-2-methyl-6-trifluoromethyl-nicotinamide (2.3 g, 8.7 mmol) and TMEDA (2.7 mL, 17 mmol) in 130 mL of THF at −68° C. is slowly added LDA (2M, 8.7 mL, 17.4 mmol). The reaction temperature is maintained at −68° C., then warmed to −20° C. and is then immediately re-cooled to −68° C. To the reaction is added a solution of [(R)-2-(2,5-difluoro-phenyl)-1-(methoxy-methyl-carbamoyl)-ethyl]-carbamic acid tert-butyl ester (1 g, 2.9 mmol) in 20 mL of THF over a period of 10 minutes. The reaction is allowed to stir an additional 20 min after which the reaction is poured into 150 mL of a chilled 3% (w/v) solution of NaHSO4 in water. The solution is adjusted to pH7 by addition of pH7 buffer and the product is extracted into dichloromethane. The organic phase is dried over sodium sulfate, filtered, and concentrated under reduced pressure. Purification of the resultant residue by silica gel flash column chromatography provides the title compound.
¹HNMR
MS (m/e): 483 (M+1−C₅H₉O₂).

Step B:

[(1R,2S)-3-(3-tert-Butylcarbamoyl-6-trifluoromethyl-pyridin-2-yl)-1-(2,5-difluoro-benzyl)-2-hydroxy-propyl]-carbamic acid tert-butyl ester Using general procedure 3 with [(R)-3-(3-tert-butylcarbamoyl-6-trifluoromethyl-pyridin-2-yl)-1-(2,5-difluoro-benzyl)-2-oxo-propyl]-carbamic acid tert-butyl ester (0.55 g, 2.8 mmol) gives the title compound.
¹HNMR
MS (m/e): 546 (M+1).

Step C:

2-[(2S,3R)-3-Amino-4-(2,5-difluoro-phenyl)-2-hydroxy-butyl]-N-tert-butyl-6-trifluoromethyl-nicotinamide Dihydrochloride Using general deprotection method 1 with [(1R,2S)-3-(3-tert-butylcarbamoyl-6-trifluoromethyl-pyridin-2-yl)-1-(2,5-difluoro-benzyl)-2-hydroxy-propyl]-carbamic acid tert-butyl ester (0.26 g, 0.4 mmol) gives the title compound.

¹HNMR (400 MHz, DMSO-d6) δ 1.36 (s, 9H), 2.88 (dd, J=9.6, 15.2 Hz, 1H), 3.03-3.17 (m, 3H), 3.50-3.59 (m, 1H), 4.32-4.39 (m, 1H), 5.80 (d, 5.6 Hz, 1H), 7.11-7.18 (m, 1H), 7.19-7.25 (m, 1H), 7.25-7.32 (m, 1H), 7.82 (d, J=7.6 Hz, 1H), 7.94-8.02 (m, 4H), d 8.25 (bs, 1H).

MS (m/e): 446 (M+1).

EXAMPLE 27

(2S,3R)-3-Amino-4-(2,-fluoro-phenyl)-1-pyridin-2-yl-butan-2-ol Dihydrochloride

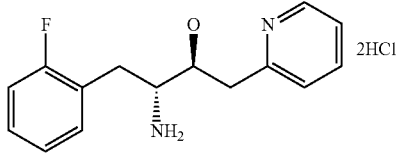

Step A:

[(R)-1-(2-Fluoro-benzyl)-2-oxo-3-pyridin-2-yl-propyl]-carbamic acid tert-butyl ester To a solution of 2-picoline (0.54 mL, 5.5 mmol) in 20 mL of THF at −52° C. is slowly added a 1.5 M solution of n-butyllithium in hexanes (3.6 mL, 5.5 mmol). The reaction is then warmed to 15° C. and is then immediately re-cooled to −52° C. To the reaction is added a solution of [(R)-2-(2-fluoro-phenyl)-1-(methoxy-methyl-carbamoyl)-ethyl]-carbamic acid tert-butyl ester (0.6 g, 1.8 mmol) in 4 mL of THF. The reaction is then is poured into 8 mL of a 2M solution of NaHSO4 in water. The solution is adjusted to pH7 by addition of pH7 buffer and the product is extracted into ether. The organic phase is dried over sodium sulfate, filtered, and concentrated under reduced pressure to give the title compound.

¹HNMR

MS (m/e): 381 (M+Na)

Step B:

[(1R,2S)-1-(2-Fluoro-benzyl)-2-hydroxy-3-pyridin-2-yl-propyl]-carbamic acid tert-butyl ester Using general procedure 3 with [(R)-1-(2-fluoro-benzyl)-2-oxo-3-pyridin-2-yl-propyl]-carbamic acid tert-butyl ester (0.4 g, 1.2 mmol) gives the title compound.

¹HNMR

MS (m/e): 305 (M−C₄H₉).

Step C:

(2S,3R)-3-Amino-4-(2-fluoro-phenyl)-1-pyridin-2-yl-butan-2-ol Dihydrochloride Using general deprotection method 4 with [(1R,2S)-1-(2-fluoro-benzyl)-2-hydroxy-3-pyridin-2-yl-propyl]-carbamic acid tert-butyl ester (0.24 g, 0.66 mmol) followed by general purification method B gives the title compound ¹HNMR (400 MHz, DMSO-d6) δ 2.90 (dd, J=8.4, 14.9 Hz, 1H), 3.08 (dd, J=10.1, 14.3 Hz, 1H), 3.14 (dd, J=5.3, 9.2 Hz, 1H), 3.26 (br m, 1H), 3.45 (br, 1H), 4.2 (br m, 1H), 7.16-7.21 (m, 2H), 7.31 (m, 1H), 7.45 (m, 1H), 7.7 (br, 2H), 8.15 (br, 4H), 8.26 (br, 1H), 8.73 (br d, J=5.3 Hz, 1H).

MS (m/e): 261 (M+1).

EXAMPLE 28

2-[(2S,3R)-3-Amino-4-(2-fluoro-phenyl)-2-hydroxy-butyl]-N-tert-butyl-nicotinamide Dihydrochloride

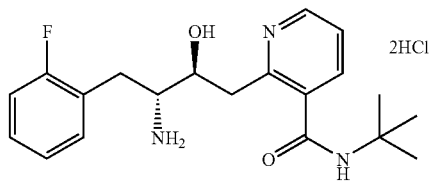

Step A:

[(R)-3-(3-tert-Butylcarbamoyl-pyridin-2-yl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (19 g, 58 mmol) gives the title compound.

¹HNMR

MS (m/e): 402 (M+1−C₄H₉)

Step B:

[(1R,2S)-3-(3-tert-Butylcarbamoyl-pyridin-2-yl)-1-(2-fluoro-benzyl)-2-hydroxy-propyl]-carbamic acid tert-butyl ester Using general procedure 3 with [(R)-3-(3-tert-butylcarbamoyl-pyridin-2-yl)-1-(2-fluoro-benzyl)-2-oxo-propyl]-carbamic acid tert-butyl ester (6.5 g, 14 mmol) gives the title compound.

¹HNMR

MS (m/e): 460 (M+1)

Step C:

2-[(2S,3R)-3-Amino-4-(2-fluoro-phenyl)-2-hydroxy-butyl]-N-tert-butyl-nicotinamide Dihydrochloride Using general deprotection procedure 1 and purification method C with [(1R,2S)-3-(3-tert-butylcarbamoyl-pyridin-2-yl)-1-(2-fluoro-benzyl)-2-hydroxy-propyl]-carbamic acid tert-butyl ester (3.2 g, 7.0 mmol) gives the title compound.

¹HNMR (400 MHz, CDCl₃) δ 1.36(s, 9H), 2.86 (dd, J=9.1, 14.6 Hz, 1H), 2.99-3.08 (m, 2H), 3.12 (dd, J=4.4, 14.5 Hz, 1H), 3.41-3.48 (m, 1H), 4.29-4.34 (m, 1H), 7.14-7.20 (m, 2H), 7.29-7.35 (m, 1H), 7.41 (t, J=7.0 Hz, 2H), 7.83 (d, J=7.7 Hz, 1H), 7.95-8.01 (br m, 2H), 8.21 (s, 1H), 8.61 (d, J=5.1 Hz, 1H).

MS (m/e): 360 (M+1).

EXAMPLE 29

2-[(2S,3R)-3-Amino-4-(2-fluoro-phenyl)-2-methoxy-butyl]-N-tert-butyl-nicotinamide

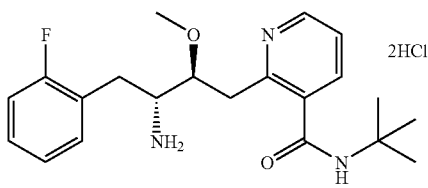

Step A:

[(1R,2S)-3-(3-tert-Butylcarbamoyl-pyridin-2-yl)-1-(2-fluoro-benzyl)-2-methoxy-propyl]-carbamic acid tert-butyl ester To a solution of 2-[(2S,3R)-3-amino-4-(2-fluoro-phenyl)-2-hydroxy-butyl]-N-tert-butyl-butyl-nicotinamide dihydrochloride (0.40 g, 0.92 mmol) in 5 mL of THF is added sodium hydride as a 60% dispersion in mineral oil (0.18 g, 4.6 mmol). The reaction is stirred at room temperature for 1 hour after which time it is cooled to −10° C. and methyl iodide (0.13 mg, 0.92 mmol) is added. The cooling bath is removed and the reaction is allowed to stir an additional 16 hours. To the reaction is added 2.5 mL of a saturated NaHCO$_3$ solution followed by addition of BOC$_2$O (0.40 g, 1.8 mmol). The reaction is allowed to stir for 2 hours at room temperature and is then diluted with water and the products are extracted into dichloromethane. The combined organic layers are dried over sodium sulfate, filtered, and concentrated under reduced pressure. Purification of the resultant crude residue by silica gel flash column chromatography gives the title compound.
$^1$HNMR
MS (m/e): 474 (M+1).

Step B:

2-[(2S,3R)-3-Amino-4-(2-fluoro-phenyl)-2-methoxy-butyl]-N-tert-butyl-nicotinamide Using general deprotection procedure 1 with [(1R,2S)-3-(3-tert-butylcarbamoyl-pyridin-2-yl)-1-(2-fluoro-benzyl)-2-methoxy-propyl]-carbamic acid tert-butyl ester (0.21 g, 0.43 mmol) gives the title compound.
$^1$HNMR
MS (m/e): 374 (M+1).

EXAMPLE 30

2-[(2S,3R)-3-Amino-4-(2-fluoro-phenyl)-2-hydroxybutyl]-N-isopropyl-nicotinamide

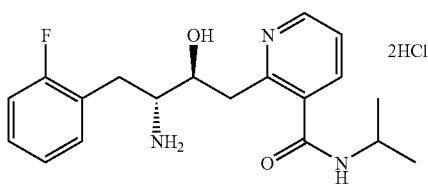

Step A:

[(R)-1-(2-Fluoro-benzyl)-3-(3-isopropylcarbamoyl-pyridin-2-yl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (0.65 g, 2.0 mmol) and substituting N-isopropyl-2-methyl-nicotinamide for N-tert-butyl-2-methyl-nicotinamide gives the title compound.
$^1$HNMR
mass spectrum (m/e): 444 (M+1)

Step B:

[(1R,2S)-1-(2-Fluoro-benzyl)-2-hydroxy-3-(3-isopropylcarbamoyl-pyridin-2-yl)-propyl]-carbamic acid tert-butyl ester Using general procedure 3 with [(R)-1-(2-fluoro-benzyl)-3-(3-isopropylcarbamoyl-pyridin-2-yl)-2-oxo-propyl]-carbamic acid tert-butyl ester (0.38 g, 0.86 mmol) gives the title compound.
$^1$HNMR
mass spectrum (m/e): 446 (M+1)

Step C:

2-[(2S,3R)-3-Amino-4-(2-fluoro-phenyl)-2-hydroxy-butyl]-N-isopropyl-nicotinamide Using general deprotection procedure 5 with [(1R,2S)-1-(2-Fluoro-benzyl)-2-hydroxy-3-(3-isopropylcarbamoyl-pyridin-2-yl)-propyl]-carbamic acid tert-butyl ester (0.16 g, 0.34 mmol) followed by trituration with pentane gives the title compound.
$^1$HNMR (400 MHz, DMSO-d6) δ 1.13 (d, J=6.6 Hz, 3H), 1.14 (d, J=6.6 Hz, 3H), 2.92 (dd, J=5.8, 9.2 Hz, 1H), 2.96 (dd, J=5.8, 8.1 Hz, 1H), 3.08 (d, J=7.1 Hz, 2H), 3.28-3.36 (m, 1H), 3.94-4.02 (m, 1H), 4.02 (qq, J=6.6 Hz, 1H), 4.30 (br., 1H), 7.11-7.16 (m, 3H), 7.27-7.33 (m, 3H), 7.39 (t, J=5.3 Hz, 1H), 7.83 (d, J=7.9 Hz, 1H), 8.02 (br., 3H), 8.53 (d, J=3.5 Hz, 1H), 8.58 (d, J=7.4 Hz, 1H).
mass spectrum (m/e): 346 (M+1)

EXAMPLE 31

N-{2-[(2S,3R)-3-Amino-4-(2,5-difluorophenyl)-2-hydroxybutyl]pyridin-3-yl}acetamide dihydrochloride

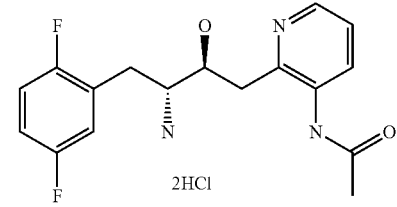

Step A:

[(R)-3-(3-Acetylaminopyridin-2-yl)-1-(2,5-difluorobenzyl)-2-oxopropyl]carbamic acid tert-butyl ester Using general procedure 2 with [(R)-2-(2,5-Difluoro-phenyl)-1-(methoxy-methyl-carbamoyl)-ethyl]-carbamic acid tert-butyl ester (4.85 mmol; 1.67 g) and N-(2-Methylpyridin-3-yl)acetamide (12.12 mmol; 1.82 g) gives the title compound.
¹H NMR
MS (m/e): 434.2 (M+1)
Step B:

[(1R,2S)-3-(3-Acetylaminopyridin-2-yl)-1-(2,5-difluorobenzyl)-2-hydroxypropyl]carbamic acid tert-butyl ester Using general procedure 3 with [(R)-3-(3-Acetylaminopyridin-2-yl)-1-(2,5-difluorobenzyl)-2-oxopropyl]carbamic acid tert-butyl ester (1.68 mmol; 729.00 mg) and lithium triacetoxyborohydride (8.41 mmol; 2.22 g) as the reducing agent gives the title compound.
¹HNMR
MS (m/e): 436.3 (M+1).
Step C:

N-{2-[(2S,3R)-3-Amino-4-(2,5-difluorophenyl)-2-hydroxybutyl]pyridin-3-yl}acetamide dihydrochloride Using general deprotection procedure 1 with [(1R,2S)-3-(3-Acetylaminopyridin-2-yl)-1-(2,5-difluorobenzyl)-2-hydroxypropyl]carbamic acid tert-butyl ester (0.23 mmol; 0.10 g) provides the title compound.
¹H NMR (400 MHz, DMSO-d6) δ 2.15 (s, 3H), 2.82-2.92 (m, 1H), 2.85-2.91 (m, 1H). 3.11-3.16 (m, 2H), 3.28-3.40 (m, 1H), 3.52 (br, 1H), 3.95 (br, H₂O+3H), 7.10-7.16 (m, 1H), 7.19-7.25 (m, 1 H), 7.33 (br, 1H), 7.61 (br, 1H), 8.17 (br, 2H), 8.37 (br, 1H), 8.45 (br, 1H), 9.97 (br, 1H).
MS (m/e): 336.3 (M+1).

EXAMPLE 32

2-[(2S,3R)-3-Amino-4-(2-fluoro-phenyl)-2-hydroxybutyl]-N-cyclopropyl-nicotinamide dihydrochloride

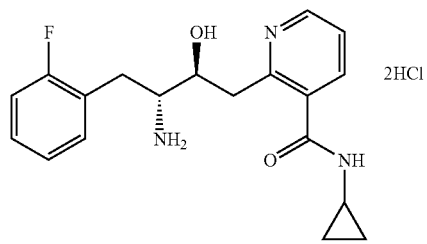

Step A:

(4R,5S)-4-(2-Fluoro-benzyl)-2,2-dimethyl-5-(3-cyclopropylcarbamoyl-pyridin-2-ylmethyl)-oxazolidine-3-carboxylic acid tert-butyl ester Using general reaction procedure 5 with 2-[(4R,5S)-3-tert-butoxycarbonyl-4-(2-fluoro-benzyl)-2,2-dimethyl-oxazolidin-5-ylmethyl]-nicotinic acid (0.3 g, 0.67 mmol) and cyclopropylamine (0.23 mL, 3.4 mmol) gives the title compound.
¹HNMR
MS (m/e): 484 (M+1).

Step B:

2-[(2S,3R)-3-Amino-4-(2-fluoro-phenyl)-2-hydroxybutyl]-N-cyclopropyl-nicotinamide dihydrochloride Using general deprotection procedure 4 with (4R,5S)-4-(2-Fluoro-benzyl)-2,2-dimethyl-5-(3-cyclopropylcarbamoyl-pyridin-2-ylmethyl)-oxazolidine-3-carboxylic acid tert-butyl ester (0.19 g, 0.39 mmol) followed by general purification method 1 gives the title compound.
¹HNMR
MS (m/e): 344 (M+1).

EXAMPLE 33

2-[(2S,3R)-3-Amino-4-(2-fluoro-phenyl)-2-hydroxybutyl]-N-cyclopropylmethyl-nicotinamide dihydrochloride

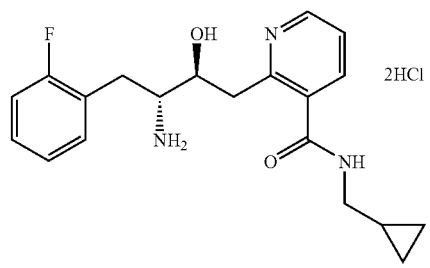

Step A:

(4R,5S)-4-(2-Fluoro-benzyl)-2,2-dimethyl-5-(3-cyclopropylmethyl-carbamoyl-pyridin-2-ylmethyl)-oxazolidine-3-carboxylic acid tert-butyl ester Using general reaction procedure 5 with 2-[(4R,5S)-3-tert-butoxycarbonyl-4-(2-fluoro-benzyl)-2,2-dimethyl-oxazolidin-5-ylmethyl]-nicotinic acid (0.3 g, 0.67 mmol) and cyclopropylmethylamine (0.29 mL, 3.3 mmol) gives the title compound.
¹HNMR
MS (m/e): 498 (M+1).

Step B:

2-[(2S,3R)-3-Amino-4-(2-fluoro-phenyl)-2-hydroxybutyl]-N-cyclopropylmethyl-nicotinamide dihydrochloride Using general deprotection procedure 4 with (4R,5S)-4-(2-Fluoro-benzyl)-2,2-dimethyl-5-(3-cyclopropylmethyl-carbamoyl-pyridin-2-ylmethyl)-oxazolidine-3-carboxylic acid tert-butyl ester (0.41 g, 0.9 mmol) followed by general purification method 1 gives the title compound.
¹HNMR
MS (m/e): 344 (M+1).

EXAMPLE 34

2-[(2S,3R)-3-Amino-4-(2,5-difluoro-phenyl)-2-hydroxy-butyl]-N-tert-butyl-6-trifluoromethyl-nicotinamide

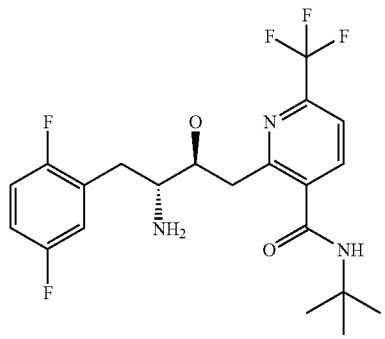

Step A:

(R)-2-Dibenzylamino-3-(2,5-difluoro-phenyl)-propionaldehyde

To a solution of (R)-2-Dibenzylamino-3-(2,5-difluoro-phenyl)-propan-1-ol (5.10 g, 13.9 mmol) in DMSO (1 mL) and Triethylamine (7.83 mL, 56.2 mmol) at −9° C. is added a solution of Sulfur Trioxide Pyridine Complex (4.43 g, 27.3 mmol) in DMSO (19.6 mL) over a period of 60 min, the reaction temperature is maintained below 4° C. The reaction is allowed to stir an additional 15 min at 0-3° C. after which the reaction is quenched by addition of water (50 mL) over a period of 60 min, the reaction temperature is maintained below 10° C. The product is extracted into MTBE, the organic phase is dried over sodium sulfate, filtered, and concentrated under reduced pressure to provide the title compound.

Step B:

N-tert-Butyl-2-[(2S,3R)-3-dibenzylamino-4-(2,5-difluoro-phenyl)-2-hydroxy-butyl]-6-trifluoromethyl-nicotinamide To a solution of Diisopropylamine (4.78 mL, 34.0 mmol) in THF (22.0 mL) at −78° C. is added Butyl Lithium (13.6 mL, 34.0 mmol) dropwise over 20 minutes. The resulting solution is stirred at −78° C. for 30 minutes after which a solution of Intermediate 4 (3.61 g, 13.9 mmol) and Tetramethylenediamine (5.12 mL, 34.0 mmol) in THF (32 mL) is added dropwise over 60 min, the reaction temperature is maintained below −58° C. The resulting solution is stirred at −78° C. for 60 min. To the reaction is added a solution of (R)-2-Dibenzylamino-3-(2,5-difluoro-phenyl)-propionaldehyde (4.60 g, 12.6 mmol) in anhydrous THF (16 mL) dropwise over 2 hours. The reaction is allowed to warm to −40° C. over 2 hours after which the reaction is quenched by addition of water (40 mL). The pH is adjusted to 9 with 5N HCL and the product is extracted into EtOAc. The organic phase is dried over magnesium sulfate, filtered, and concentrated under reduced pressure to provide the title compound. The title compound is recrystallized using acetonitrile (87 mL) and water (26.1 mL).

Step C:

2-[(2S,3R)-3-Amino-4-(2,5-difluoro-phenyl)-2-hydroxy-butyl]-N-tert-butyl-6-trifluoromethyl-nicotinamide To 10% Pd/C (0.94 g, 0.44 mmoles) in MeOH (40 mL) is added N-tert-Butyl-2-[(2S,3R)-3-dibenzylamino-4-(2,5-difluoro-phenyl)-2-hydroxy-butyl]-6-trifluoromethyl-nicotinamide (5.89 g, 9.42 mmoles) rinsed in with 19 mL of MeOH. To the reaction is added a solution of Formic Acid, Ammonium Salt (2.35 g, 37.4 mmol) in water 6.0 mL and heated to 40° C. for 20 minutes. The reaction is allowed to cool, the catalyst filtered, washed with MeOH and the organics concentrated under reduced pressure. The concentrate is taken up in MTBE and water to which is added $NH_4OH$ (pH~10) and the aqueous layer extracted with MTBE. The organic phase is dried over sodium sulfate, filtered, and concentrated under reduced pressure to provide the title compound.

1H NMR (CDCl3, 300 MHz): 1.49 (s, 9 H), 2.70-2.58 (m, 1 H), 3.20-3.05 (m, 3 H), 3.40-3.30 (m, 1 H), 4.10-4.00 (m, 1 H), 7.42-6.81 (m, 5 H), 7.59 (d, 1 H), 7.90 (d, 1H).

EXAMPLE 35

2-[(2S,3R)-3-Amino-4-(2,5-difluoro-phenyl)-2-hydroxy-butyl]-N-tert-butyl-6-trifluoromethyl-nicotinamide (Form I)

To a solution of 2-[(2S,3R)-3-Amino-4-(2,5-difluoro-phenyl)-2-hydroxy-butyl]-N-tert-butyl-6-trifluoromethyl-nicotinamide (207.4 mg) in IPrOH (400 µL) at 60° C. is added n-heptane (10 mL) and allowed to cool, the resulting solid is filtered and washed with minimum n-heptane to provide the title compound.

XRD—2θ6.9, 8.8, 12.8, 17.6, 20.8, 21.7, 23.5

EXAMPLE 36

2-[(2S,3R)-3-Amino-4-(2,5-difluoro-phenyl)-2-hydroxy-butyl]-N-tert-butyl-6-trifluoromethyl-nicotinamide (Form II)

A solution of 2-[(2S,3R)-3-Amino-4-(2,5-difluoro-phenyl)-2-hydroxy-butyl]-N-tert-butyl-6-trifluoromethyl-nicotinamide (207.2 mg) in Acetone (500 µL) at 20° C. is cooled and the resulting solid is filtered to provide the title compound.

XRD—2θ7.9, 9.3, 13.5, 15.5, 15.9, 20.7, 28.5

X-ray Powder Diffraction—XRPD patterns were obtained on a Bruker D8 Advance X-ray powder diffractometer, equipped with a CuKα source (λ=1.54056 angstrom) and an electronic solid-state detector, operating at 40 kV and 40 mA. Each sample was scanned between 4° and 40° in 2θ, with a step size of 0.02° in 2θ and a maximum scan rate of 3 second/step, and with controlled variable (v12) divergence and receiving slits and a 0.2 mm detector slit.

The compound of formula I is preferably formulated in a unit dosage form prior to administration. Therefore, yet another aspect of the present invention is a pharmaceutical composition comprising a compound of formula I and one or more pharmaceutically acceptable carriers, diluents or excipients.

The present pharmaceutical compositions are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

The pharmacological profile of the present compounds may be demonstrated as follows:

Human Recombinant DPIV Activity Assay

The DPIV assay uses a fluorometric end point assay (excitation 355 nm; emission 460 nm), enriched human recombinant DPIV enzyme (21.3 µU/µl), and Gly-Pro-AMC (Bachem I-1225) as substrate (0.02 mM). Secreted DPIV (lacking membrane anchor) is enriched from HEK293 cell culture supernatant by ultrafiltration, ultra-centrifugation, and size-exclusion chromatography. IC50 values of the compounds are calculated based on a 12 points concentration response curve. Each concentration is measured in duplicate. The assay is validated by plate variability and conformity, inter-plate variability, signal window, and minimum significant ration of IC50. A MSR is calculated based on a test/retest analysis and a retrospective analysis. The MSR value is 1.8.

Using this assay the preferred compounds of the invention described within the examples show activity with an IC50 less than or equal to 100 µM.

| Example | IC50 (µM) |
|---------|-----------|
| 8 | 0.030 |
| 10 | 0.342 |
| 23 | 0.022 |
| 27 | 0.232 |

We claim:
1. A compound of the formula I:

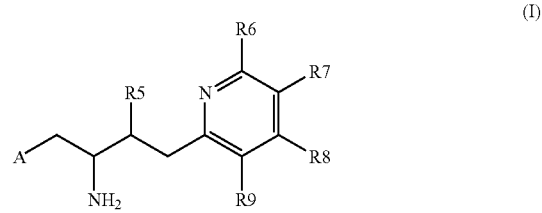

or a pharmaceutically acceptable salt thereof;
wherein
A is

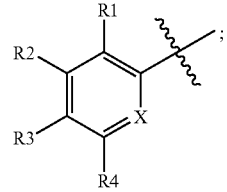

R1 is selected from H, halo, $C_1$-$C_4$ alkyl, and $C_1$-$C_4$ haloalkyl;
R2, R3, and R4 are independently selected from H, halo, methyl, and $C_1$-$C_2$ haloalkyl;
X is CH;
R5 is H or —OR12;
R6 is H or $C_1$-$C_6$ haloalkyl;
R7 and R8 are H;
R9 is —NR13C(O)R14 or —C(O)NR10R11;

R10 and R11 are independently selected from H, $C_1$-$C_6$ alkyl, $C_1$-$C_6$ haloalkyl, aryl, $C_3$-$C_6$ cycloalkyl, $C_1$-$C_6$ alkylaryl, $C_1$-$C_6$ alkyl-$C_3$-$C_6$ cycloalkyl or R10 and R11 combine with the N of R9 to form piperidinyl;

where R10 or R11 are aryl or $C_1$-$C_6$ alkylaryl the aryl substituent is optionally substituted with 1-3 substituents selected from methoxy;

R12 is H or $C_1$-$C_6$ alkyl;

R13 H;

R14 is $C_1$-$C_6$ alkyl.

2. A compound according to claim 1 of the formula I:

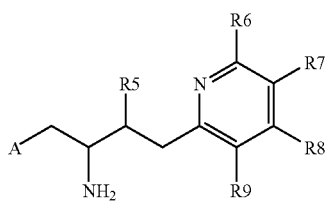

(I)

wherein

R9 is —C(O)NR10R11; and

R10 and R11 are independently selected from H, $C_1$-$C_6$ alkyl, $C_1$-$C_6$ haloalkyl, aryl, $C_1$-$C_6$ alkylaryl, or R10 and R11 combine with the N of R9 to form piperidinyl; or a pharmaceutically acceptable salt thereof.

3. A compound according to claim 1 wherein R5 is —OR12.

4. A compound according to claim 1 of the formula IIb:

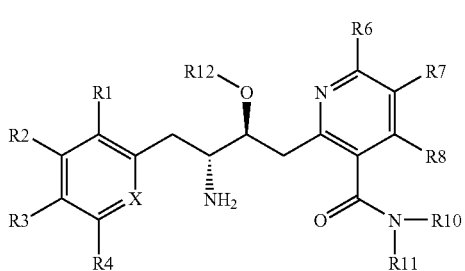

(IIb)

or a pharmaceutically acceptable salt thereof.

5. A compound according to claim 1 wherein R1, R2, R3, and R4 are independently selected from H, F, Cl, $CH_3$ and $CF_3$.

6. A compound according to claim 1 wherein R1 and R4 are independently selected from H, F, Cl, $CH_3$ and $CF_3$ and R2 and R3 are independently selected from H, F and Cl.

7. A compound according to claim 6 wherein R1 and R4 are independently selected from F, Cl and $CH_3$.

8. A compound according to claim 7 wherein R1 is F and R4 is either Cl or F.

9. A compound according to claim 1 wherein R3 is selected from H and F.

10. A compound according to claim 9 wherein R3 is F.

11. A compound according to claim 1 wherein R2 is H.

12. A compound according to claim 1 wherein R6, R7 and R8 are H.

13. A compound according to claim 1 wherein R10 and R11 are independently selected from H, $C_1$-$C_4$ alkyl, aryl and $C_1$-$C_4$ alkylaryl wherein the aryl substituent of $C_1$-$C_4$ alkylaryl is optionally substituted with methoxy.

14. A compound according to claim 13 wherein R10 and R11 are independently selected from H, methyl, isopropyl, t-butyl, phenyl, benzyl, 1-methyl benzyl and 1,1-dimethyl benzyl wherein phenyl and benzyl substituents are optionally substituted with methoxy.

15. A compound according to claim 1 wherein R10 is H.

16. A compound according to claim 1 wherein R11 is t-butyl.

17. A compound according to claim 1 wherein R12 is H.

18. A pharmaceutical composition comprising a compound of claim 1, or a pharmaceutically acceptable salt thereof, and a pharmaceutically acceptable diluent or carrier.

19. A method for treatment of type II diabetes which comprises administering an effective amount a compound of claim 1, or a pharmaceutically acceptable salt thereof, to a human being or animal in need thereof.

* * * * *